United States Patent
Cuniere et al.

(10) Patent No.: US 12,378,246 B2
(45) Date of Patent: Aug. 5, 2025

(54) SYNTHETIC OPTIONS TOWARDS THE MANUFACTURE OF (6R,10S)-10-{4-[5-CHLORO-2-(4-CHLORO-1H-1,2,3-TRIAZOL-1-YL)PHENYL]-6-OXO-1(6H)-PYRIMIDINYL} -1-(DIFLUOROMETHYL)-6-METHYL-1,4,7,8,9,10-HEXAHYDRO-11,15-(METHENO) PYRAZOLO[4,3-B][1,7]DIAZACYCLOTETRA-DECIN-5(6H)-ONE

(71) Applicants: BRISTOL-MYERS SQUIBB COMPANY, Princeton, NJ (US); JANSSEN PHARMACEUTICA NV, Beerse (BE)

(72) Inventors: Nicolas Cuniere, Princeton, NJ (US); Yu Fan, Highland Park, NJ (US); Sergei Kolotuchin, Princeton, NJ (US); Subha Mukherjee, Princeton, NJ (US); Eric M. Simmons, Princeton, NJ (US); Amarjit Singh, Princeton, NJ (US); Carolyn S. Wei, Princeton, NJ (US); Yi Xiao, Princeton, NJ (US); Changxia Yuan, Princeton, NJ (US); Bin Zheng, Princeton, NJ (US); Simon Albert Wagschal, Schaffhausen (CH); Diego Fernando Domenico Broggini, Schaffhausen (CH); Duy Chi Trung Cao, Schaffhausen (CH); Kostiantyn Chernichenko, Beerse (BE); Sebastien Francois Emmanuel Lemaire, Beerse (BE); Cyril Ben Haïm, Beerse (BE)

(73) Assignees: Bristol-Myers Squibb Company, Princeton, NJ (US); Janssen Pharmaceutica NV, Beerse (BE)

( * ) Notice: Subject to any disclaimer, the term of this patent is extended or adjusted under 35 U.S.C. 154(b) by 921 days.

(21) Appl. No.: 17/602,059

(22) PCT Filed: Apr. 10, 2020

(86) PCT No.: PCT/US2020/027655
§ 371 (c)(1),
(2) Date: Oct. 7, 2021

(87) PCT Pub. No.: WO2020/210613
PCT Pub. Date: Oct. 15, 2020

(65) Prior Publication Data
US 2022/0144836 A1 May 12, 2022

Related U.S. Application Data

(60) Provisional application No. 62/832,614, filed on Nov. 4, 2019.

(51) Int. Cl.
C07D 471/18 (2006.01)
C07D 213/61 (2006.01)
C07D 401/04 (2006.01)

(52) U.S. Cl.
CPC ......... C07D 471/18 (2013.01); C07D 213/61 (2013.01); C07D 401/04 (2013.01)

(58) Field of Classification Search
None
See application file for complete search history.

(56) References Cited

U.S. PATENT DOCUMENTS

2012/0238549 A1 9/2012 Cusack et al.
2016/0096839 A1 4/2016 Dilger et al.

FOREIGN PATENT DOCUMENTS

| CN | 105294496 A | 2/2016 |
|---|---|---|
| EP | 3 293 186 A1 | 3/2018 |
| WO | 2015116886 A1 | 8/2015 |
| WO | 2016053455 A1 | 4/2016 |
| WO | 2018133793 A1 | 7/2018 |
| WO | 2020211781 A1 | 10/2020 |
| WO | 2021013209 A1 | 1/2021 |
| WO | 2021207208 A1 | 10/2021 |

*Primary Examiner* — Adam C Milligan
*Assistant Examiner* — Jason M. Nolan
(74) *Attorney, Agent, or Firm* — Mintz, Levin, Cohn, Ferris, Glovsky and Popeo, P.C.

(57) ABSTRACT

Highly efficient methods are provided for preparing key intermediates in the synthesis of Compound (I), which are broadly applicable and can provide selected components having a variety of substituents groups.

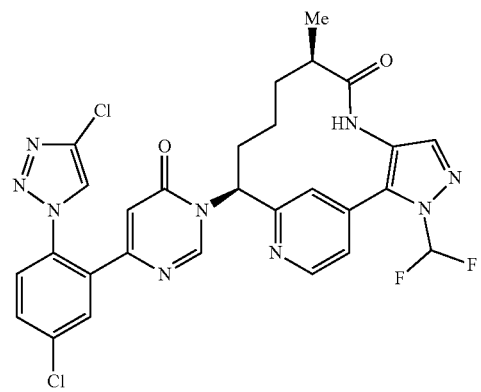

13 Claims, No Drawings

SYNTHETIC OPTIONS TOWARDS THE MANUFACTURE OF (6R,10S)-10-{4-[5-CHLORO-2-(4-CHLORO-1H-1,2,3-TRIAZOL-1-YL)PHENYL]-6-OXO-1(6H)-PYRIMIDINYL}-1-(DIFLUOROMETHYL)-6-METHYL-1,4,7,8,9,10-HEXAHYDRO-11,15-(METHENO)PYRAZOLO[4,3-B][1,7]DIAZACYCLOTETRADECIN-5(6H)-ONE

CROSS-REFERENCE TO RELATED APPLICATIONS

This is application is a continuation of International Patent Application No. PCT/US2020/027655, filed Apr. 10, 2020, which claims priority benefit of U.S. Provisional Application No. 62/832,614 filed Apr. 11, 2019, each of which is incorporated herein by reference in its entirety for all purposes.

FIELD OF THE INVENTION

The invention generally relates to several improved processes for the preparation of (6R,10S)-10-{4-[5-chloro-2-(4-chloro-1H-1,2,3-triazol-1-yl)phenyl]-6-oxo-1(6H)-pyrimidinyl}-1-(difluoromethyl)-6-methyl-1,4,7,8,9,10-hexahydro-11,15-(metheno)pyrazolo[4,3-b][1,7]diazacyclotetradecin-5(6H)-one, a FXIa inhibitor useful for the treatment of thromboembolic disorders, which include venous thrombosis and deep vein thrombosis.

BACKGROUND OF THE INVENTION

Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

U.S. Pat. No. 9,453,018 discloses macrocycle compounds as factor XIa inhibitors useful for the treatment of thromboembolic disorders. One of the compounds has the following structure:

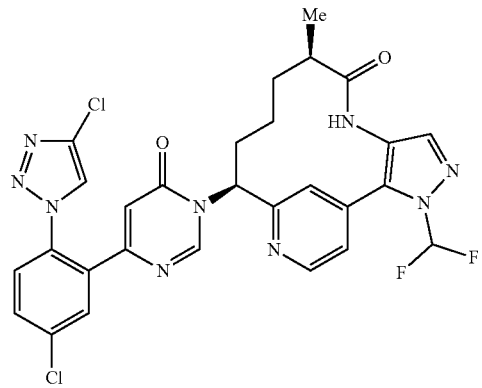

Compound (I)

The U.S. patent discloses a multistep synthesis process for preparing the macrocycle compound. This process includes the coupling of a pyridine-containing macrocycle with a pyrimidinol to form Compound (I). The disclosed process also includes a ring-closing metathesis process using catalysts such as Grubbs (II).

There are difficulties associated with the adaptation of the multistep synthesis disclosed in U.S. Pat. No. 9,453,018 to a larger scale synthesis, such as production in a pilot plant or on a manufacturing scale. One difficulty is that the Grubbs (II) reagent was not readily adaptable to commercial scale synthesis due to its high costs. Further, there is a continuing need to find a process that provides higher yields in order to improve manufacturing economics and/or reduce waste. Preferably, a new process will employ less expensive starting materials.

Desired is a process that is suitable for preparing larger quantities of Compound (I) than is typically prepared by laboratory scale processes. Also desired is a process that provides higher yields of Compound (I) than the previously disclosed processes.

The present invention is directed to one or both of these, as well as other important aspects.

SUMMARY OF THE INVENTION

In one aspect, the present invention provides a method for the preparation of Compound (I):

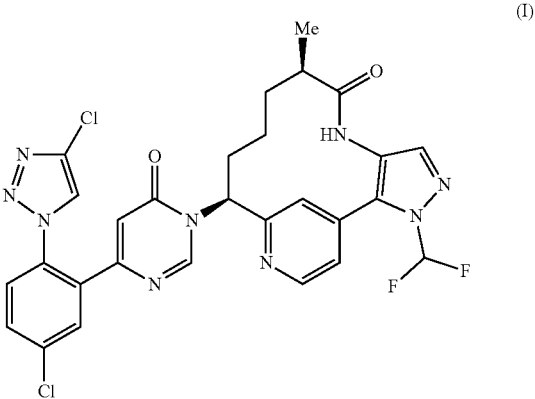 [SMILES: C[C@@H]1CCC[C@H](n2cnc(-c3cc(Cl)ccc3-n3cc(Cl)nn3)cc2=O)c2cc(ccn2)-c2c(cnn2C(F)F)NC1=O]

(I)

comprising the steps of
1) reacting Compound 1 of the structure

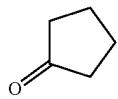

Compound 1 with Compound 2 of the formula

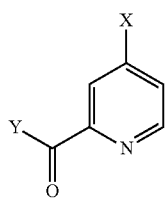

Compound 2 wherein
X is selected from Cl, Br, and I;
Y is selected from $OR^9$, $NHOC_{1-3}$ alkyl, Cl, Br, and I; and
$R^9$ is selected from $C_{1-3}$ alkyl, $C_{1-3}$ hydroxyalkyl, substituted phenyl and substituted benzyl; in a suitable solvent to yield Compounds 3a or 3b of the formulae

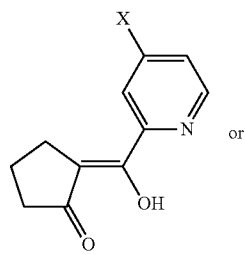

Compound 3a or

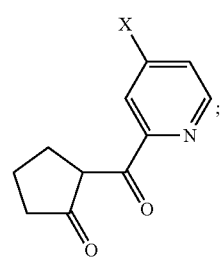

Compound 3b 2) converting Compound 3a or 3b to Compound 4 of the formula in the presence of an acid

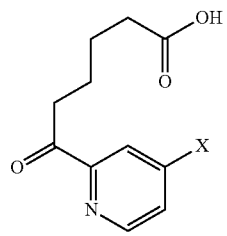

Compound 4

3) subsequently reacting Compound 4 in an alcoholic solvent with a tri-alkyl orthoformate to yield Compound 5 of the formula

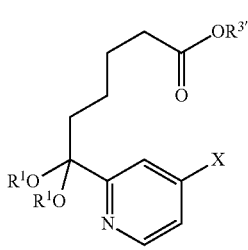

Compound 5 wherein
$R^1$ is $C_{1-6}$ alkyl;
and $R^{3'}$ is selected from $C_{1-6}$ alkyl, optionally substituted phenyl and benzyl;

4) which is ester hydrolyzed under basic condition or undergoes hydrogenolysis when $R^3$ is substituted benzyl to Compound 6 of the formula

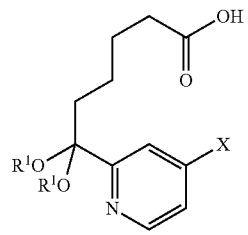

Compound 6 wherein $R^1$ and X are as defined above;

5) subsequently activating the carboxylic moiety of Compound 6 and reacting it with a chiral auxiliary to form Compound 6a of the formula

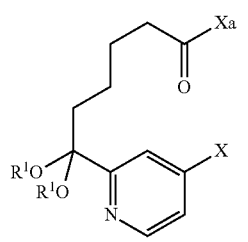

Compound 6a wherein Xa is the chiral auxiliary and $R^1$ and X are as defined above;

6) then reacting Compound 6a with a base in the presence of a methyl donor such as alkyl halides in the presence of a chiral auxiliary to Compound 7 of the formula

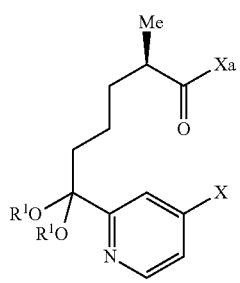

Compound 6b wherein R¹, X, and Xa are as defined above;

7) removing the chiral auxiliary Xa to obtain Compound 7 of the formula

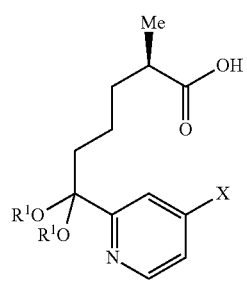

Compound 7 wherein R¹ and X are as defined above;

8) subsequently reacting Compound 7 in the presence of a metal catalyst with Compound 8 of the structure

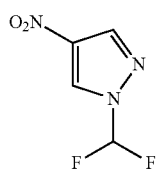

Compound 8 to yield Compound 9

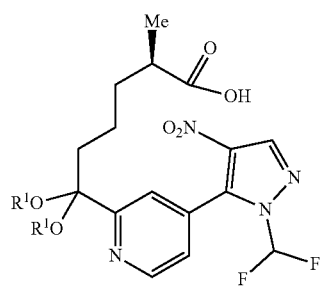

Compound 9

9) reducing the nitro group in Compound 9 to Compound 10 of the formula

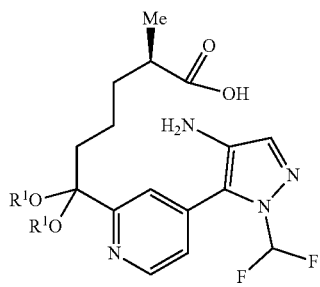

Compound 10

10) cyclizing Compound 10 with a suitable coupling agent to yield Compound 11

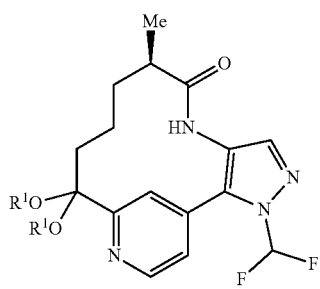

Compound 11

11) unmasking the ketone functionality in the presence of an acid to yield Compound 12

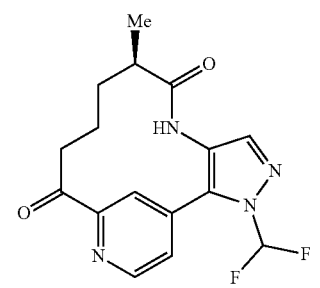

Compound 12

12a) reducing Compound 12 with an ammonia equivalent in the presence of a reducing agent or 12b) a transaminase enzyme in the presence of an amine source, different recycling systems, and a co-factor to generate the amine stereogenic center present in Compound 13

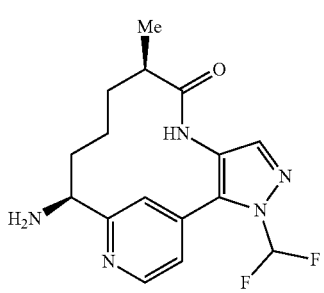

Compound 13

13) which is then coupled with Compound 14 of the structure

Compound 14

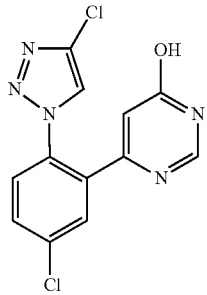

to yield Compound (I):

Compound (I)

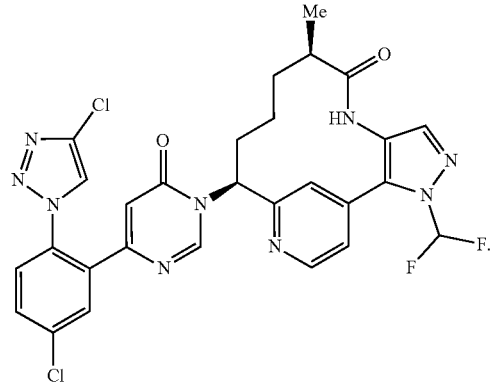

In yet another aspect, the present invention provides compounds of Formula (II):

(II)

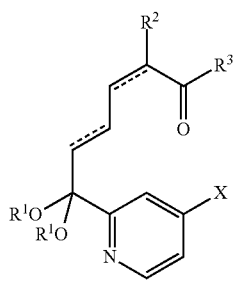

or the form of a free base or salt, wherein
---- is an optional bond;
$R^1$ is $C_{1-6}$ alkyl, preferably Me;
$R^2$ is $C_{1-3}$ alkyl, preferably Me;
$R^3$ is selected from OH, $OC_{1-4}$ alkyl,

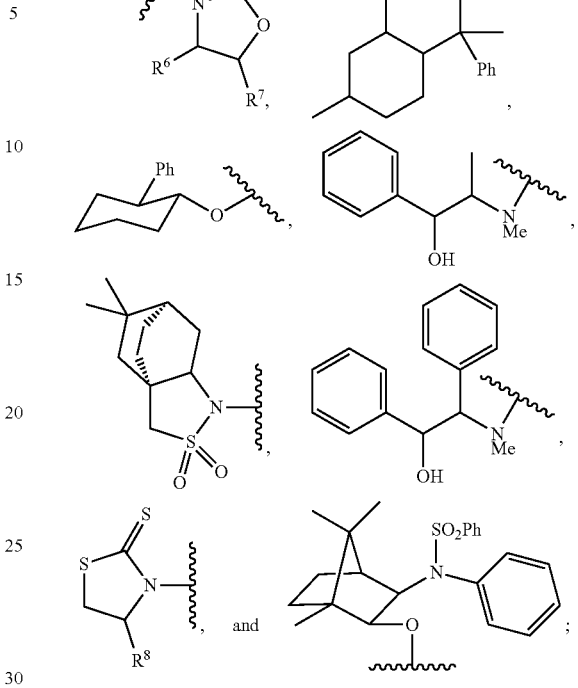

wherein
$R^6$ is selected from $C_{1-3}$ alkyl, phenyl, and benzyl;
$R^7$ is selected from H and phenyl;
$R^8$ is selected from $C_{1-3}$ alkyl, phenyl, and benzyl; and
X is selected from F, Cl, Br and I.

In some embodiments of the compound of Formula (II):
$R^1$ is $C_{1-6}$ alkyl;
$R^2$ is $C_{1-3}$ alkyl;
$R^3$ is selected from OH, $OC_{1-6}$ alkyl,

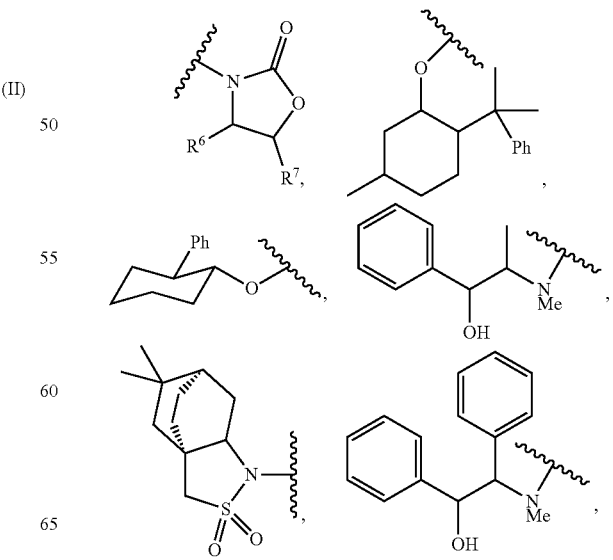

-continued

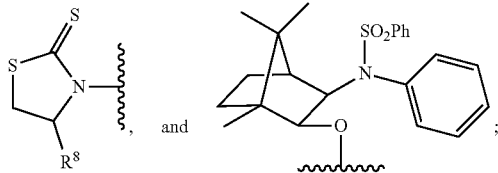
, and ;

wherein
$R^6$ is selected from $C_{1-3}$ alkyl, phenyl, and benzyl;
$R^7$ is selected from H and phenyl;
$R^8$ is selected from $C_{1-3}$ alkyl, phenyl, and benzyl; and
X is selected from F, Cl, Br and I.

In some embodiments of the compound of Formula (II), or a pharmaceutically acceptable salt thereof:
$R^1$ is methyl;
$R^2$ is methyl;
$R^3$ is OH; and
X is Cl.

In some embodiments of the compound of Formula (II):
$R^1$ is methyl;
$R^2$ is methyl;
$R^3$ is OH; and
X is Cl; the compound is as its free base or its (1S, 2R)-2-amino-1,2-diphenylethane-1-ol salt or its dicyclohexylamine salt.

In yet another aspect, the present invention provides compounds of Formula (IIa):

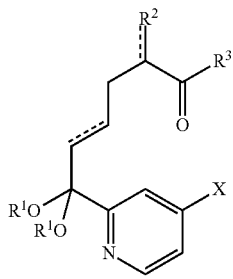

(IIa)

or the form of a free base or salt, wherein
---- is an optional bond;
$R^1$ is $C_{1-6}$ alkyl, preferably Me;
$R^2$ is $C_{1-3}$ alkyl or $C_{1-3}$ alkenyl, preferably Me or $CH_2$;
$R^3$ is selected from OH, $OC_{1-4}$ alkyl,

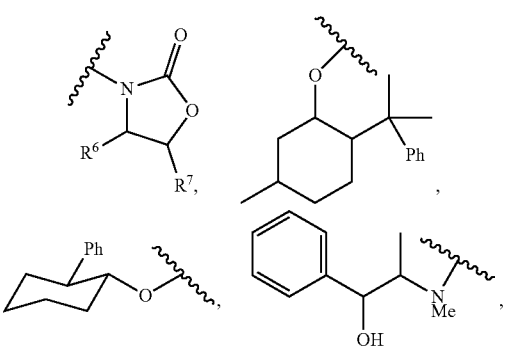

-continued

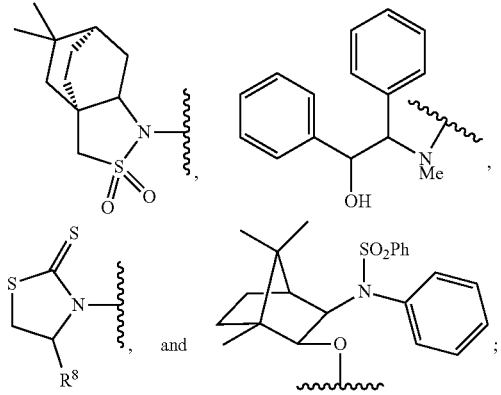
,

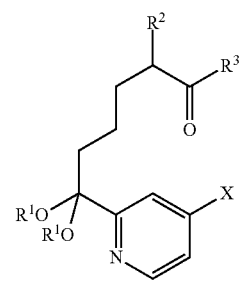
and ;

wherein
$R^6$ is selected from $C_{1-3}$ alkyl, phenyl, and benzyl;
$R^7$ is selected from H and phenyl;
$R^8$ is selected from $C_{1-3}$ alkyl, phenyl, and benzyl; and
X is selected from F, Cl, Br and I.

In some embodiments, the process of making a compound of Formula (II) having the structure:

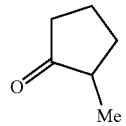

(II)

wherein
$R^1$ is methyl;
$R^2$ is methyl;
$R^3$ is OH; and
X is Cl;
comprises the steps of
a) reacting Compound 22 of the formula Compound 22

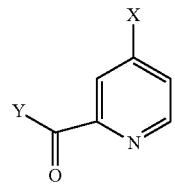

with Compound 2 of the formula

Compound 2 wherein

X is selected from Cl, Br, and I;
Y is selected from OR⁹, NHOC$_{1-3}$ alkyl, Cl, Br, and I; and
R⁹ is selected from C$_{1-3}$ alkyl, C$_{1-3}$ hydroxyalkyl, substituted phenyl and substituted benzyl; in a suitable solvent to yield Compound 23 of the formula

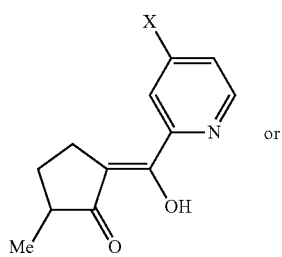

Compound 23a or

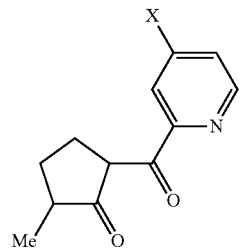

Compound 23b b) converting Compound 23a or 23b to Compound 24 of the formula in the presence of an acid

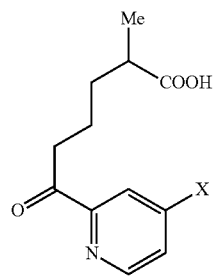

Compound 24 c) subsequently reacting Compound 24 with trimethyl orthoformate or triethyl orthoformate to yield Compound 25 of the formula

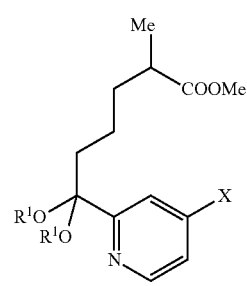

Compound 25 wherein R¹ is methyl or ethyl and X is as defined above;
d) Converting Compound 25 with an enzyme to Compound 26 of the formula

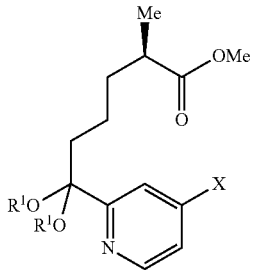

Compound 26 wherein R¹ and X are as defined above;

e) hydrolyzing Compound 26 to Compound 27 of the formula

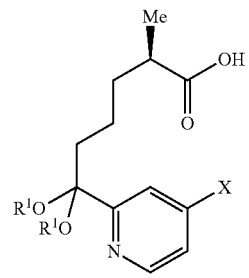

Compound 27 wherein R¹ and X are as defined above.

In some embodiments of the process of making a compound of Formula (II), the enzyme is a lipase.

In some embodiments, the process of preparing a compound of Formula (II) or (IIa) having the structure of Compound 21:

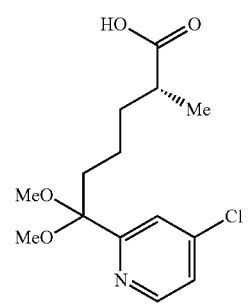

Compound 21 comprises the steps of
1) reacting a cyclopentane ester derivative of the formula

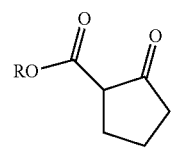

wherein R is C$_{1-6}$ alkyl, with a dialkylamine to yield Compound 40 of the formula

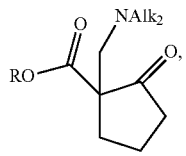
Compound 40 wherein Alk is $C_{1-6}$ alkyl;

2) combining Compound 40 with a first base to form Compound 41 of the structure

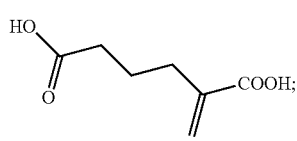
Compound 41

3) reacting Compound 41 with an acid and an alcohol $R^{3'}OH$ to form Compound 40 of the formula

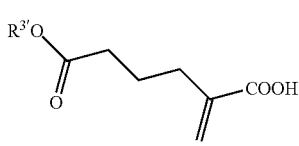
Compound 42 wherein $R^{3'}$ is $C_{1-6}$ alkyl;

4) reacting Compound 42 and Compound 2a of the structure:

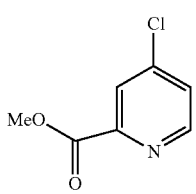
Compound 2a in the presence of a second base to yield Compound 18b of the formula

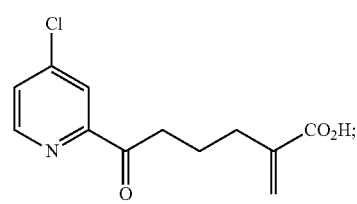
Compound 18b 5) converting Compound 18b to Compound 20b of the structure

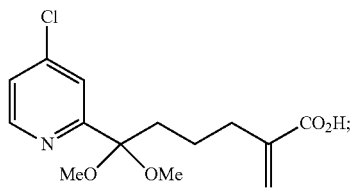
Compound 20b and 6) hydrogenating Compound 20b to yield a compound of Formula (II) having the structure

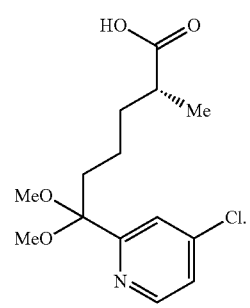
Compound 21

In some embodiments of the process of preparing the compound of Formula (II) or (IIa) having the structure of Compound 21, the hydrogenating in step (6) comprises a chiral Ru catalyst.

In some embodiments, the process of preparing a compound of Formula (II) or (IIa) having the formula of Compound 19:

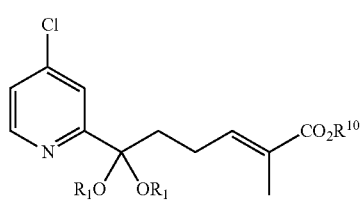
Compound 19 wherein
  $R_1$ is $C_{1-6}$ alkyl;
  $R^{10}$ is $C_{1-6}$ alkyl;
comprises the steps of:
  1) reacting Compound 37 of the formula:

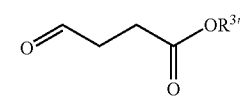
Compound 37 with a pyruvic acid ester phosphonium ylide to form Compound 37 of the formula:

Compound 38

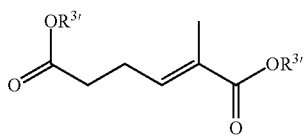

wherein R³' is independently C₁₋₆ alkyl;

2) reacting Compound 38 with Compound 2a having the structure:

Compound 2a

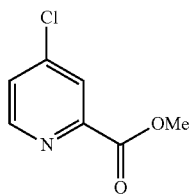

in the presence of a base to form Compound 39 of the formula:

Compound 39

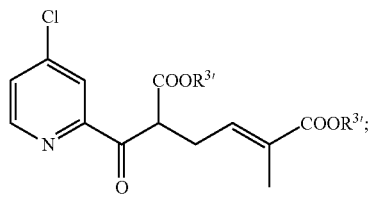

3) treating Compound 39 with a first acid to form Compound 18a of the structure:

Compound 18a

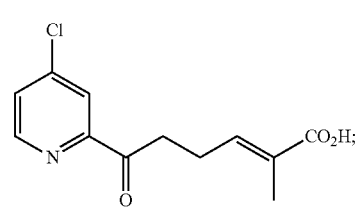

reacting Compound 18a with a C₁₋₆ alkyl alcohol and a second acid, and optionally a drying agent, to form Compound 19.

In yet another aspect, the present invention provides compounds of Formula (III):

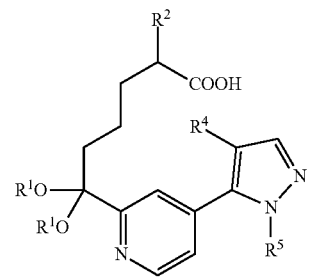
(III)

wherein
R¹ is C₁₋₆ alkyl;
R² is C₁₋₃ alkyl;
R⁴ is selected from NO₂, N═O, NHOH, and NH₂; and
R⁵ is selected from CHF₂, CD₃, and CH₃.

In some embodiments of the compound of Formula (III),
R¹ is methyl;
R² is methyl;
R⁴ is selected from NO₂ and NH₂; and
R⁵ is CHF₂.

In yet another aspect, the present invention provides compounds of Formula (IV):

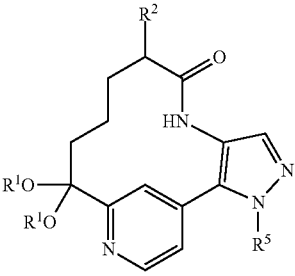
(IV)

wherein
R¹ is C₁₋₆ alkyl;
R² is C₁₋₃ alkyl; and
R⁵ is selected from CHF₂, CD₃, and CH₃.

In some embodiments of the compound of Formula (IV):
R¹ is methyl;
R² is methyl; and
R⁵ is CHF₂.

In yet another aspect, the present invention provides compounds of Formula (V):

(V)

wherein $R^2$ is $C_{1-3}$ alkyl; and
$R^5$ is selected from $CHF_2$, $CD_3$, and $CH_3$.

In some embodiments of the compound of Formula (V), $R^2$ is methyl; and $R^5$ is $CHF_2$.

In yet another aspect, the present invention provides compounds of Formula (VI):

(VI)

or the form of a free base or salt, wherein
$R^2$ is $C_{1-3}$ alkyl;
$R^3$ is selected from OH, $OC_{1-4}$ alkyl, wherein
$R^6$ is selected from $C_{1-3}$ alkyl, phenyl, and benzyl;
$R^7$ is selected from H and phenyl;
$R^8$ is selected from $C_{1-3}$ alkyl, phenyl, and benzyl; and
X is selected from F, Cl, Br and I.

In some embodiments of the compound of Formula (VI):
$R^2$ is $C_{1-3}$ alkyl;
$R^3$ is selected from OH, $OC_{1-4}$ alkyl, and and
X is selected from F, Cl, Br and I.

In some embodiments, the compound of Formula (VI) has the structure of Compound 34:

Compound 34

In another aspect, the present invention provides a method for treating a thromboembolic disorder, comprising administering to a mammalian species, preferably a human, in need thereof, a therapeutically effective amount of Compound (I), wherein Compound (I) is prepared utilizing the novel process steps of the invention.

DETAILED DESCRIPTION OF THE INVENTION

Definitions

As used herein, the term "alkyl" refers to a straight or branched, saturated aliphatic radical containing one to ten carbon atoms, unless otherwise indicated e.g., alkyl includes methyl, ethyl, propyl, isopropyl, butyl, sec-butyl, isobutyl, tert-butyl, and the like. The term "lower alkyl" refers to an alkyl radical having from one to four carbon atoms.

The term "alkoxy" refers to a group having the formula —O-alkyl, in which an alkyl group, as defined above, is attached to the parent molecule via an oxygen atom. The alkyl portion of an alkoxy group can 1 to 10 carbon atoms (i.e., $C_1$-$C_{10}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or -OEt), t-butoxy (—O—$C(CH_3)_3$ or -OtBu) and the like.

The term "aryl" refers to a monocyclic or fused bicyclic ring assembly containing 6 to 10 ring carbon atoms wherein each ring is aromatic e.g., phenyl or naphthyl.

The term "substituents" refers to an additional substituent group selected from halogen (preferably fluoro, chloro, or bromo), hydroxy, amino, mercapto, and the like. Preferred substituents for the groups described herein as substituted lower alkyl or substituted alkyl are halogens, particularly fluoro substituents.

The term "reducing agent" refers to any reagent that will decrease the oxidation state of a carbon atom in the starting material by either adding a hydrogen atom to this carbon or adding an electron to this carbon and as such would be obvious to one of ordinary skill and knowledge in the art. The definition of "reducing reagent" includes but is not limited to: borane-dimethyl sulfide complex, 9-borabicyclo [3.3.1]nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "removable protecting group" or "protecting group" refers to any group which when bound to a functionality, such as the oxygen atom of a hydroxyl or carboxyl group or the nitrogen atom of an amine group, prevents reactions from occurring at these functional groups and which protecting group can be removed by conventional chemical or enzymatic steps to reestablish the functional group. The particular removable protecting group employed is not critical.

The term "ligand" as used herein refers to a phosphine derivative that ligates palladium such as a mono or bidentate aryl or alkyl phosphine, which is capable of complexing a palladium atom. The term is well known to one skilled in the particular art.

The term "silylation" or "silylating" as used herein refers to the process of introducing a silyl, or silicon containing, group. Silyl groups include, but are not limited to, tert-butyldimethylsilyl (TBDMS), triisopropylsilyl (TIPS), triethylsilyl (TES), trimethylsilyl (TMS), tert-butyldiphenylsilyl (TBDPS), triisopropylsilyl-oxy-methyl (TOM), and di-tert-butylsilylbis (trifluoromethanesulfonate).

The term "desilylation" as used herein refers to the process of removing a silyl or silicon containing group.

EMBODIMENTS OF THE INVENTION

The present invention resides in a number of synthetic intermediates and processes for preparing those intermediates and Compound (I).

General aspects of these exemplary methods are described in the schemes and the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

In one embodiment, the present invention provides a process for the preparation of a Compound (I). A representative general method for the preparation of the derivative is outlined in Schemes 1 and 2 below.

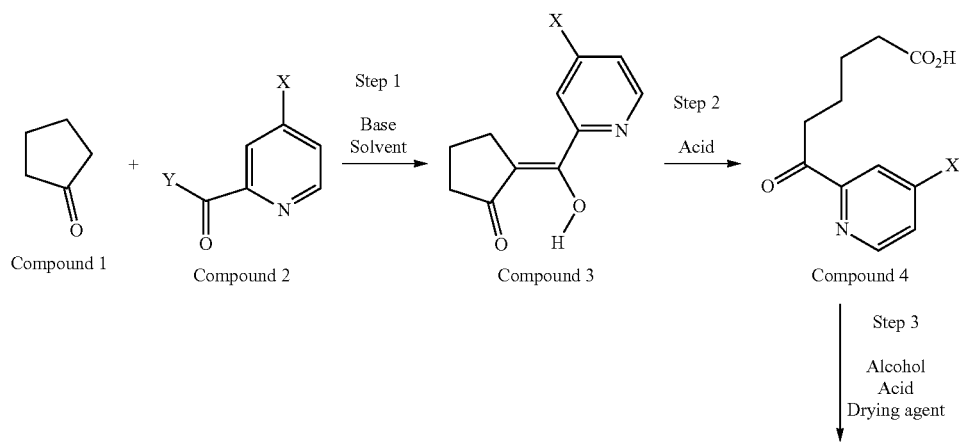

Scheme 1

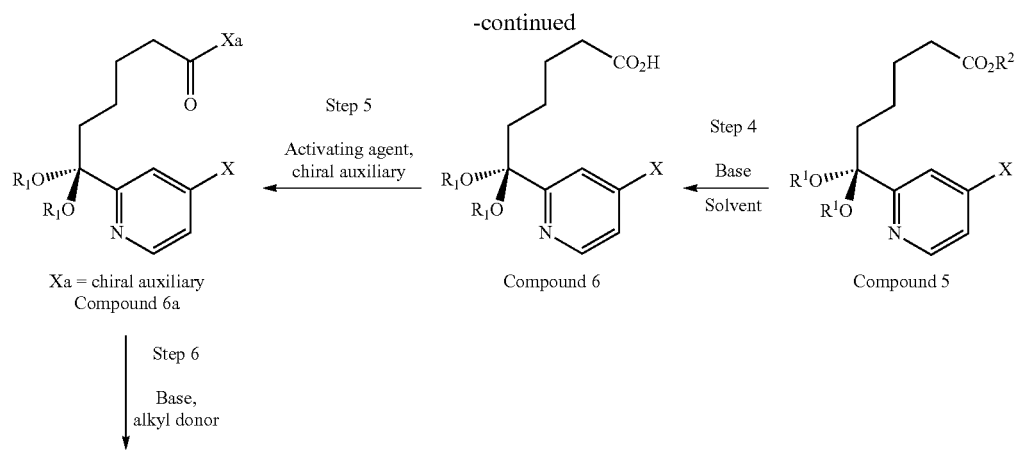
Xa = chiral auxiliary
Compound 6a
Compound 6
Compound 5
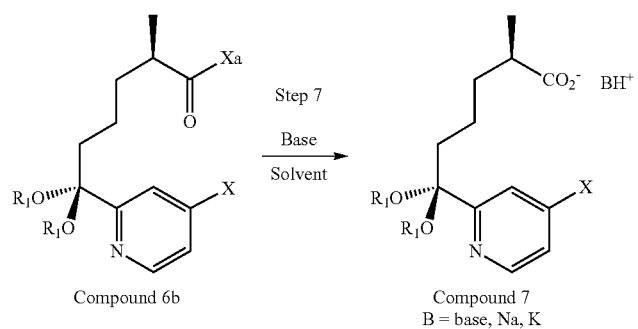
Compound 6b
Compound 7
B = base, Na, K
Scheme 2
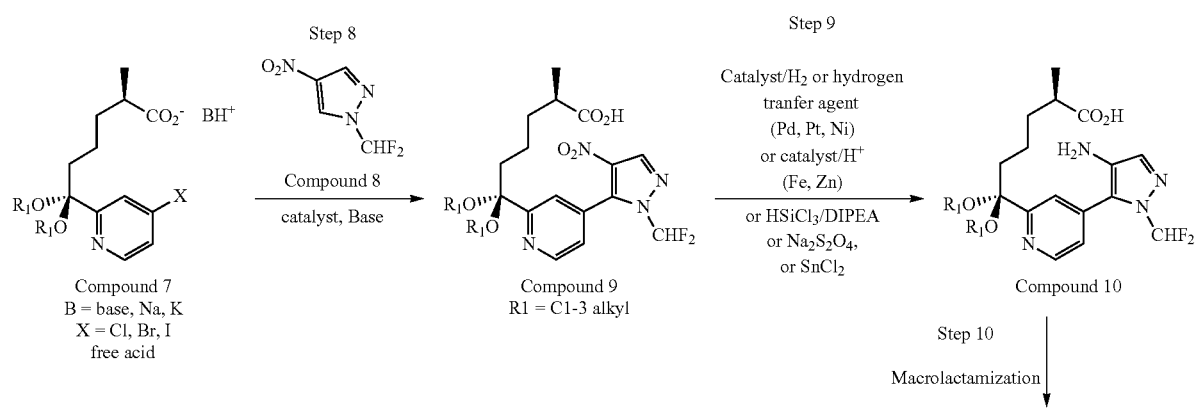
Compound 7
B = base, Na, K
X = Cl, Br, I
free acid
Compound 8
Compound 9
R1 = C1-3 alkyl
Compound 10
Step 10
Macrolactamization

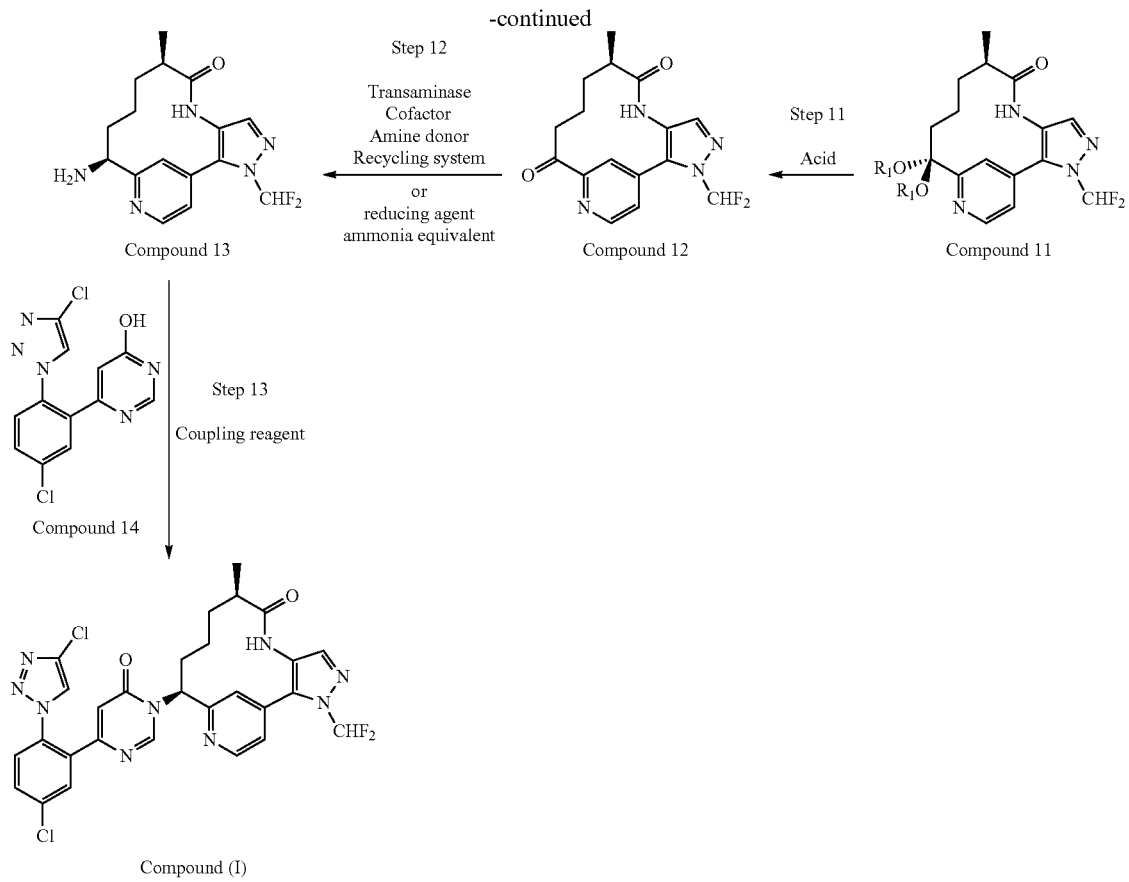

Each step of the preparation method illustrated in the above Schemes will now be described in more detail.

Step 1

The starting materials for this process are Compound 1 and Compound 2. For those embodiments in which the starting materials are prepared according to literature methods, the starting materials are preferably purified prior to reaction. Compound 1 and 2 are being reacted under basic condition in an adequate solvent to form compound 3. Alkoxide bases such as methoxide, ethoxide, tert-butoxide, amylate, tert-amylate, with counter cations such as $Li^+$, $Na^+$, and $K^+$ are suitable.

Examples of suitable solvents include, but are not limited to, polar aprotic solvents such as dimethyl formamide, dimethyl sulfoxide, and N-methylpyrrolidinone; etheral solvents such tetrahydrofuran (THF), 2-methyl tetrahydrofuran (2-MeTHF), methyl t-butyl ether (MTBE), diethoxymethane, and (CPME); hydrocarbons such as benzene, toluene, hexanes, and heptane; halogenated solvents such as dichloromethane and 1,2-dichloroethane; acetates such as ethyl acetate, isopropyl acetate, and butyl acetate, and other solvents such as acetonitrile, methyl vinyl ketone, N,N-dimethylacetamide; polar aprotic solvent such as and mixtures thereof. Preferred solvents include etheral solvents such tetrahydrofuran, 2-methyl tetrahydrofuran, and diethoxymethane.

The reaction may be carried out from about −78° C. to about 0° C. Preferably, the reaction is carried out from about −50° C. to about −20° C.

Step 2

Compound 3 is then subjected to a retro-Claisen reaction to yield compound 4 under acidic conditions, or aqueous acidic condition. Suitable acids include, but not limited to formic acid, acetic acid, benzenesulfonic acid (BSA), nitric acid, perchloric acid, methanesulfonic acid (MSA), trifluoroacetic acid (TFA), citric acid, hydrochloric acid (HCl), sulfuric acid ($H_2SO_4$), and phosphoric acid ($H_3PO_4$). Preferably, the acid is MSA.

The reaction temperature may be varied over a relatively wide range. The reaction is generally carried out at temperatures from 0° C. to 80° C. Preferably, the reaction is carried out from about 20° C. to about 65° C.

Step 3

Compound 4 is then transformed into its corresponding ester and ketal using an alcoholic solvent, an acid catalyst, optionally a drying agent, in the presence of tri alkyl orthoformate. In some embodiments, the alcoholic solvent is a $C_{1-6}$ alcoholic solvent such as methanol, ethanol, propanol butanol, pentanol, and hexanol. The acid catalyst may be selected from HCl, trimethyl silyl chloride (TMSCl), pyridine p-toluene sulfonic acid (PPTS), p-toluene sulfonic acid (PTSA), the drying agent may be needed and could be selected from $Na_2SO_4$ and $MgSO_4$, and the tri alkyl orthoformate may be selected but not limited to, from trimethyl orthoformate (TMOF) and triethyl orthoformate (TEOF).

Step 4

The ester in compound 5 is then hydrolyzed under basic conditions in the presence of water and, a suitable, organic solvent, stable under basic conditions, such as toluene, NMP. Suitable base are hydroxides, with $Li^+$, $Na^+$, $K^+$, $Cs^+$ or NH4+ as counter cations. A non-limiting example of the hydroxides with counter anions are KOH, NaOH, and LiOH.

Step 5

The carboxylic acid in Compound 6 is further reacted with an activating agent to form an activated species which is directly reacted with a chiral auxiliary to form compound 6a in the presence of a base. Typical activating agent are acyl chloride (such as pivaloyl chloride, iso-propoyl chloride, acid anhydride (such as pivalic anhydride, of isopropylanhydride) or reagent such as oxalyl chloride and sulfonyl chloride.

The chiral auxiliary includes, but not limited to, oxazolidinone, 8-phenylmenthol, trans-phenylcyclohexanone, camphorsultam, pseudoephedrine (R,R) or (S,S), or pseudoephenamide (R,R) or (S,S), alkyl thiazolidine-2-thione derivatives or N—(-3-hydroxy-4,7,7-trimethylbicyclo[2.2.1]heptan-2-yl)-N-phenylbenzenesulfonamide. In one embodiment, the chiral auxiliary is an oxazolidinone selected from

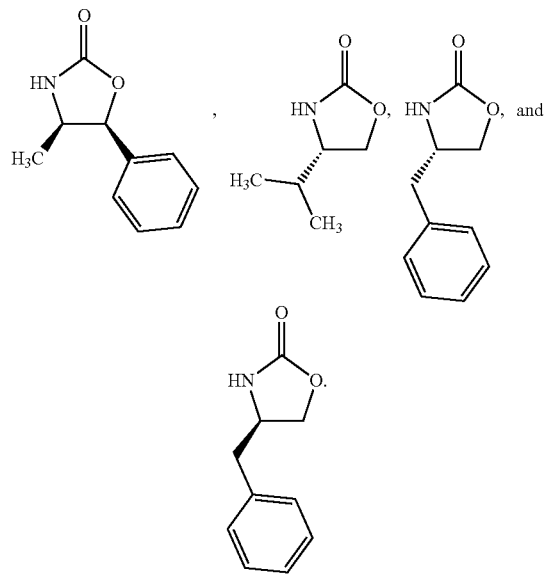

The base may be selected from, for example, DIPEA, TEA, LDA, n-BuLi, sec-BuLi, or tert-buLi, potassium tert-butoxidein an adequate solvent, in the presence or not of an inorganic salt such as LiCl.

Step 6

Compound 6a is alkylated to form Compound 6b using an alkylating agent and a strong base. Non-limiting example of the activating agent includes an alkyl halide, dialkyl sulfate, trialkyloxonium tetrafluoroborate. Preferably, the alkylating agent is methyl halide such as MeI. Suitable bases are NaHMDS, LiHMDS, KHMDS, LDA. A solvent can be chosen from an etheral solvent (THF, 2-Me-THF, MTBE, CPME), aromatic solvent (toluene) or polar aprotic solvent, or a combination of them. The chiral auxiliary is then removed to produce Compound 7, under basic condition, using hydroxide base such as LiOH, NaOH, and KOH.

Step 7

Compound 7 is isolated as an amine base, or an alkaline salt of Na or K in a desirable solvent. Suitable bases are dibenzylamine, DABCO, dicyclohexylamine, ethanolamine, diethanolamine, imidazole, arginine, lysine, tromethamine, alanine, NaOH, KOH, LiOH. Suitable solvents are etheral solvent (THF, 2-Me-THF, MTBE, CPME), aromatic solvent (toluene), ketone solvent (acetone, MIBK, MEK) or ester solvent (EtOAc, PrOAc), acetonitrile, and alcohol solvent (MeOH, EtOH, IPA). Alternatively, Compound 7 can be isolated as free acid.

Step 8

Compound 7 is then reacted with Compound 8 in the presence of a metal catalyst and a base to give rise to Compound 9. The metal catalyst can be derived from Pd, Pt, Rh, Ru, Ir, Fe, Ni or Cu. Ligands such as phosphines (i.e., CX-A, XPhos, SPhos, Xantphos, DCEPhos) or N-heterocyclic carbenes (i.e., IMes, Ipr) may assist the reaction. Suitable bases include organic bases (i.e., Et3N, DIPEA), inorganic bases (i.e., KOPiv, KOAc, K2CO3), or bases derived from an inorganic base and a carboxylic acid (i.e., K2CO3/PivOH, Cs2CO3/PivOH, K2CO3/PhCO2H). Suitable solvents are etheral solvents (i.e., THF, 2-Me-THF, MTBE, CPME), aromatic solvents (i.e., toluene, benzene), or polar aprotic solvents (i.e., DMF, DMAc, NMP).

Step 9

Compound 9 is then subjected to a nitro reduction step using a metal catalyst, such as Pd Pt, Rh on support such as charcoal, aluminum oxide, in the presence of hydrogen gas or a hydrogen transfer reagent such as ammonium or sodium formate in an etheral solvent or alcohol solvent to form compound 10. Compound 9 can also be subjected to HSiCl3/DIPEA, SnCl2 or Na2S2O4 to produce compound 10.

Step 10

Compound 10 is then subjected to a macrolactamization step using a suitable carboxyl activating agent, a base in an adequate solvent. Appropriate coupling agents are any of the well-known coupling agents for coupling an amine to an acid to form an amide. Non-limiting examples of the coupling reagents include PyBOP, HATU/HOBt, EDAC, oxalyl chloride, acid anhydride such as pivalic anhydride, acid chloride such as pivalic chloride, or activating agent such as DPPCL, DMC or TCFH. Suitable solvent are usually etheral solvent (THF, 2-Me-THF, MTBE, CPME), aromatic solvent (toluene).

Step 11

In Step 11, the ketone functionality in Compound 11 is unmasked under aqueous acidic condition to provide compound 12. Non-limiting examples of acids include HCl, HBr, and TFA.

Step 12

Compound 12 then undergoes a reductive amination step to provide compound 13. This transformation can be achieved using a reducing agent such as BH3, NaBH3CN, Pd/C, Pt/C in the presence of an amine donor such as ammonia or ammonium salt like ammonium chloride, a hydrogen transfer salt, such as ammonium formate or hydrogen gas if Pd/C or Pt/C is used.

Reductive amination can also be achieved using a transaminase enzyme in the presence of an amine source such as isopropyl amine, alanine, 3-aminobutyric acid, and methylbenzylamine, and in the presence of a cofactor such as PLP. For the later, the preferred solvent is aqueous DMSO. Different recycling systems such as transaminase/lactate dehydrogenase/glucose dehydrogenase and transaminase/amino acid dehydrogenase/formate dehydrogenase can be used. Non-limiting examples of transaminase are ATA-113, ATA-200, ATA-237, ATA-251, ATA-254, ATA-256, and ATA-260.

The transaminase for use in the processes of the present disclosure generally comprise an amino acid sequence having at least 80%, 85%, 86%, 87%, 88%, 89%, 90%, 91%, 92%, 93%, 94%, 95%, 96%, 97%, 98%, 99%, or more identity to a reference amino acid sequence selected from any one of ATA-113, ATA-200, ATA-237, ATA-251, ATA-254, ATA-256, and ATA-260. In some embodiments, the transaminase is an engineered transaminase polypeptide comprising an amino acid sequence that has one or more amino acid residue differences as compared to a reference sequence (e.g., ATA-113, ATA-200, ATA-237, ATA-251, ATA-254, ATA-256, and ATA-260). In some embodiments, the polynucleotide capable of hybridizing under highly stringent conditions encodes a transaminase polypeptide that has the percent identity described above and one or more residue differences as compared to a reference sequence (e.g., ATA-113, ATA-200, ATA-237, ATA-251, ATA-254, ATA-256, and ATA-260).

In the processes described herein, the transaminase uses an amino donor to form the product compounds. In some embodiments, the amino donor in the reaction condition comprises a compound selected from isopropylamine (also referred to herein as "IPM") or any other suitable amino donor for the reaction of interest. In some embodiments, the amino donor is IPM.

Suitable reaction conditions for the processes also typically comprise the presence of a cofactor in the reaction mixture. Because the transaminase typically uses members of the vitamin $B_6$ family, the reaction condition can comprise a cofactor selected from pyridoxal-5'-phosphate (also known as pyridoxal-phosphate, PLP, P5P), pyridoxine (PN), pyridoxal (PL), pyridoxamine (PM), and their phosphorylated counterparts; pyridoxine phosphate (PNP), and pyridoxamine phosphate (PMP). In some embodiments, the suitable reaction conditions can comprise the presence of a cofactor selected from PLP, PN, PL, PM, PNP, and PMP. In some embodiments, the cofactor is PLP.

Step 13

Compound 13 is finally coupled with compound 14 to produce compound (I), as described in WO 2015/116886.

In the process above, additional steps can be employed among Steps 1-13. In addition, different synthesis processes may be employed to prepare key intermediates in Schemes 1 and 2. Scheme 3 shows a different process for preparing a specific example of Compound 7 (Scheme 1) as Compound 21.

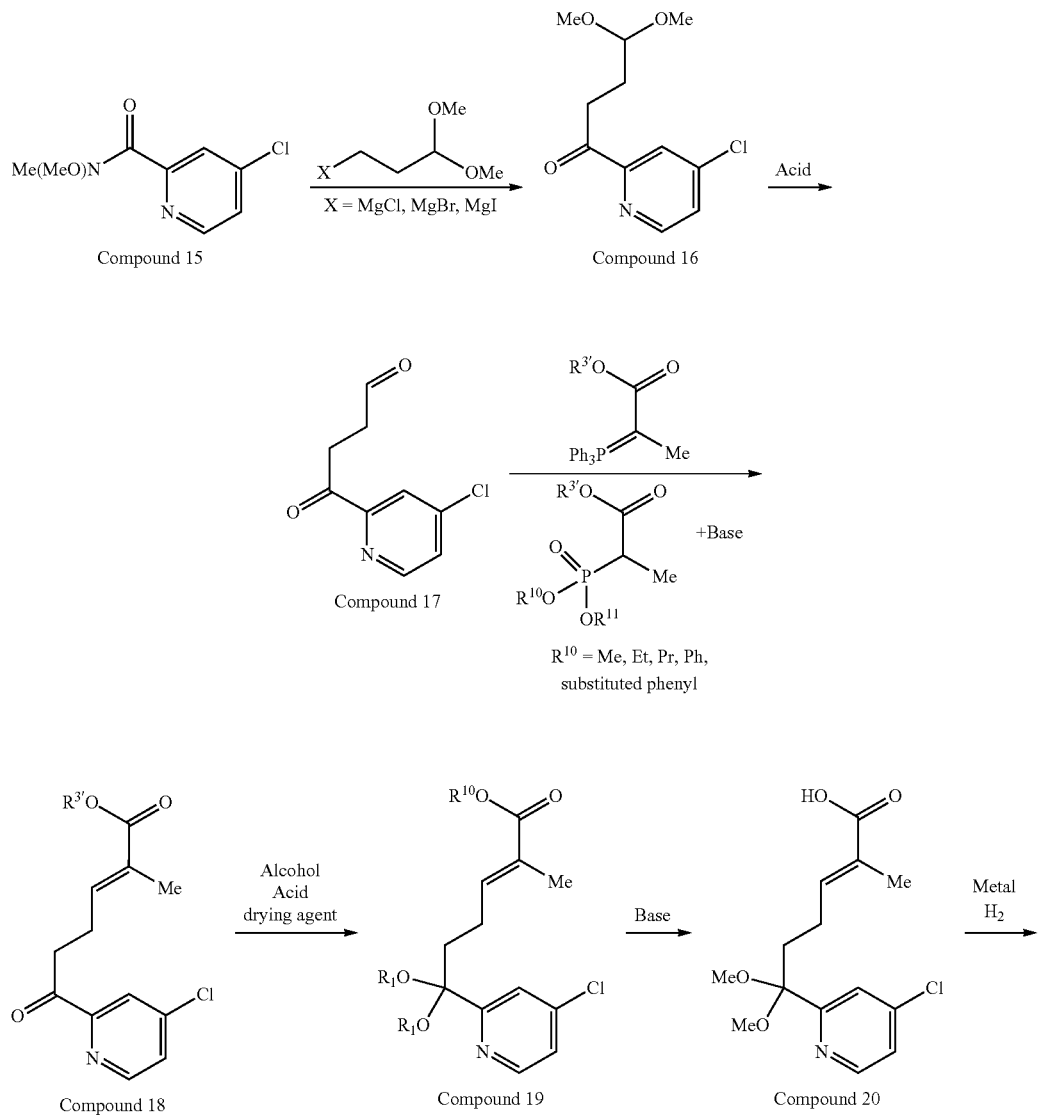

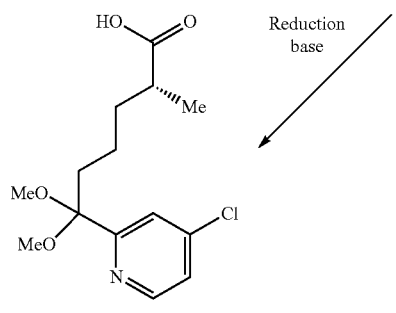

Compound 21

Compound 16 can be formed by coupling compound 15 with 3-chloro-1,1-dimethoxypropane, 3-bromo-1,1-dimethoxypropane or 3-iodo-1,1-dimethoxypropane in the presence of a metal, such as Mg and in the presence of an initiator such as $I_2$, in an adequate solvent such as THF. The subsequent ketal hydrolysis to provide Compound 17 utilizes organic acid such as TFA, MSA, BSA, PTSA, PPTS, or inorganic acid such as HCl, HBr in the presence of water and an adequate solvent. The aldehyde in compound 17 is then reacted with a triphenyl phosphonium ylide such as methyl 2-(triphenyl-15-phosphaneylidene)propanoate, or ethyl 2-(triphenyl-15-phosphaneylidene)propanoate, or alternatively is reacted with a phosphonate derivative such as methyl 2-(diethoxyphosphoryl)propanoate or ethyl 2-(diethoxyphosphoryl)propanoate in the presence of a base, such as NaH or KOtBu, in an adequate solvent to yield to compound 18. The ketone in compound 18 is then protected as its corresponding ketal compound 19 using an alcoholic solvent such as $C_{1-6}$ alcohol, and acid as catalyst such as HCl, trimethylsilyl chloride (TMSCl), pyridine p-toluenesulfonic acid (PPTS), p-toluenesulfonic acid PTSA, and optionally a drying agent, such as $Na_2SO_4$, $MgSO_4$, trimethyl orthoformate (TMOF) or triethyl orthoformate (TEOF). The ester is then hydrolyzed to compound 20 under basic condition in the presence of water. Suitable base are hydroxides, with $Li^+$, $Na^+$, $K^+$, $Cs^+$, $NH_4^+$ as counter cation. Finally, the olefin in compound 20 is reduced to produce Compound 21 utilizing metal catalysis in the presence of $H_2$. The metal is preferably Ru or Rh. The induction of chirality at the methyl carbon center is introduced by the use of an adequate chiral ligand. Alternatively, compound 19 can be reduced by treatment of an ene reductase enzyme and the ester hydrolyzed under basic conditions.

Compound 19 can be prepared by alternative condensation (Scheme 4).

Scheme 4

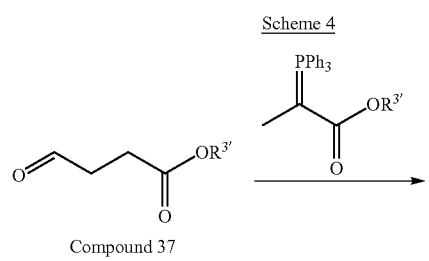

Compound 37

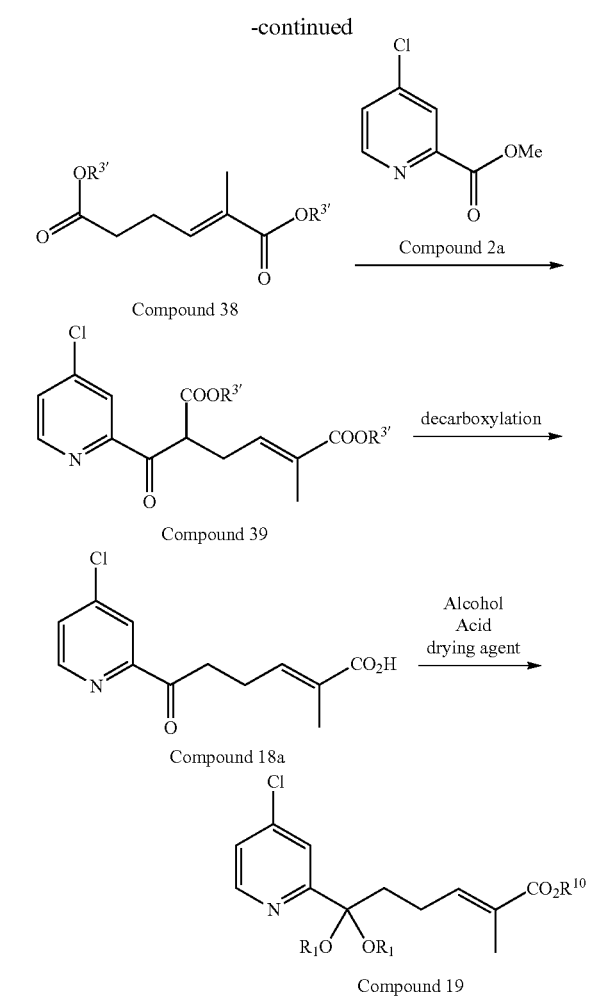

Compound 38 can be formed by coupling of the aldehyde 37 with the triphenyl phosphonium ylide such as methyl 2-(triphenyl-15-phosphaneylidene)propanoate, or ethyl 2-(triphenyl-15-phosphaneylidene)propanoate, or alternatively is reacted with a phosphonate derivative such as methyl 2-(diethoxyphosphoryl)propanoate or ethyl 2-(diethoxyphosphoryl)propanoate in the presence of a base, such as NaH or KOtBu, in an adequate solvent to yield to Compound 38. The obtained bis ester 38 is reacted with Compound 2 having the structure of Compound 2a in presence of base such as LiHMDS, LDA, tBuOK in an adequate solvent to yield to Compound 39. This compound is further decarboxylated in presence of an acid such as HCl, MSA, $H_3PO_4$ in an adequate solvent to yield to Compound 18a which is later converted to Compound 19 as described above.

In another embodiment, Compound 21 can be prepared starting from cyclopentane ester derivative (Scheme 5).

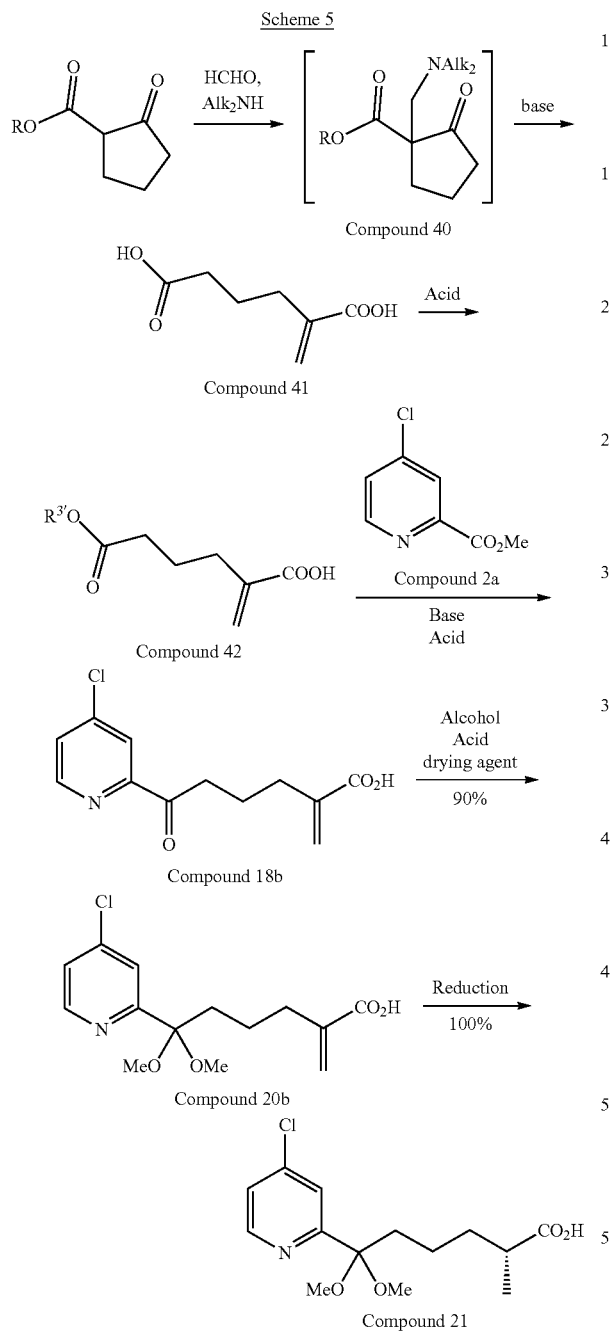

Compound 40 is formed by coupling of cyclopentane ester derivative with formaldehyde and a dialkyl amine. Further treatment in basic conditions provides the di acid derivative Compound 41. After esterification to form Compound 42, coupling with Compound 2a and acidic treatment, the acrylate derivate Compound 18b is obtained. The ketone in Compound 18b is then protected as its corresponding ketal using an alcoholic solvent such as a $C_{1-6}$ alcohol, an acid as catalyst such as HCl, trimethylsilyl chloride (TMSCl), pyridine p-toluenesulfonic acid (PPTS), p-toluenesulfonic acid PTSA, and optionally a drying agent, such as $Na_2SO_4$, $MgSO_4$, trimethyl orthoformate (TMOF) or triethyl orthoformate (TEOF). The ester is then hydrolyzed to Compound 20b under basic condition in the presence of water. Suitable bases include hydroxides, with Li+, Na+, K+, Cs+, NH4+ as counter cation or the free carboxylic acid. Finally, the olefin in Compound 20b is reduced to produce Compound 21 utilizing metal catalysis in the presence of $H_2$. The metal is preferably Ru or Rh. The induction of chirality at the methyl carbon center is introduced by the use of an adequate chiral ligand. Alternatively, the desired enantiomer can be obtained by treatment with an ene reductase enzyme.

In another embodiment, a specific example of Compound 7 (Scheme 1), Compound 27 (Scheme 7), which may be prepared via an enzymatic resolution approach as shown in reaction schemes 6 and 7.

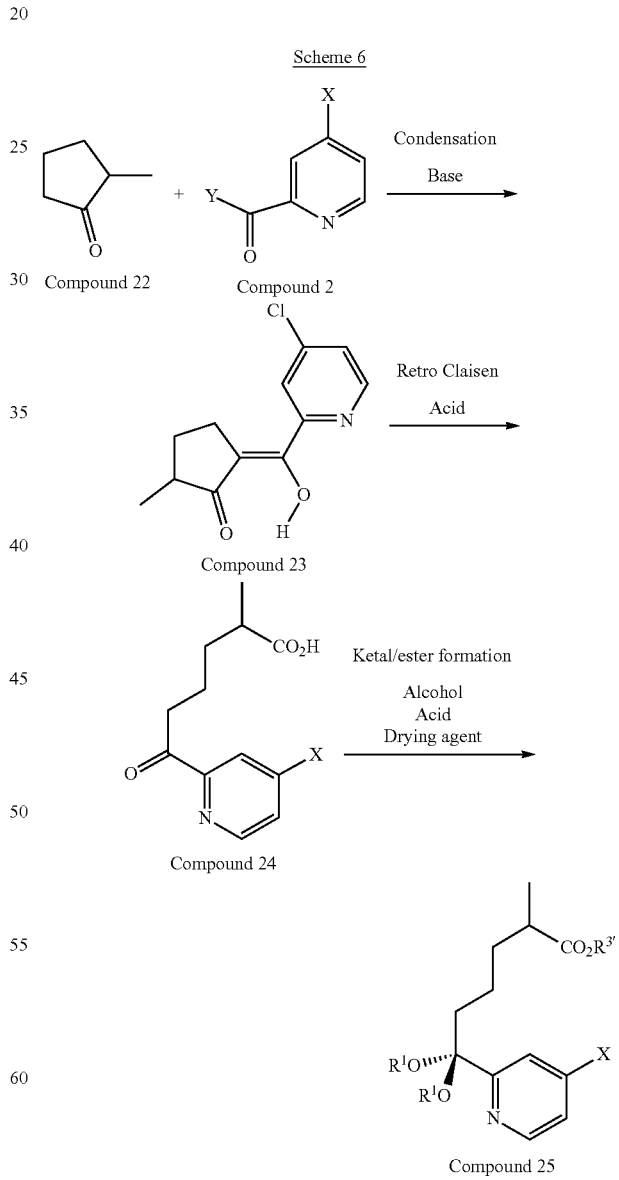

Compound 22 and 2 are being reacted under basic condition in an adequate solvent to form compound 23. Bases like alkoxide (methoxide, ethoxide, tert-butoxide, amylate, tert-amylate) with Li+, Na+, K+ as counter cations are suitable along with solvent such as an etheral solvent (THF, 2-MeTHF, MTBE, CPME), aromatic solvent (toluene) or dipolar aprotic solvent. Compound 24 is obtained from a retro-Claisen reaction of compound 23 under acidic condition, or aqueous acidic condition. Suitable acids are, but not limited to, H$_2$SO$_4$, MSA, BSA, nitric acid, TFA or perchloric acid.

Compound 24 is then transformed into its corresponding ester and ketal Compound 25 using an alcoholic solvent (C1-6 alcohol), and acid as catalyst such as, but not limited to, HCl, trimethyl silyl chloride (TMSCl), pyridine p-toluene sulfonic acid (PPTS), p-toluene sulfonic acid PTSA, and optionally a drying agent, such as Na$_2$SO$_4$, MgSO$_4$, and a trialkylorthoformate, such as trimethyl orthoformate (TMOF) or triethyl orthoformate (TEOF).

Compound 25 is then subjected to enzymatic resolution as shown in Scheme 7.

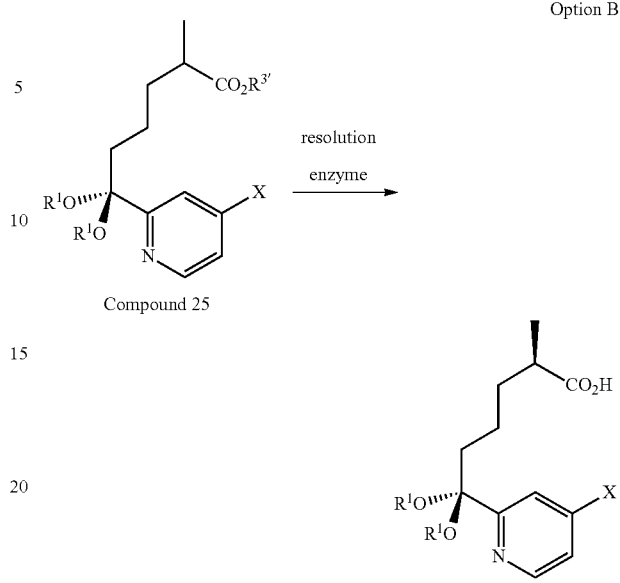

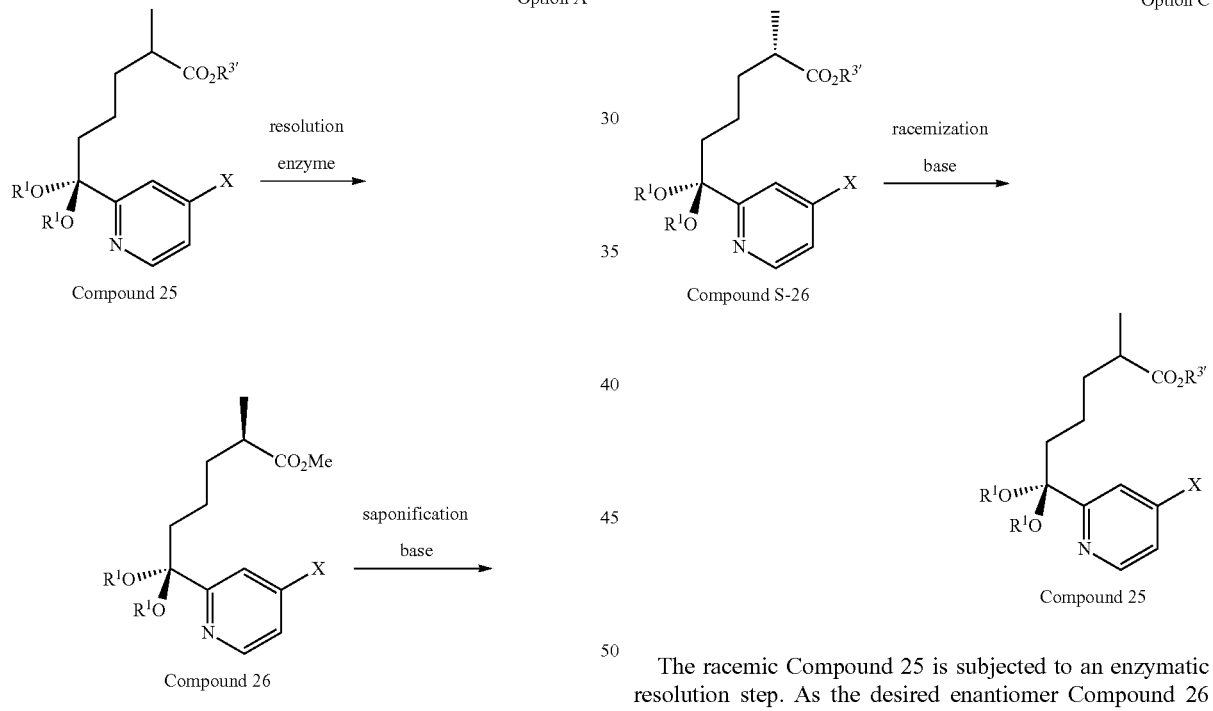

The racemic Compound 25 is subjected to an enzymatic resolution step. As the desired enantiomer Compound 26 remains unreacted, the undesired enantiomer in the racemic mixture Compound 25 is getting hydrolyzed. Then Compound 26 is hydrolyzed using an aqueous base such as NaOH to afford Compound 27. Preferably, the hydrolytic enzyme is Lipase MH Amano 10 SD, which shows good selectivity (>90% enantiomeric excess).

In Option B, the racemic Compound 25 is subjected to an enzymatic resolution step. As the undesired enantiomer remains unreacted to a degree, the desired enantiomer in the racemic mixture Compound 25 is getting hydrolyzed to form Compound 27.

In Option C, The unreacted undesired enantiomer Compound S-26 generated in Option B is racemized in presence of base to form Compound 25 which can be used as starting material in Option A or Option B above.

In another embodiment, intermediate Compound 10 is prepared by a process as shown in Scheme 8, which is different from that in Scheme 1.

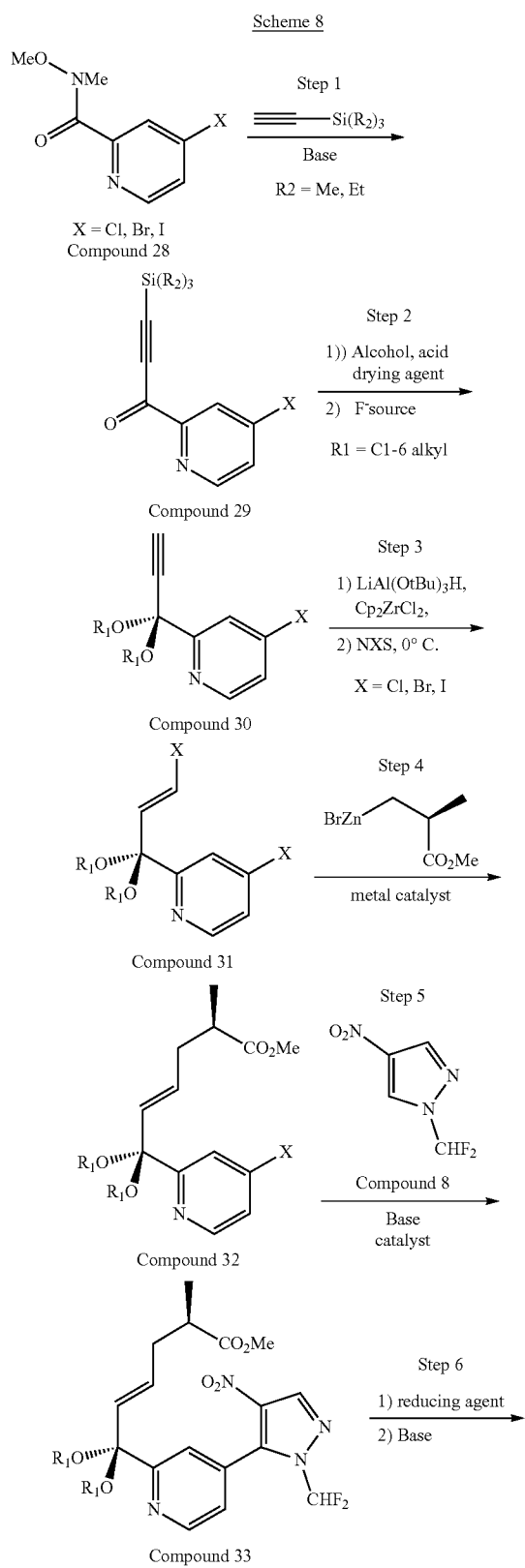

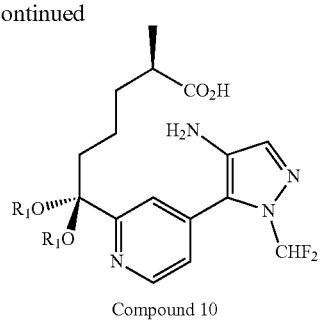

Compound 10

Step 1

Compound 28 is coupled with a silyl protected acetylene in a strong base and suitable solvent to give rise to compound 29. The base may be a strong lithiated base such as an alkyl lithiated base or aryl lithiated base. Non-limiting examples of the alkyl and aryl lithiated bases are methyl lithium, n-butyl lithium, sec-butyl lithium, tert-butyl lithium, and phenyl lithium. The solvent may be an etheral solvent such as THF.

Step 2 The ketone moiety is then protected as its corresponding ketal using an alcoholic solvent ($C_{1-6}$ alcohol), and acid as catalyst such as HCl, trimethyl silyl chloride (TMSCl), pyridine p-toluene sulfonic acid (PPTS), p-toluene sulfonic acid PTSA, and optionally a drying agent, such as $Na_2SO_4$, $MgSO_4$, and a trialkyl orthoformate, such as trimethyl orthoformate (TMOF) or triethyl orthoformate (TEOF). The protecting silylated group is then deprotected using fluorine source such as TBAF, HF.TEA, HF in an adequate solvent such as THF, 2-MeTHF to yield Compound 30.

Step 3

The triple bond in Compound 30 is then derivatized to its corresponding vinyl halide, Compound 31, in two stages using $LiAl(OtBu)_3H/Cp_2ZrCl_2$, followed by use of an halide donor such as N-chlorosuccinimide, N-bromosuccinimide or N-iodosuccinimide.

Step 4

Compound 31 is then subjected to a metal catalyzed cross coupling with commercially available (S)-(−)-3-methoxy-2-methyl-3-oxopropylzinc bromide to give rise to Compound 32. Non-limiting examples of a metal catalyst include a Pd(II) salt, such as $PdCl_2$, $Pd(OAc)_2$, or pre-ligated metal such as 1,1'-bis(di-tert-butylphosphino)ferrocene palladium dichloride.

Step 5

Compound 32 is then reacted with Compound 8 in the presence of a metal catalyst and a base to give rise to Compound 33. The metal catalyst can be derived from Pd, Pt, Rh, Ru, Ir, Fe, Ni or Cu. Ligands such as phosphines (i.e., CX-A, XPhos, SPhos, Xantphos, DCEPhos) or N-heterocyclic carbenes (i.e., IMes, Ipr) may assist the reaction. Suitable bases include organic bases (i.e., $Et_3N$, DIPEA), inorganic bases (i.e., KOPiv, KOAc, $K_2CO_3$), or bases derived from an inorganic base and a carboxylic acid (i.e., $K_2CO_3$/PivOH, $Cs_2CO_3$/PivOH, $K_2CO_3$/$PhCO_2H$). Suitable solvents are etheral solvents (i.e., THF, 2-Me-THF, MTBE, CPME), aromatic solvents (i.e., toluene, benzene), or polar aprotic solvents (i.e., DMF, DMAc, NMP).

Step 6

Compound 33 is then subjected to reductive condition to enable the reduction of the double bond and the nitro functional group and then to hydrolyze the methyl ester to get to Compound 10. The reduction can be effective using metal such as Pd or Pt in the presence of hydrogen gas, in a protic solvent such as MeOH, EtOH, IPA. The ester hydrolysis occurs by treating the methyl ester with a hydroxide base, such as LiOH, NaOH, KOH in the presence of water or water and a miscible organic solvent.

Scheme 9

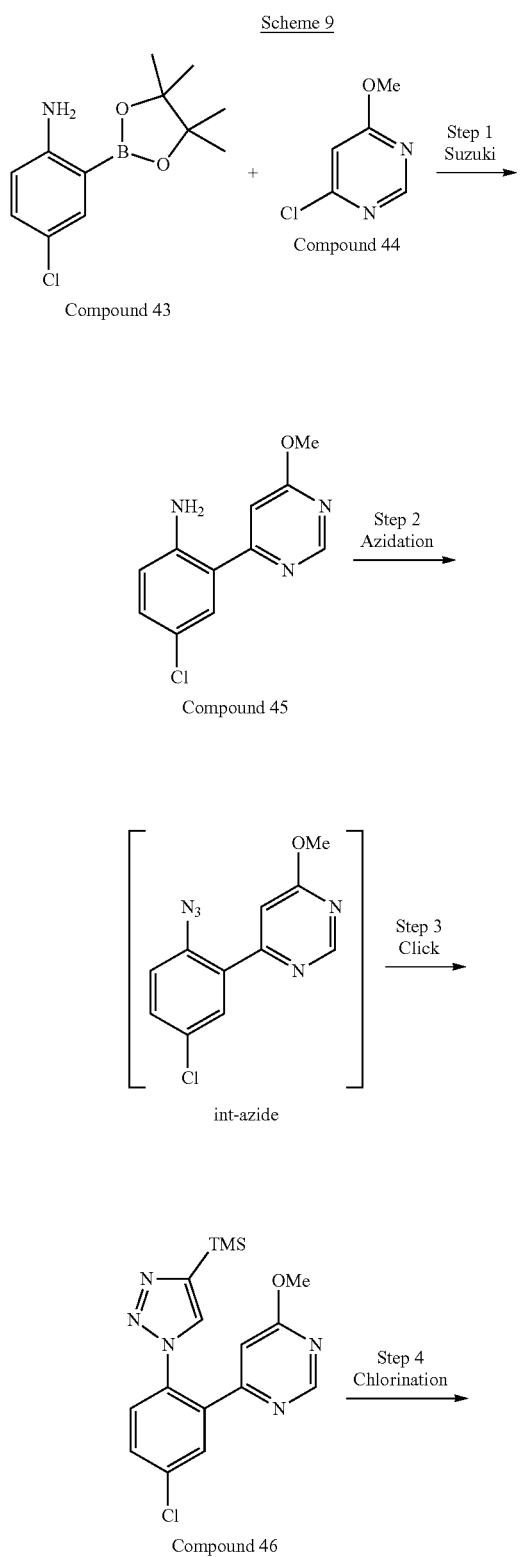

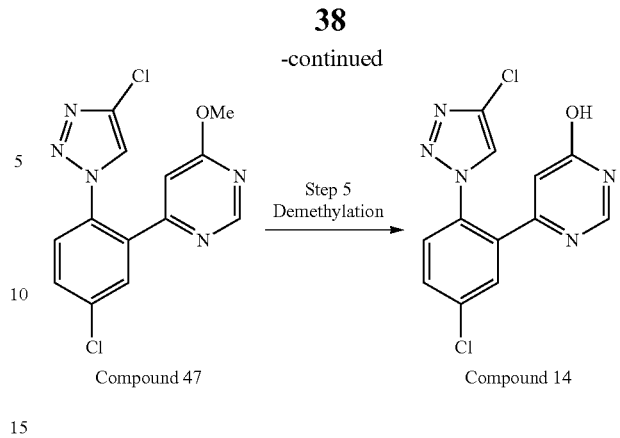

Step 1

Compound 45 can be synthesized from Compound 43 and Compound 44 under suitable Suzuki coupling conditions, e.g., in the presence of an appropriate level of a palladium catalyst, such as Pd(PPh$_3$)$_4$, Pd(OAc)$_2$ or Pd(dppf)Cl$_2$-DCM complex, in a suitable solvent, such as methanol, DMF, or acetonitrile.

Steps 2 and 3

Compound 46 can be produced by azidation and subsequent Click chemistry with the appropriate acetylenic compound. Compound 45 is subjected to azidation conditions, e.g., TMSN$_3$/tBuONO, to afford the intermediate azide, which is then treated with trimethylsilylacetylene in the presence of a copper(I) catalyst, e.g., CuOAc or copper(I) iodide, to produce triazole Compound 46.

Step 4

Compound 47 can be produced from silyl Compound 46 by reaction with 1,3-dichloro-5,5-dimethylhydantoin in a suitable solvent. Suitable solvents include polar aprotic solvents such as THF or DMF.

Step 5

Compound 14 can be produced from Compound 47 by reaction in hydrochloric acid, e.g., concentrated hydrochloric acid.

In another embodiment, the present invention provides a compound of formula (II):

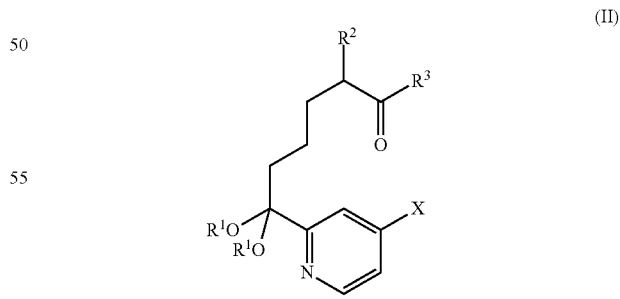

in the form of a base or salt, wherein
---- is an optional bond;
R$^1$ is C$_{1-6}$ alkyl;
R$^2$ is C$_{1-3}$ alkyl; alkenyl
R$^3$ is selected from OH, OC$_{1-6}$ alkyl

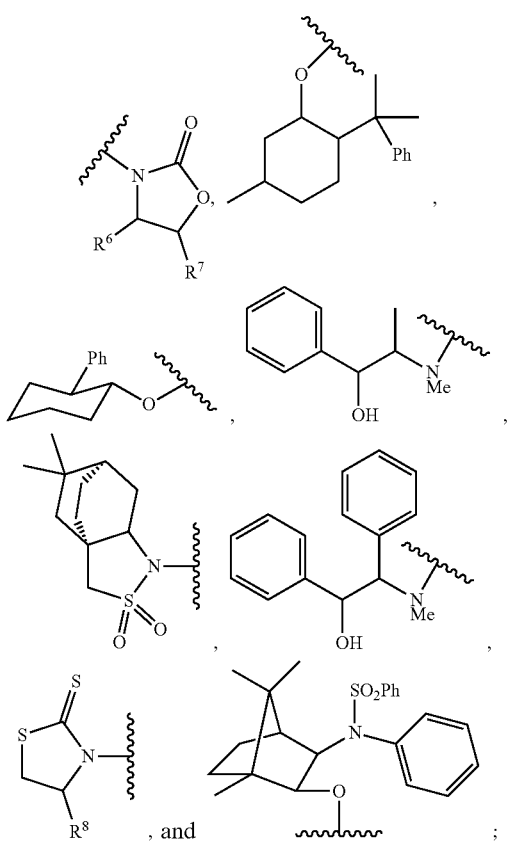

wherein

R[6] is selected from C$_{1-3}$ alkyl, phenyl, and benzyl;
R[7] is selected from H and phenyl;
R[8] is selected from C$_{1-3}$ alkyl, phenyl, and benzyl; and
X is selected from F, Cl, Br and I.

In another embodiment, the present invention provides a compound selected from the group consisting of

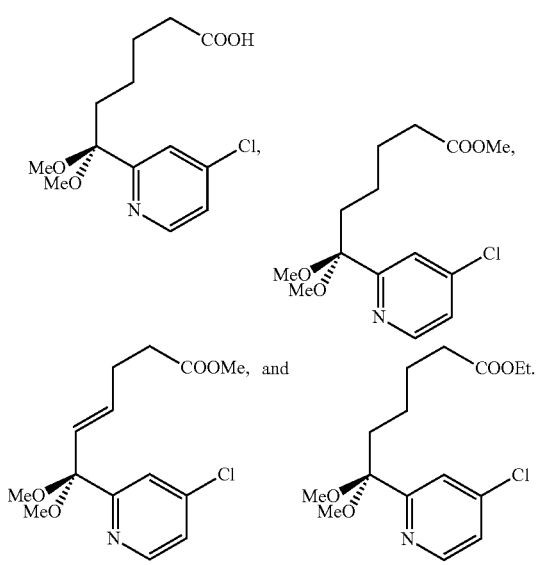

In another embodiment, the present invention provides a compound having the structure selected from the group consisting of

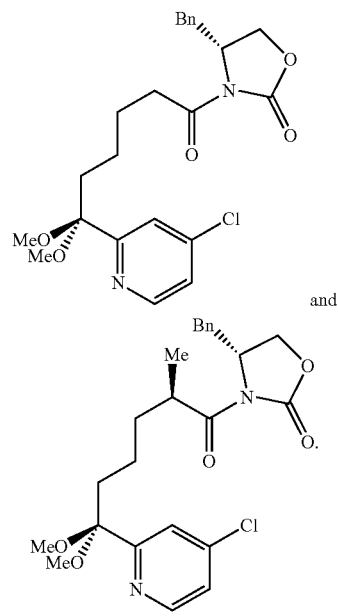

In another embodiment, the present invention provides a compound selected from the group consisting of

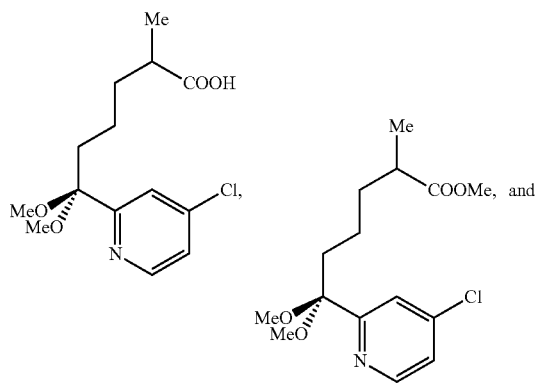

In another embodiment, the present invention provides a compound of Formula (III):

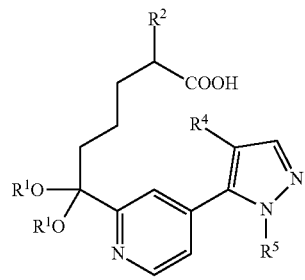

(III)

wherein
$R^1$ is $C_{1-6}$ alkyl;
$R^2$ is $C_{1-3}$ alkyl;
$R^4$ is selected from $NO_2$, $N=O$, $NHOH$, and $NH_2$; and
$R^5$ is selected from $CHF_2$, $CD_3$, and $CH_3$.

In another embodiment, the present invention provides a compound selected from the group consisting of

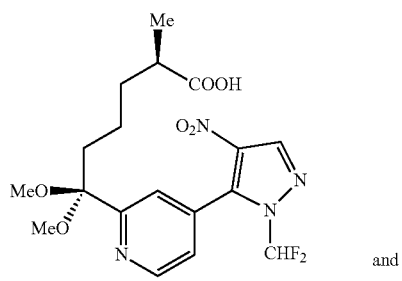

and

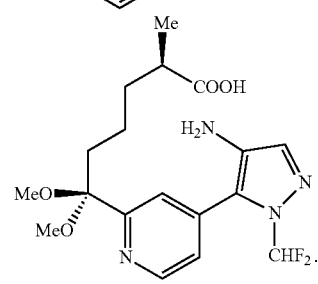

In another embodiment, the present invention provides a compound of Formula (IV):

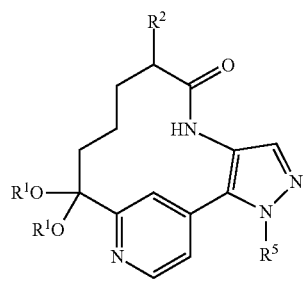

(IV)

wherein
$R^1$ is $C_{1-6}$ alkyl;
$R^2$ is $C_{1-3}$ alkyl; and
$R^5$ is selected from $CHF_2$, $CD_3$, and $CH_3$.

In another embodiment, the present invention provides a compound selected from the group consisting of

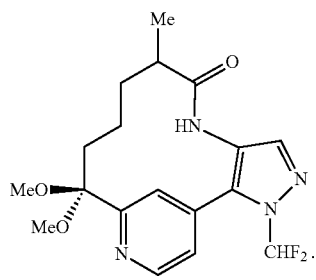

In another embodiment, the present invention provides a compound of Formula (V):

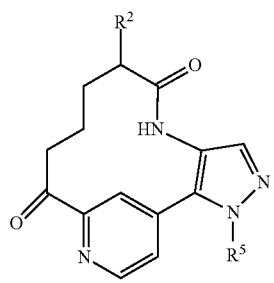

(V)

wherein
$R^2$ is $C_{1-3}$ alkyl; and
$R^5$ is selected from $CHF_2$, $CD_3$, and $CH_3$.

In another embodiment, the present invention provides a compound

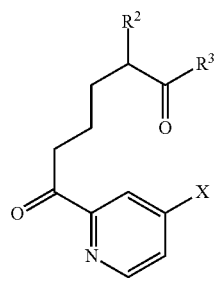

In another embodiment, the present invention provides a compound of Formula (VI):

(VI)

wherein
$R^2$ is $C_{1-3}$ alkyl;
$R^3$ is selected from OH, $OC_{1-6}$ alkyl,

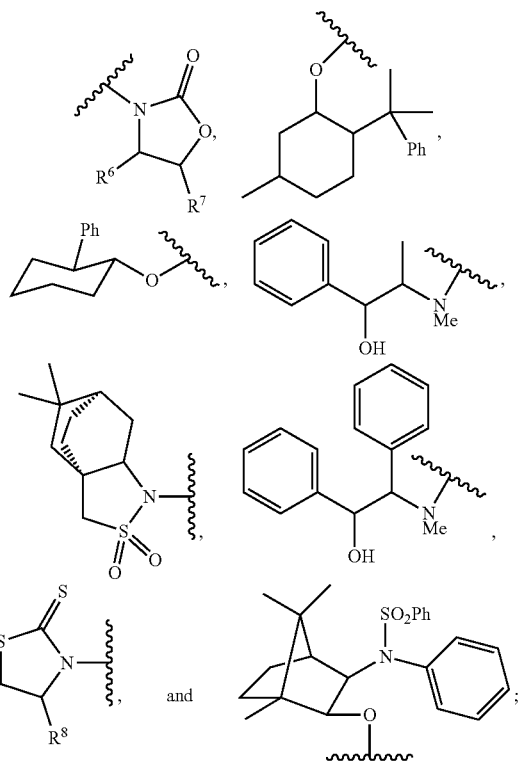

wherein
R⁶ is selected from $C_{1-3}$ alkyl, phenyl, and benzyl;
R⁷ is selected from H and phenyl;
R⁸ is selected from $C_{1-3}$ alkyl, phenyl, and benzyl; and
X is selected from F, Cl, Br and I.

In another embodiment, the present invention provides a compound having the structure.

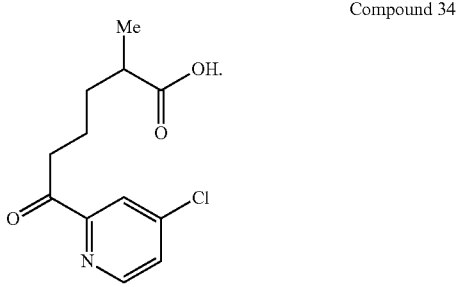 [SMILES: CC(CCCC(=O)c1cc(Cl)ccn1)C(=O)O]

Compound 34

EXAMPLES

With the aim to better illustrate the present invention the following examples are given. All reactions were performed under a nitrogen atmosphere using anhydrous techniques unless otherwise noted. Reagents were used as received from the vendors, unless otherwise noted. Quoted yields are for isolated material, and have not been corrected for moisture content. Reactions were monitored by normal or reverse phase HPLC on a Shimadzu system using $CH_3CN/H_2O/$ MeOH as the mobile phase (containing either 0.05% TFA, or 0.1% $NH_4OAc$).

Method A
Chromatographic Conditions

| | |
|---|---|
| Instrument | Shimadzu |
| Column | Waters XSELECT CSH Phenyl-Hexyl 3.5 μm 4.6 × 150 mm |
| Column temperature | 40° C. |
| Flow rate | 1.5 mL/min |
| Injection volume | 10 uL |
| Wave length | 220 nm, 260 nm (used 260 nm for calculations) |
| Mobile Phase A | 0.01M Ammonium acetate in Water-Acetonitrile (95:5) |
| Mobile Phase B | 0.01M Ammonium acetate in Water-Acetonitrile (5:95) |

Gradient

| Time (min) | % A | % B |
|---|---|---|
| 0 | 100 | 0 |
| 6 | 90 | 10 |
| 11 | 10 | 90 |
| 12.5 | 10 | 90 |
| 12.6 | 100 | 0 |
| 15 | 100 | 0 |

Method B
Chromatographic Conditions

| | |
|---|---|
| Instrument | Shimadzu |
| Column | ASCENTIS Express C18 2.7 um 4.6 × 50 mm |
| Column temperature | 25° C. |
| Flow rate | 1.5 mL/min |
| Injection volume | 10 μL |
| Wave length | 254 nm |
| Mobile Phase A | 0.05% TFA in ACN:water (5:95) |
| Mobile Phase B | 0.05% TFA in ACN:water (95:5) |

Gradient

| Time (min) | % A | % B |
|---|---|---|
| 0 | 100 | 0 |
| 10 | 0 | 100 |
| 15 | 100 | 0 |

Method C
Chromatographic Conditions

| | |
|---|---|
| Column | Phenomenex Kinetex XB-C18 2.6 micron, 4.6 × 50 mm |
| Column Temperature | 25° C. |
| Flow Rate | 1.0 mL/min |
| Injection Volume | 5-10 μL |
| Wave Length | 220 nm |
| Mobile Phase A | 0.01M NH4OAc in MeOH:Water (20:80) |
| Mobile Phase B | 0.01M NH4OAc in MeOH:Water:ACN (20:5:75) |

Gradient

| Time (min) | % A | % B |
|---|---|---|
| 1 | 0.0 | 95 | 5 |
| 2 | 5 | 80 | 20 |

-continued

| Time (min) | % A | % B |
|---|---|---|
| 3 | 8 | 80 | 20 |
| 4 | 9 | 60 | 40 |
| 5 | 20 | 0 | 100 |

Method D
Chromatographic Conditions

| | |
|---|---|
| Column | Waters Sunfire 3.5 um 4.6 × 150 mm |
| Column Temperature | 25° C. |
| Flow Rate | 1.0 mL/min |
| Injection Volume | 5-10 μL |
| Wave Length | 220 nm |
| Mobile Phase A | 0.05% TFA in Water:CH3CN (95:5) |
| Mobile Phase B | 0.05% TFA in Water:CH3CN (5:95) |

Gradient

| | Time (min) | % A | % B |
|---|---|---|---|
| 1 | 0.0 | 60 | 40 |
| 2 | 2 | 60 | 40 |
| 3 | 10 | 10 | 90 |
| 4 | 11 | 10 | 90 |

Method F
Chromatographic Conditions

| | |
|---|---|
| Column | Lux Cellulose-3, 4.6 × 150 mm, 3 micron |
| Column Temperature | 25° C. |
| Flow Rate | 0.8 mL/min |
| Injection Volume | 10 μL |
| Wave Length | 220 nm |
| Mobile Phase A | 0.05% TFA in Water:CH3CN (95:5) |
| Mobile Phase B | 0.05% TFA in Water:CH3CN (5:95) |

Gradient:

| | Time (min) | % A | % B |
|---|---|---|---|
| 1 | 0 | 90 | 10 |
| 2 | 15 | 90 | 10 |
| 3 | 16 | 0 | 100 |

Method F
Chromatographic Conditions

| | |
|---|---|
| Column | Ascentis Express C18 2.7 um 4.6 × 150 mm |
| Column Temperature | 35° C. |
| Flow Rate | 0.8 mL/min |
| Injection Volume | 5-10 μL |
| Wave Length | 265 nm |
| Mobile Phase A | 0.05% formic acid in MeOH:Water (20:80) |
| Mobile Phase B | 0.05% formic acid in ACN:MeOH (80:20) |

Gradient:

| | Time (min) | % A | % B |
|---|---|---|---|
| 1 | 0.0 | 90 | 10 |
| 2 | 6 | 60 | 40 |
| 3 | 13 | 60 | 40 |

-continued

| | Time (min) | % A | % B |
|---|---|---|---|
| 4 | 18 | 10 | 90 |
| 5 | 20 | 10 | 90 |
| 6 | 20.1 | 90 | 10 |
| 7 | 24.0 | 90 | 10 |

Method G
Chromatographic Conditions

| | |
|---|---|
| Column | Zorbax Eclipse Plus C8 1.8 um 4.6 × 50 mm |
| Column Temperature | 25° C. |
| Flow Rate | 1.2 mL/min |
| Injection Volume | 5-10 μL |
| Wave Length | 220 nm |
| Mobile Phase A | 0.05% TFA in Water:CH3CN (95:5) |
| Mobile Phase B | 0.05% TFA in Water:CH3CN (5:95) |

Gradient:

| | Time (min) | % A | % B |
|---|---|---|---|
| 1 | 0.0 | 95 | 5 |
| 2 | 2 | 95 | 5 |
| 3 | 6 | 0 | 100 |

Method H
Chromatographic Conditions

| | |
|---|---|
| Column | Chiralpak IG-3, 4.6 × 150 mm, 3 um |
| Column Temperature | 30° C. |
| Flow Rate | 1.0 mL/min |
| Injection Volume | 10 μL |
| Wave Length | 220 nm |
| Mobile Phase A | 0.1% DEA in Heptane |
| Mobile Phase B | 0.1% DEA in IPA |

Gradient:

| | Time (min) | % A | % B |
|---|---|---|---|
| 1 | 0.0 | 90 | 10 |
| 2 | 2 | 90 | 10 |
| 3 | 20 | 60 | 40 |
| 4 | 24 | 60 | 40 |
| 5 | 24.1 | 90 | 10 |

Method 1
Chromatographic Conditions

| | |
|---|---|
| Column | Phenomenex Kinetix C18, 150 × 4.6 mm, 2.6 μm |
| Column Temperature | 30° C. |
| Flow Rate | 1.0 mL/min |
| Injection Volume | 10 μL |
| Wave Length | 270 nm |
| Mobile Phase A | 0.1% TFA in water |
| Mobile Phase B | 0.1% TFA in ACN:water (70:30) |

Gradient:

| Time (min) | % A | % B |
|---|---|---|
| 1 | 0.0 | 90 | 10 |
| 2 | 10 | 70 | 30 |
| 3 | 15 | 60 | 40 |
| 4 | 20 | 50 | 50 |
| 5 | 30 | 50 | 50 |
| 6 | 40 | 10 | 90 |

Method J

Chromatographic Conditions—

| | |
|---|---|
| Column | Waters Zorbax Eclipse Plus C1 81.8 μm 4.6 × 150 mm |
| Column temperature | 25° C. |
| Flow rate | 1.2 mL/min |
| Injection volume | 10 μL |
| Wave length | 228 nm, 258 nm (used 228 nm for conversion calculations) |
| Mobile Phase A | 0.05% TFA in Water-Acetonitrile (95:5) |
| Mobile Phase B | 0.05% TFA in Water-Acetonitrile (5:95) |

Gradient:

| Time (min) | % A | % B |
|---|---|---|
| 1 | 0 | 80 | 20 |
| 2 | 10 | 0 | 100 |

Method K

Chromatographic Conditions—

| | |
|---|---|
| Column | ChiralPak AD-3R 3.0 nm 4.6 × 150 mm |
| Column temperature | 25° C. |
| Flow rate | 0.8 mL/min |
| Injection volume | 10 μL |
| Wave length | 220 nm, 258 nm (used 228/258 nm for calculations) |
| Mobile Phase A | 0.01M Ammonium acetate in Water-Acetonitrile (95:5) |
| Mobile Phase B | 0.01M Ammonium acetate in Water-Acetonitrile (5:95) |

Gradient:

| Time (min) | % A | % B |
|---|---|---|
| 1 | 0 | 60 | 40 |
| 2 | 15 | 60 | 40 |

Method L

Chromatographic Conditions—

| | |
|---|---|
| Column | Phenomenex Lux Cellulose-3 3.0 μm 4.6 × 150 mm |
| Column temperature | 25° C. |
| Flow rate | 0.8 mL/min |
| Injection volume | 10 μL |
| Wave length | 228 nm, 258 nm (used 228 nm for calculations) |
| Mobile Phase A | 0.05% TFA in Water-Acetonitrile (95:5) |
| Mobile Phase B | 0.05% TFA in Water-Acetonitrile (5:95) |

Gradient:

| Time (min) | % A | % B |
|---|---|---|
| 1 | 0 | 90 | 10 |
| 2 | 15 | 90 | 10 |
| 3 | 18 | 0 | 100 |
| 4 | 22 | 0 | 100 |

NMR-spectra were recorded on Bruker DRX-600, DRX-500 or DRX 400 instruments, and are referenced to residual undeuterated solvents. Low resolution mass spectra (LRMS) were recorded on a Water ZQ ES instrument.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "a", "f", "R", "S", "E", and "Z" are stereochemical designations familiar to one skilled in the art.

| | |
|---|---|
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Boc | tert-butyloxycarbonyl |
| AcOH or HOAc | acetic acid |
| AlCl$_3$ | aluminum chloride |
| AIBN | azobisisobutyronitrile |
| BEMP | 2-tert-butylimino-2-diethylamino-1,3-dimethylperhydro-1,3,2-diazaphosphorine |
| BH$_3$ | borane |
| BOP reagent | benzotriazol-1-yloxytris(dimethylamino)phosphonium hexafluorophosphate |
| BSA | Benzenesulfonic acid |
| n-BuOH | n-butanol |
| CBz | carbobenzyloxy |
| CH$_2$Cl$_2$ | dichloromethane |
| CH$_3$CN or ACN | acetonitrile |
| mCPBA or m-CPBA | meta-chloroperbenzoic acid |
| CPME | cyclopentyl methyl ether |
| CPME | cyclopentyl methyl ether |
| Cp$_2$ZrCl$_2$ | di(cyclopentadienyl)zirconium(IV) dichloride |
| Cs$_2$CO$_3$ | cesium carbonate |
| Cu(OAc)$_2$ | copper (II) acetate |
| CX-A | di(1-adamantyl)-n-butylphosphine |
| Cy$_2$NMe | N-cyclohexyl-N-methylcyclohexanamine |
| DABCO | 1,4-diazabicyclo[2.2.2]octane |
| DBU | 1,8-diazabicyclo[5.4.0]undec-7-ene |
| DCE | 1,2-dichloroethane |

| | |
|---|---|
| DCEPhos | bis(2-dicyclohexylphosphinophenyl)ether |
| DCM | dichloromethane |
| DEA | diethylamine |
| DIC or DIPCDI | diisopropylcarbodiimide |
| DIEA, DIPEA or Hunig's base | Diisopropylethylamine |
| DMAc | Dimethyl acetamide |
| DMAP | 4-dimethylaminopyridine |
| DMC | 2-Chloro-4,5-dihydro-1,3-dimethyl-1H-imidazolium chloride |
| DME | 1,2-dimethoxyethane |
| DMF | dimethyl formamide |
| DMSO | dimethyl sulfoxide |
| DPPCl | diphenylphosphinous chloride |
| DuPhos | (+)-1,2-bis((2S,5S)-2,5-diethylphospholano)benzene |
| EDAC | N-(3-Dimethylaminopropyl)-N'-ethylcarbodiimide hydrochloride |
| DCE | 1,2-dichloroethane or ethylenedichloride |
| EDTA | ethylenediaminetetraacetic acid |
| (S,S)-EtDuPhosRh(I) | (+)-1,2-bis((2S,5S)-2,5-diethylphospholano)benzene(1,5-cyclooctadiene)rhodium(I) trifluoromethanesulfonate |
| Et₃N or TEA | triethylamine |
| EtOAc | ethyl acetate |
| Et₂O | diethyl ether |
| EtOH | ethanol |
| Grubbs (II) | (1,3-bis(2,4,6-trimethylphenyl)-2-imidazolidinylidene)dichloro(phenylmethylene)(tricyclohexylphosphine)ruthenium |
| HBr | hydrobromic acid |
| HCl | hydrochloric acid |
| HATU | O-(7-azabenzotriazol-1-yl)-N,N,N',N'-tetramethyluronium hexafluorophosphate |
| HEPES | 4-(2-hydroxyethyl)piperazine-1-ethanesulfonic acid |
| Hex | hexane |
| HOBt or HOBT | 1-hydroxybenzotriazole |
| H₂SO₄ | sulfuric acid |
| IMes | 1,3-bis(2,4,6-trimethylphenyl)imidazol-2-ylidene |
| Ipr | 1,3-bis(2,6-diisopropylphenyl)-1,3-dihydro-2H-imidazol-2-ylidene |
| K₂CO₃ | potassium carbonate |
| KOAc | potassium acetate |
| KOPiv | Potassium pivalate |
| KHMDS | potassium bis(trimethylsilyl)amide |
| K₂HPO₄ | potassium hydrogen phosphate |
| K₃PO₄ | potassium phosphate tribasic |
| LAH | lithium aluminum hydride |
| LDA | Lithium diisopropyl amine |
| LG | leaving group |
| LiAl(OtBu)₃H | lithium aluminum-tri-tert-butoxyhydride |
| LiHMDS | lithium bis(trimethylsilyl)amide |
| LiOH | lithium hydroxide |
| Me | methyl |
| MeCN | acetonitrile |
| MEK | methyl ethyl ketone (or butanone) |
| MIBK | methyl iso-butyl ketone (or 4-Methylpentan-2-one) |
| 2-MeTHF | 2-methyl tetrahydrofuran |
| MIBK | methyl iso-butyl ketone (or 4-Methylpentan-2-one) |
| MSA | methanesulfonic acid |
| MTBE, TBME | Methyl tert-butyl ether |
| MeOH | methanol |
| MgSO₄ | magnesium sulfate |
| MsOH or MSA | methylsulfonic acid |
| NaBH₃CN | Sodium cyanoborohydride |
| NaCl | sodium chloride |
| NaH | sodium hydride |
| NaHCO₃ | sodium bicarbonate |
| NaHMDS | sodium bis(trimethylsilyl)amide |
| Na₂CO₃ | sodium carbonate |
| NaOH | sodium hydroxide |
| Na₂SO₃ | sodium sulfite |
| Na₂SO₄ | sodium sulfate |
| NBS | N-bromosuccinimide |
| NCS | N-chlorosuccinimide |
| NH₃ | ammonia |
| NH₄Cl | ammonium chloride |
| NH₄OH | ammonium hydroxide |
| NMP | 1-Methylpyrrolidin-2-one |
| Pd | palladium |
| [Pd(allyl)Cl]₂ | allylpalladium chloride dimer |
| PdCl2(MeCN)₂ | dichlorobis(acetonitrile)palladium(II) |
| Pd₂(dba)₃ | tris(dibenzylideneacetone)dipalladium(0) |
| Pd₂(dba)₂ | bis(dibenzylideneacetone)palladium(0) |
| Pd(OAc)₂ | palladium(II) acetate |
| Pd/C | palladium on carbon |
| Pd(dppf)Cl₂ | [1,1'-bis(diphenylphosphino)-ferrocene]dichloropalladium(II) |
| Pd tetrakis | tetrakis(triphenylphosphine)palladium |
| Ph₃PCl₂ | dichlorotriphenylphosporane |
| PG | protecting group |
| PLP | (4-formyl-5-hydroxy-6-methylpyridin-3-yl)methyl phosphate |
| POCl₃ | phosphorus(V) oxychloride |
| Pt | Platinum |
| Pt/V/C | Platinum vanadium on carbon |
| PyBOP | (benzotriazol-1-yloxy)tripyrrolidinophosphonium hexafluorophosphate |
| PPTS | pyridinium para-toluenesulfonate |
| PTFE | polytetrafluoroethylene |
| i-PrOH or IPA | isopropanol |
| n-PrOAc | n-propyl acetate |
| PTSA | para-toluenesulfonic acid |
| [RuCl(p-cymene)((R)-H8-binap)]Cl | Chloro[(R)-(+)-2,2'-bis(diphenylphosphino)-5,5',6,6',7,7',8,8'-octahydro-1,1'-binaphthyl](p-cymene)ruthenium(II) chloride |
| SiO₂ | silica oxide |
| SnCl₂ | tin(II) chloride |
| SPhos | 2-dicyclohexylphosphino-2',6'-dimethoxybiphenyl |
| TCFH | chloro-N,N,N',N'-tetramethylformamidinium hexafluorophosphate |
| TEA | triethylamine |
| TFA | trifluoroacetic acid |
| TMSCl | Trimethylsilyl chloride |
| THF | tetrahydrofuran |
| TEOF | Triethyl orthoformate |
| TMOF | Trimethyl orthoformate |
| TMSCHN₂ | trimethylsilyldiazomethane |
| TRIS | tris(hydroxymethyl)aminomethane |
| Xantphos | 4,5-Bis(diphenylphosphino)-9,9-dimethylxanthene |
| XPhos | 2-Dicyclohexylphosphino-2',4',6'-triisopropylbiphenyl |

The preparation of intermediates Compounds 3a-Cl, 4a, 5a, 6a, 7a, 35, and 36 are described in Scheme 10 (an embodiment of the general Scheme 1 described above) and Examples 1-4. Embodiments of the general Scheme 2 to form Compound (I) are described in Examples 5-12 below.

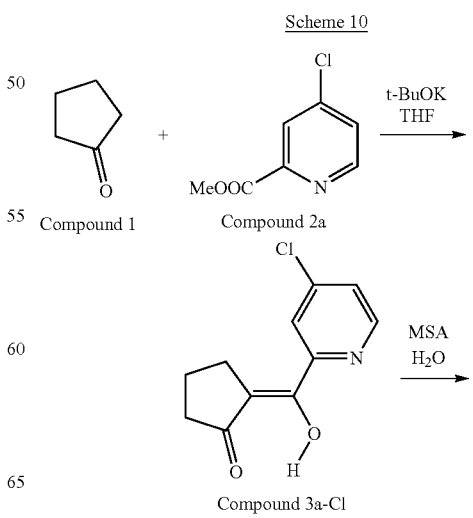

Scheme 10

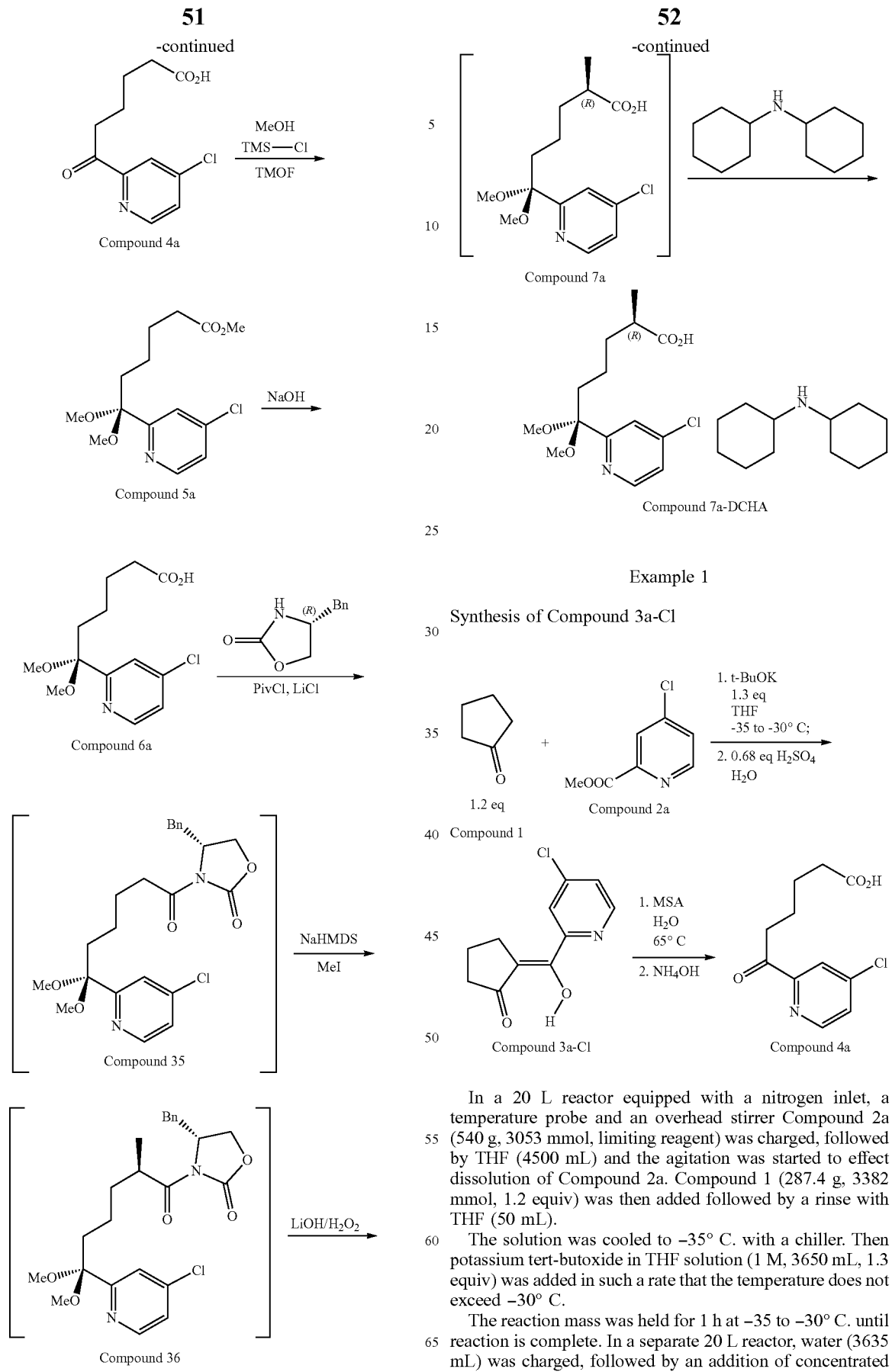

Example 1

Synthesis of Compound 3a-Cl

In a 20 L reactor equipped with a nitrogen inlet, a temperature probe and an overhead stirrer Compound 2a (540 g, 3053 mmol, limiting reagent) was charged, followed by THF (4500 mL) and the agitation was started to effect dissolution of Compound 2a. Compound 1 (287.4 g, 3382 mmol, 1.2 equiv) was then added followed by a rinse with THF (50 mL).

The solution was cooled to −35° C. with a chiller. Then potassium tert-butoxide in THF solution (1 M, 3650 mL, 1.3 equiv) was added in such a rate that the temperature does not exceed −30° C.

The reaction mass was held for 1 h at −35 to −30° C. until reaction is complete. In a separate 20 L reactor, water (3635 mL) was charged, followed by an addition of concentrated sulfuric acid (193.3 g, 0.69 equiv). The reactor was set to jacket temperature of 10° C. and the batch was cooled to 12° C. The cold solution from the cryo-reactor (−35 to −30° C.) was charged into the 20 L reactor containing cooled aq. H$_2$SO$_4$ via a transfer tube, maintaining the temperature <10° C. After the transfer was completed, the THF was then distilled off at 20 to 25° C. under vacuum to ~7.5 L volume. At this point a solid formed. The slurry was filtered and washed with water (2000 mL, 3.7 V). 1,061 g of Compound 3a-Cl was obtained as a tan solid.

$^1$H NMR (500 MHz, DMSO-d$_6$) δ 14.97 (br s, 0.5H), 8.73 (t, J=5.1 Hz, 1H), 8.02-7.98 (d, J=24.1 Hz, 1H), 7.85-7.75 (dd, J=32, 5.1 Hz, 1H), 4.70 (t, J=9.5 Hz, 0.5H), 2.93 (t, J=7.2 Hz, 1H), 2.61-2.53 (m, 1H), 2.44-2.21 (m, 2H), 2.08 (ddd, J=12.3, 8.2, 4.0 Hz, 1H), 2.01-1.81 (m, 1H).

LRMS calculated for C$_{11}$H$_{11}$ClNO$_2$$^+$ [M+H]$^+$ 224.05, observed 224.28.

Example 2

Synthesis of Compound 4a

In a 20 L cryo-reactor, 70 wt % MSA solution (1074 g, 7823 mmol, 2.83 equiv) was charged, followed by water (4900 mL). The reaction mixture was heated to 65° C. The wet cake of Compound 3a-Cl was then charged into the reactor, and the reaction mass was heated at 65° C. for 3 h until completion. The reaction mass was then cooled to 20-25° C. and aqueous NH$_4$OH (28 wt %) solution (489 g, 3907 mmol, 1.41 equiv) was added. A pH probe was used to adjust the pH to 5.06. The resulting slurry was heated to 44° C. and held at 44 C overnight. The reaction mass was cooled to 20-25° C. and the slurry was filtered and the resulting cake was washed with water (3000 mL, 6 V). The wet cake was dried using vacuum oven (50° C., 100 mmHg) for 2 days to yield 590 g of Compound 4a as a white solid.

$^1$H NMR (500 MHz, DMSO-d$_6$): δ 12.01 (br s, 1H), 8.75-8.67 (m, 1H), 7.94 (br s, 1H), 7.86-7.78 (m, 1H), 3.16 (br t, J=6.8 Hz, 2H), 2.25 (br t, J=6.6 Hz, 2H), 1.70-1.60 (m, 2H), 1.60-1.50 (m, 2H).

LRMS calculated for C$_{11}$H$_{13}$ClNO$_3$$^+$ [M+H]$^+$ 242.06, observed 242.24.

Example 3

Synthesis of Compounds 5a and 6-Cl

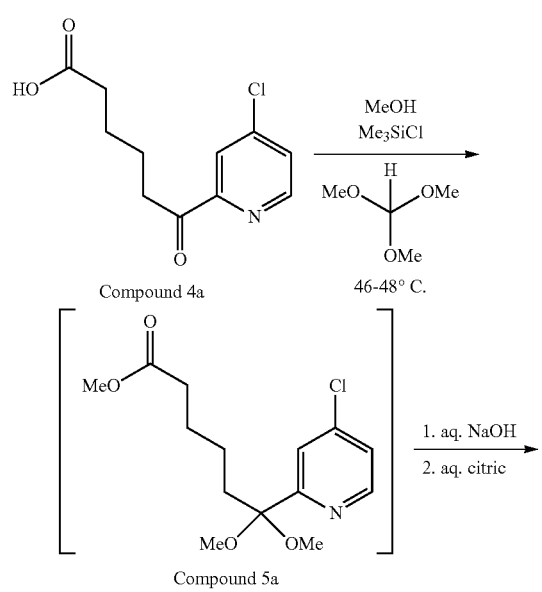

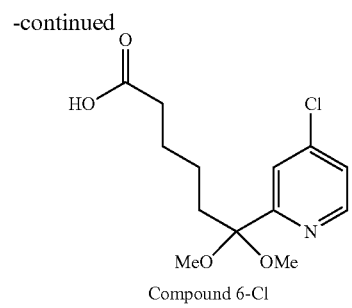

Compound 6-Cl

In a 20 L reactor, MeOH (4 L) and Compound 4a (367.3 g, 1500 mmol, 98.9 mass) were charged. This was followed by addition of 3 L MeOH. Then, trimethyl orthoformate (734 mL, 6700 mmol, 100 mass %, 4.5 eq.) was added, followed by a MeOH (400 mL) rinse. chlorotrimethylsilane (367 mL, 2880 mmol, 100 mass %, 1.92 eq.) is charged, followed by addition of MeOH (200 mL). The reaction was heated to 49° C. internal temperature, for 12 h.

In a separate 20 L reactor, NaOH (10 N) 1220 mL was added, followed by addition of 1620 mL of H$_2$O, and the reaction mass was cooled to 0° C. The content of the reaction, which contains Compound 5a, was transferred to the reaction containing aqueous NaOH. Internal temperature increased from 5° C. to 22° C. A 700 mL of MeOH was used to rinse the main reactor and transferred the content to the quench reactor. The reaction was stirred for 4 h. The reactor was warmed to jacket temperature of 20° C., stirred. MTBE (2570 mL) was then charged. The agitation was stopped and the aqueous product-rich layer was collected and taken forward. 2985 mL of 20 wt % citric acid was then added to the stirred aqueous phase. A slurry formed when a pH of 5.3 is reached, and then was filtered. Compound 6-Cl was obtained as a solid 387.1 g (89.6% yield).

$^1$H NMR (400 MHz, DMSO-d$_6$) δ 11.98 (br s, 1H), (8.61 (d, J=4.8 Hz, 1H), 7.60 (d, J=1.8 Hz, 1H), 7.51 (dd, J=5.2, 2.1 Hz, 1H), 3.03 (s, 6H), 2.08 (t, J=7.5 Hz, 2H), 2.02 (br d, J=16.9 Hz, 2H), 1.42-1.30 (m, 2H), 0.90-0.78 (m, 2H)

LRMS calculated for C$_{12}$H$_{15}$ClNO$_3$$^+$ [M-CH$_3$O]$^+$ 256.07, observed 256.24.

Example 4

Synthesis of Compound 7a-DCHA

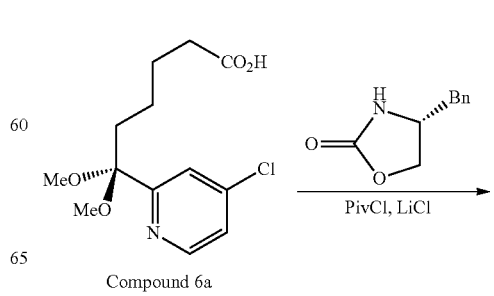

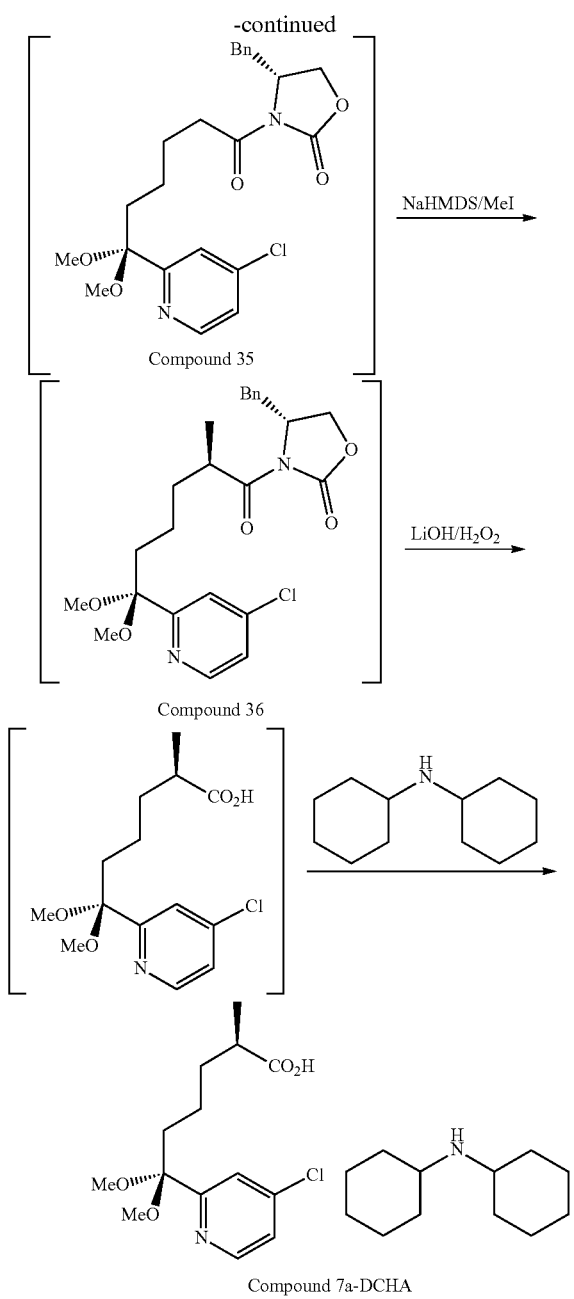

(270 mL). After 15 min of mixing, the 2 phases were separated, and the lower aqueous phase was discarded. The organic phase was washed with 7 wt % NaHCO$_3$ (270 mL) and water (270 mL). After phase separation, the lower aqueous phase was discarded. The organic layer was distilled down to 220 mL. And then anhydrous THF (1860 mL) was added. The solution was passed through a 0.45 micron polish filtered.

The solution containing Compound 35 was then cooled to −45° C. and methyl iodide, (95.4 g, 2.2 equiv) was added followed by 1N NaHMDS in THF (458 mL, 1.5 equiv) in such a rate that the temperature not exceed −39° C. The reaction mass was held for 6 h. The reaction mixture was then neutralized with a solution of acetic acid (29.30 g, 1.6 equiv) in anhydrous THF (88 mL) in one portion. The organic reaction mass was washed with 14 wt % NaCl solution (530 mL) and then 7.0 wt % NaHCO$_3$ solution (530 mL). After the washes, the organic solution containing Compound 36 was concentrated to 220 mL.

THF (880 mL) was added and the solution was cooled to 0° C. A 30 wt % H$_2$O$_2$ solution, (64.18 g, 1.82 equiv) was then added, followed by an addition of a solution of lithium hydroxide, (12.42 g in 110 mL water) over 10 min. After a 6 h hold, a solution of a 10 wt % solution of sodium bisulfite (63.48 g, 2.0 equiv, in 580 mL water). The mixture was aged for 1 h. THF was then removed by distillation until ~ 700 mL was collected.

The pH was then adjusted to around 9.5 using 10 N NaOH. Toluene (540 mL) was added. The biphasic mixture was mixed for 15 min and then settled. The separated organic layer was further extracted with 360 mL of sat. NaHCO$_3$. The combined aqueous layers were charged back to the reactor and extracted with MTBE (720 mL). The organic layer was discarded.

The product rich aqueous layer containing Compound 7a was charged back to the reactor and MTBE (900 mL) was added. The pH was adjusted to 4.4 using citric acid.

MTBE was removed by distillation and replaced with a MeCN/MTBE 4:1 (6 volume) based on input of Compound 7a (potency corrected). The resulting stream was polish filtered and the Polish filter the solution. Dicyclohexylamine was then added in portion (up to 1.5 eq, wrt Compound 7a). The slurry was heated to 55° C. and held for 30 min. The reaction mass was then cooled to 0° C. The slurry was filtered over a Buchner funnel under N$_2$ protection, washed with 2.0 volume of cold MeCN (0° C.), dried under vacuum, then in vacuum oven at 50° C. for 24 h. Compound 7a-DCHA was obtained as a white solid. 61 g (88.2% over the salt formation step, overall yield over four-steps from Compound 6a is 61.6%. Compound 7 is a 1:1.5 complex of compound 7: dicyclohexylamine.

Compound 6a (87.88 g, 305 mmol, the limiting agent) was charged into a 2 L chem-glass reactor, followed by anhydrous THF (1760 mL). The THF was distilled off, down to 10 Vol. The KF of the solution is <200 ppm. An additional THF (880 mL) was added along with triethylamine, CAS 121-44-8 (106.4 mL, 2.5 equiv). The solution was cooled to 0° C. and pivaloyl chloride, CAS 3282-30-2 (44.13 g, 1.2 equiv) was added through an addition funnel in such a rate that the temperature not exceed 5° C. After a 30 min hold, lithium chloride, (16.16 g, 1.2 equiv) was added. After 15 min aging, the chiral auxiliary, CAS 102049-44-7 (64.86 g, 1.2 equiv) was charged in one shot, as a solid. The slurry was allowed to warm up to 20° C. over 3 h and age overnight. The THF was then distill off to a final volume of 800 mL under vacuum. Toluene was charged (530 mL), followed by a saturated aqueous solution of NH$_4$Cl (270 mL) and water $^1$H NMR (400 MHz, MeOH-d$_4$): 8.52 (d, J=5.3 Hz, 1H), 7.72 (d, J=2.0 Hz, 1H), 7.44 (dd, J=5.3, 2.0 Hz, 1H), 3.16 (d, J=3.0 Hz, 6H), 3.07-2.97 (m, 3H), 2.20-2.06 (m, 3H), 2.05-1.99 (m, 6H), 1.90-1.80 (m, 6H), 1.76-1.67 (m, 3H), 1.60-1.47 (m, 1H), 1.33-1.10 (m, 16H), 1.00 (d, J=6.8 Hz, 3H), 0.97-0.87 (m, 2H).

LRMS calculated for C$_{13}$H$_{17}$ClNO$_3^+$ [M-CH$_3$O]$^+$ 270.09, observed 270.24.

Example 5

Synthesis of Compound 9a

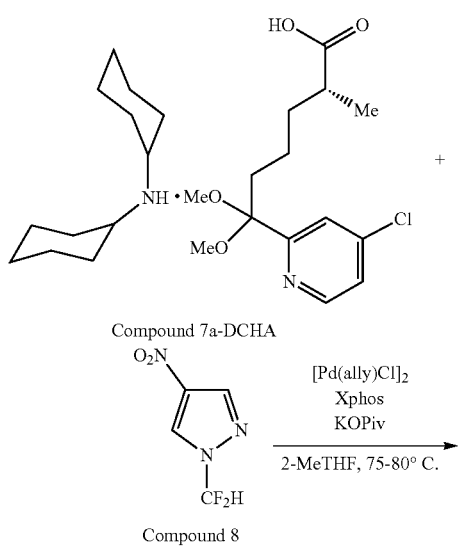

Compound 7a-DCHA

Compound 8

Compound 9a

To a 2 L clean reactor equipped with an overhead stirrer, a thermocouple, and a nitrogen inlet was charged with 2MeTHF (500 mL), catalyst [Pd(allyl)Cl]$_2$ (1.57 g, 0.05 equiv.) and Xphos (4.48 g, 0.055 equiv.) in sequence to give a mostly homogenous pale yellow solution at 20° C. Salt Compound 7a-DCHA (98.2 g, 1.0 equiv.) and pyrrole Compound 8 (32.3 g, 1.15 equiv.) was added portion wise into the reactor to give a white suspension. After 30 min, in one portion, KOPiv (32.3 g, 1.3 equiv.) was added into the solution and the reactor was raised with 2-MeTHF (500 mL) which was bubbled with N$_2$ for 30 min. Under N$_2$, the solution was refluxed for 10 hours to give a black suspension. The crude was cooled to 20° C. and quenched with K$_3$PO$_4$ (550 mL, 20% aq.) to pH between 10.0 and 10.5, the aqueous layer was separated and the organic layer was washed with K$_3$PO$_4$—K$_2$HPO$_4$ buffer solution (800 mL, pH 10.2, aq.). The aqueous layer was combined and filtered to give dark solution. The aqueous solution was added 2-MeTHF (1300 mL) and activated charcoal (13.9 g, Darco G-60) and the solution was acidified with citric acid (254 g, 3.4 equiv.) portion wise in 30 min to pH 5-6. The suspension and stirred for 30 min at 20° C. The suspension was filtered and the organic layer was kept and concentrated in vacuo to 300 mL and exchanged solvent with nBuOH (1000 mL) under 150 mbar vacuum at 80° C. The resulting solution's concentration was adjusted to 170-180 mg/mL (500 mL, no more than 5% wt 2-MeTHF in the solution). This solution was cooled to 0° C. gradually in 10 h and kept at 0° C. for another 10 h to give a white slurry. The slurry was filtered through Nutsche filter and the reactor was raised with nBuOH (100 mL) and the resulting suspension was used to raise the cake. The cake was raised with heptane (100 mL) and dried under oven (house vacuum 50° C. 24 h). The isolated Compound 9a (73.2 g, 95 wt %) was obtained in 83% yield.

$^1$H NMR (400 MHz, DMSO-d$_6$): δ 8.89-8.80 (m, 1H), 8.72-8.65 (m, 1H), 7.88-7.52 (m, 3H), 3.10-3.00 (m, 6H), 2.50 (dt, J=3.5, 1.8 Hz, 1H), 2.52-2.44 (m, 1H), 2.22-2.13 (m, 1H), 2.11-1.99 (m, 2H), 1.51-1.35 (m, 1H), 1.27-1.14 (m, 1H), 1.00-0.84 (m, 5H). $^{13}$C NMR (101 MHz, DMSO-d$_6$) δ 177.3, 158.9, 149.5, 139.3, 138.3, 135.0, 132.8, 123.5, 123.0, 110.5 (t, J=253.9 Hz, 1C), 103.0, 48.2, 48.2, 38.4, 34.0, 32.9, 20.4, 16.6.

LRMS, [M-OMe]$^+$ C$_{17}$H$_{19}$F$_2$N$_4$O$_5^+$: 397.36, 397.13.

Example 6

Synthesis of Compound 10a

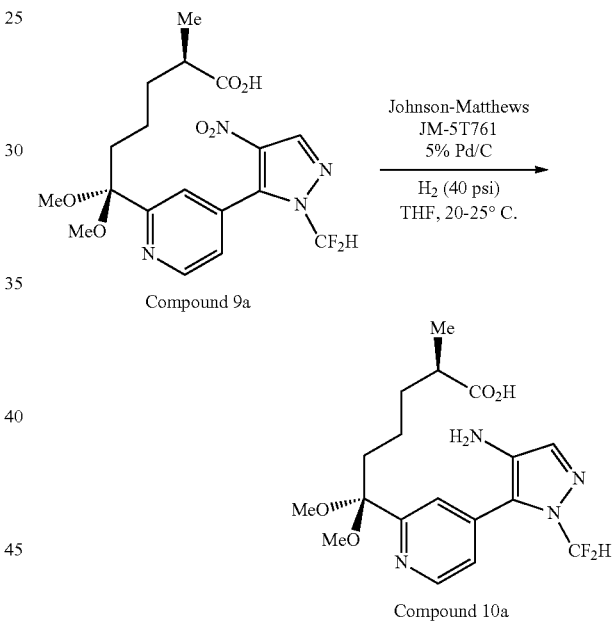

Compound 9a

Compound 10a

To a pressure reactor equipped with an overhead stirrer, a thermocouple, and a nitrogen inlet was charged with THF (900 mL), Pd/C (4.6 g, 10% wt, 0.1 equiv.) and Compound 9a (46.0 g, 1.0 equiv.) in sequence to give a suspension at 20° C. The reactor was flashed with N$_2$ and H$_2$ three time each. Under H$_2$ (40 psi), the solution was vigorously stirred for 18 h. The crude was discharged from the reactor and filtered through a Nutsche filter. The THF solution was concentrated down to clear oil Compound 10a (101 g, 40% wt) in 95% yield. Small sample was taken and thoroughly concentrated for spectrum analysis.

$^1$H NMR (500 MHz, CDCl$_3$): δ 8.77 (1H, s, br), 7.75 (1H, s. br), 7.39 (1H, s. br), 7.33 (1H, s. br), 7.11 (1H, t, J=59.1 Hz), 5.75 (3H, s, br), 3.17 (6H, s), 2.35-2.25 (1H, m), 2.20-1.98 (2H, m), 1.55-1.43 (1H, m), 1.30-1.13 (1H, m), 0.80-1.09 (5H, m).

LRMS, [M+H]$^+$ C$_{18}$H$_{25}$F$_2$N$_4$O$_4^+$: 399.18.

Example 7

Synthesis of Compound 11a-FUM

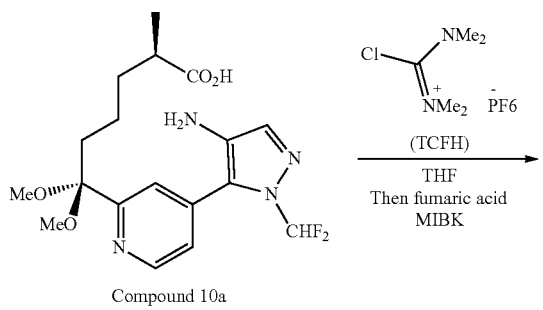

Compound 10a

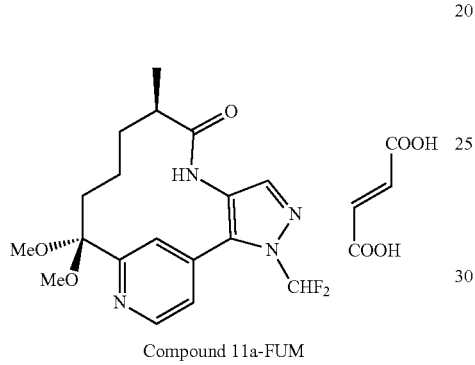

Compound 11a-FUM

In a 1 L reactor, 600 mL of THF was added followed by charge of chloro-N,N,N',N'-tetramethylformamidinium hexafluorophosphate (TCFH, 17.1 g, 59.7 mmol, 98.0 mass %, 1.52 equiv). Additional 200 mL of THF was used to rinse in all the TCFH into the reactor. To the suspension, N,N-diisopropylethylamine (14.6 mL, 83.7 mmol, 100 mass %, 2.13 equiv) was added and stirred at room temperature. In a 50 mL syringe, solution of Compound 10a in THF (44.9 g, 39.2 mmol, 34.8 mass %, 1.00 equiv), and added the solution to the reactor using syringe-pump over 10 h (ca. 5 mL/h rate).

The reaction stream (~50 mL, corresponding to 1 g of Compound 11a input) was solvent-swapped from THF to MIBK (~20 mL). The organic layer was washed with aq. $K_2HPO_4$ (15%, 15 mL), followed by addition of 1.2 equiv (mol/mol to input Compound 11a) of solid fumaric acid. Subsequent the mixture was concentrated in vacuo to ~ 8 mL. Tan slurry of product formed which was filtered, the cake was washed with MIBK (2 mL) and then heptane (2 mL), dried under vacuum. Yield=1.01 g (75.3% potency corrected from Compound 11a input). Potency=74.2 wt %, ee=97.3%.

1H NMR (400 MHz, DMSO-d6) δ 13.31-13.02 (m, 1H), 9.30 (s, 1H), 8.76 (d, J=5.1 Hz, 1H), 7.94 (s, 1H), 7.87-7.79 (m, 1H), 7.66-7.60 (m, 1H), 7.41-7.35 (m, 2H), 6.64 (s, 2H), 3.22 (s, 3H), 3.15 (s, 3H), 2.41-2.28 (m, 1H), 1.85-1.60 (m, 3H), 1.55-1.41 (m, 1H), 0.88 (br d, J=7.1 Hz, 4H), 0.46 (br s, 1H)

LRMS calculated for $C_{17}H_{19}F_2N_4O_2^+$ 349.15 $[M-CH_3O]^+$, observed 349.08.

Example 8

Synthesis of Compound 12

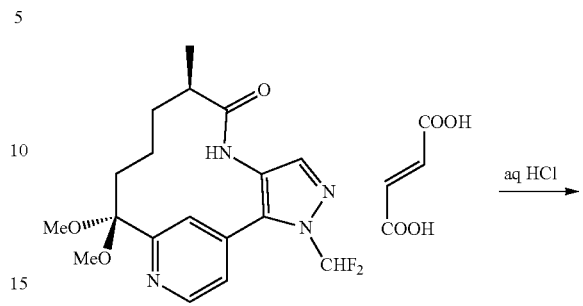

Compound 11a-FUM

Compound 12

To a slurry of Compound 11a-FUM (0.50 g, 67 wt %, 96 ee %) in water (5 mL) was added cyclopentyl methyl ether (2.5 mL), followed by trifluoroacetic acid (0.23 mL, 3.5 equiv). The resulting mixture was heated to 45° C. for 5 h. The mixture was then cooled to ambient temperature, and filtered. The reactor was rinsed with water (2.5 mL), the rinse was applied for the cake washed. The filtrates were combined and the phase was separated. The resulting organic phase was extracted with aq. HCl solution (0.5N, 2.0 mL). The acidic aqueous extraction was combined with the early acidic aqueous phase from the reaction. The pH of the combined aqueous solution was adjusted to 9-10 by addition of solid $K_3PO_4$ (~2 g). The resulting mixture was stirred for 2 h, and filtered. The filtered cake was washed with water (5 mL×2) and MTBE (5 mL×2), and dried in vacuo, affording Compound 12 (0.25 g, 78%, 97.2 ee %).

$^1$H NMR (500 MHz, $CDCl_3$): δ 8.89 (s, 1H), 7.97 (s, 1H), 7.68 (s, 2H), 7.46 (s, 1H), 7.34 (t, J=59.7 Hz, 1H), 6.85 (br s, 1H), 3.14 (br s, 1H), 2.82 (br d, J=8.9 Hz, 1H), 2.46-2.37 (m, 1H), 2.05 (br s, 1H), 1.68 (br d, J=7.0 Hz, 1H), 1.41 (br s, 1H), 1.21 (br s, 3H).

LRMS, $[M+H]^+$ $C_{16}H_{17}F_2N_4O_2^+$: 335.18.

Example 9

Alternative Synthesis of Compound 12

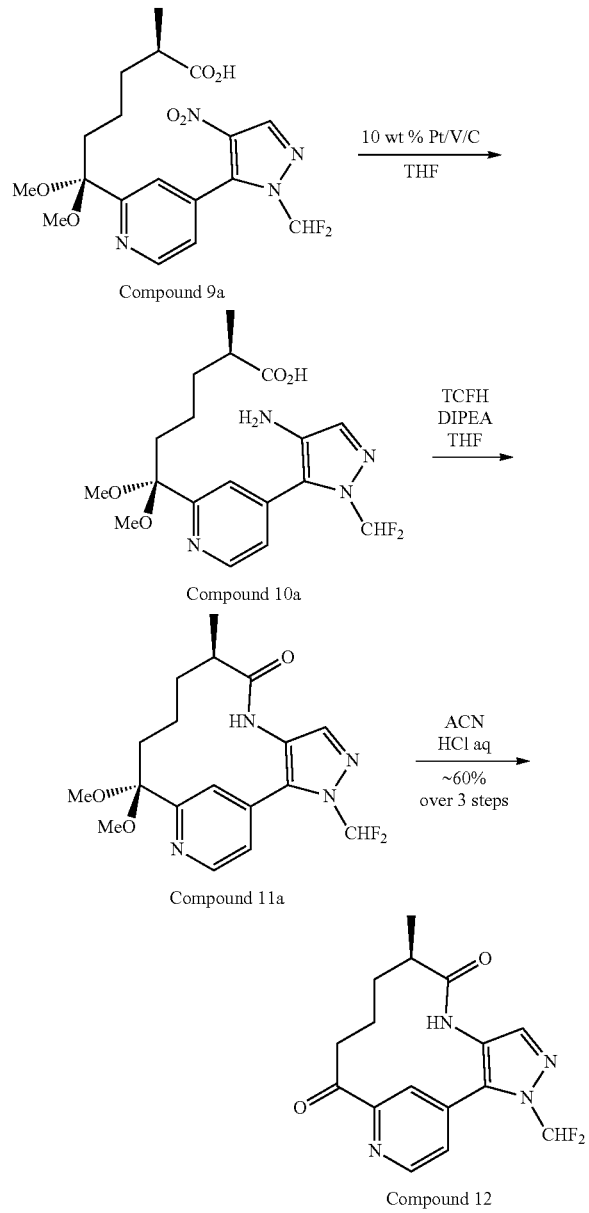

To pressurized 1 L vessel was added Compound 9a (75.0 g 169 mmol), THF (525 mL) and Pt/V/C (~50% wet, 10 wt %, 7.5 g). The reactor was flushed with $N_2$ and $H_2$ three times each. Under $H_2$ (1.5 bar), the solution was vigorously stirred for 1 h at 20° C. then warmed up to 40° C. for 16 h. The mixture was discharged from the reactor and filtered, the resulting solution was concentrated and water was azeotropically distilled by continues distillation with THF. In a separate reactor was added successively THF (1.2 L), followed by chloro-N,N,N',N'-tetramethylformamidinium hexafluorophosphate (TCFH, 70 g, 1.52 eq.) and N,N Diisopropylamine (103 mL, 3.5 eq.). The mixture was stirred vigorously and heated to 55° C. To this mixture was dosed the solution of Compound 10 in THF over 20 h (~50 mL/h).

The mixture was then concentrated and solvent switch to Acetonitrile was performed to end up with about 4 L/kg of Compound 11 in acetonitrile. Then, aqueous solution of hydrochloric acid (3N, 23 mL) were charged and the reaction mixture was heated at 55° C. for 15 h to form the crude Compound 22. The reaction was cooled to 10° C. prior to charge 270 mL of dichloromethane, 540 mL of water and hydrochloric acid (10.8N, 71 mL). after stirring for 1 h, the phase was separated and the bottom organic layer was discarded. To the aqueous layer at 10° C. was added potassium hydroxide (22.5 wt %, ~169 mL) until pH increase to 3.0. After 1 h of stirring at pH 3, further addition of potassium hydroxide (22.5 wt %, ~17 mL) to the reaction was carried until pH reached 9.5. Compound 12 was isolated by filtration, rinse with 169 mL of water and 114 mL of EtOH and then dried.

Example 10

Synthesis of Compound 13

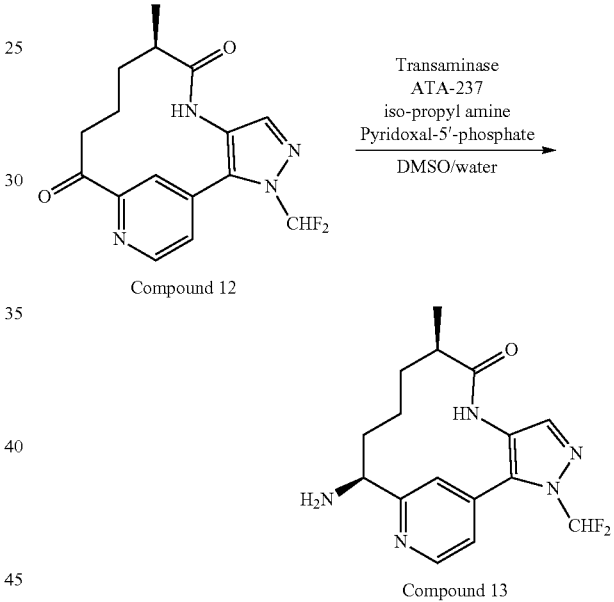

A jacketed 125 mL reactor with a water circulator to maintain the reaction temperature at 35° C. was used during the course of the reaction. A calibrated pH stat was used to control the pH at 7.5 and dispense 4M aqueous isopropyl amine into the reactor. Charge ketone Compound 12 (5.0 g, 50 g/L), DMSO (30 mL, 30%) and pyridoxal-5-phosphate monohydrate (53 mg, final concentration 2.0 mM) into the reactor. 1M Solution of isopropyl amine hydrochloride was prepared in water and 63 mL (final concentration 0.7 M) was charged into the reactor. The reaction mixture was stir for 2.0 min. The reaction was heterogeneous. Amine transaminase ATA-237 (0.5 g) was dissolved in 4.0 mL of 1M isopropyl amine hydrochloride solution and added into the reactor. The enzyme container was rinsed with another 3.0 ml of 1M isopropyl amine hydrochloride solution and that was charged into the same reactor. Samples 20 μL were pipette out, diluted with 980 μL of methanol, vortexed, centrifuged at 14000×g for 2.0 min, filtered through 0.2 μM PTFE filter and analyzed by HPLC for conversion and de. The reaction was stopped after 8 h (conversion 99.7%).

The reaction mixture was acidified to pH 1.3 (6N HCl, 3.6 mL). A celite pad was prepared and the reaction mixture was filtered through the celite. After filtration the reactor and the celite pad were rinsed with 30 mL water and solution was pooled with the filtrate. The reaction mixture was extracted with 130 mL of 2-methyltetrahydrofuran and 2-methyl tetrahydrofuran solution was discarded. The pH of the aqueous layer was increased to 10.5 with 10N sodium hydroxide (4.4 mL). Aqueous layer (152 mL) was extracted with 150 mL of n-butanol (volume of organic layer 190 mL, volume of aqueous layer 105 mL) and layers were separated. Aqueous layer (105 mL) was again extracted with 100 mL of n-butanol and aqueous and organic layer were separated (volume of aqueous layer 75 mL, volume of organic layer 125 mL).

Organic layers were pooled and the solvent was concentrated to 40 g viscous liquid. The residue was solidified at 4° C. in 1 h. The residue was suspended in 240 mL of MTBE and stir vigorously. The precipitates were filtered and filtrate was discarded. The precipitates (6.6 g) were stir with 50 mL water and pH was increased to 8.5. The desired compound was precipitated, filtered and washed with MTBE. The volume of the filtrate was reduced (15 mL), pH was increased to 9.0, and precipitated compound was filtered and washed with MTBE. Two crops were mixed and dried overnight in the vacuum oven at 35° C. Desired Compound 13 was isolated as off-white solid, 3.94 g, yield 78.8%, AP 99.3, de>99.9%, potency 97%.

$^1$H NMR (400 MHz, DMSO-d$_6$) δ 9.33 (s, 1H), 8.76-8.62 (m, 1H), 7.94 (t, J$_{H-F}$=57.8 Hz, 1H), 7.84 (s, 1H), 7.42-7.33 (m, 1H), 7.33-7.24 (m, 1H), 4.02-3.86 (m, 1H), 2.61-2.52 (m, 1H), 2.15 (br s, 2H), 1.86-1.66 (m, 2H), 1.52-1.33 (m, 2H), 1.15-0.95 (m, 1H), 0.89-0.73 (m, 3H), 0.27-0.06 (m, 1H)

LRMS, [M+H]$^+$ C$_{16}$H$_{20}$F$_2$N$_5$O$^+$ 336.24.

Example 11

Alternate Synthesis of Compound 13

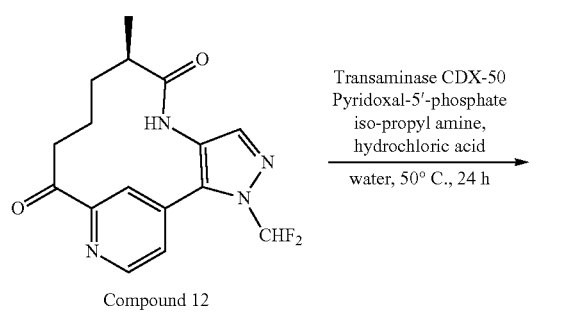

Compound 12

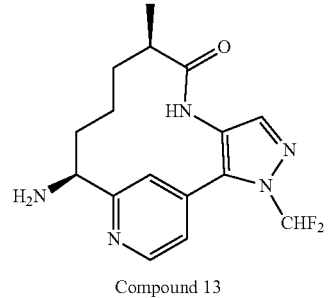

Compound 13

In a 500 mL reactor filled with 139 mL of water was dosed hydrochloric acid (12N, 22.6 m, 3.35 eq.) over 90 minutes at 25° C. Isopropylamine (4.05 eq, 25.88 mL) was then added until pH reaches 10.5. Compound 12 (25 g) and pyridoxal-5'-phosphate (0.01 g/g, 0.25 g) were then charged followed by the transaminase CDX-50 (0.02 g/g, 0.50 g). the reaction mixture was heated to 50° C. and stirred for 24 h. hydrochloric acid (12N, 0.6 eq, 4 ml) was charged as well as 1 g of celite (4 wt %). The reaction mixture was heated to 80° C. for 2 h then cooled to 20° C. prior to filtration and rinse. The solid residue was discarded, and the mixture was heated to 50° C. A solution of potassium hydroxide (10 wt %, 65 mL, 1.55 eq) was then dosed until pH reached 9.5. the mixture was then cooled to 20° C. over 3 h. Compound 13 was isolated by filtration, rinse with water and dried.

Example 12

Synthesis of Compound (I)

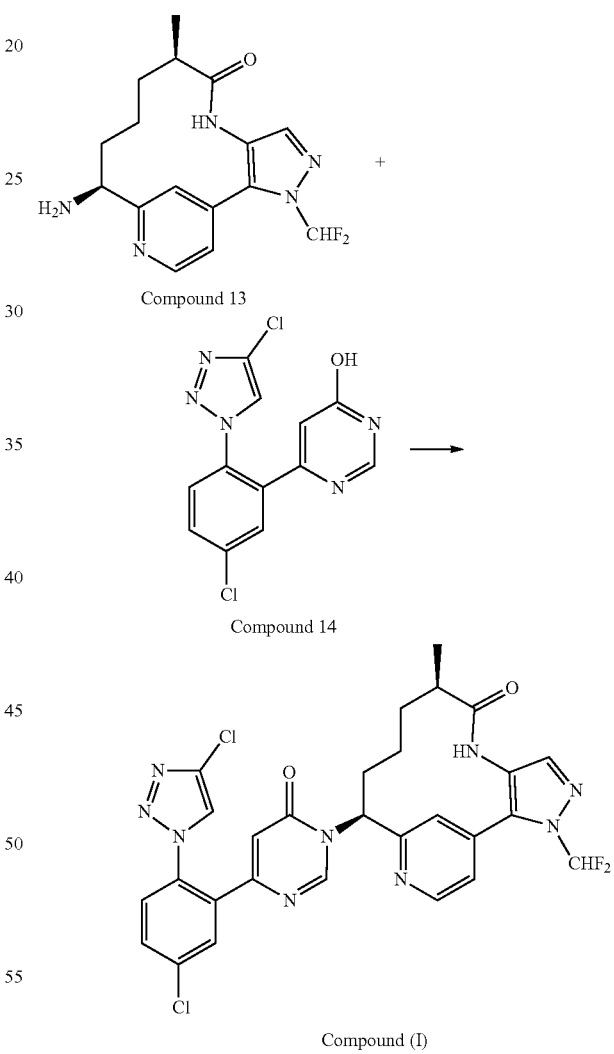

To a scintillation vial containing Compound 14 (0.019 g, 0.062 mmol), HATU (33.0 mg, 0.087 mmol) in anhydrous ACN (0.5 mL) was added DBU (15 μL, 0.100 mmol). After 30 min, a solution of Compound 13 (0.021 g, 0.062 mmol), in 0.5 ml CH$_3$CN and DMF (0.1 ml) was added. The resulting solution was stirred at rt for 2 h then purified by reverse phase chromatography to give Compound (I) as its trifluoroacetate salt.

$^1$H NMR (500 MHz, CD$_3$OD) 8.91-8.83 (m, 1H), 8.78-8.71 (m, 1H), 8.33 (s, 1H), 7.88 (d, J=2.5 Hz, 1H), 7.74 (s, 2H), 7.69-7.67 (m, 1H), 7.65 (s, 1H), 7.63 (t, J=58 Hz, 1H), 7.52-7.50 (m, 1H), 6.36 (d, J=0.8 Hz, 1H), 6.06-5.95 (m, 1H), 2.76-2.65 (m, 1H), 2.36-2.21 (m, 1H), 2.08-1.93 (m, 2H), 1.63-1.53 (m, 1H), 1.53-1.42 (m, 1H), 0.99 (d, J=6.9 Hz, 3H).

LRMS, [M+H]$^+$ C$_{28}$H$_{23}$Cl$_2$F$_2$N$_9$O$_2$$^+$: 626.09.

Example 13

Preparation of Compound 21

As described in Scheme 3, Compound 7 can be prepared by the following reaction steps.

a). Synthesis of Compound 16

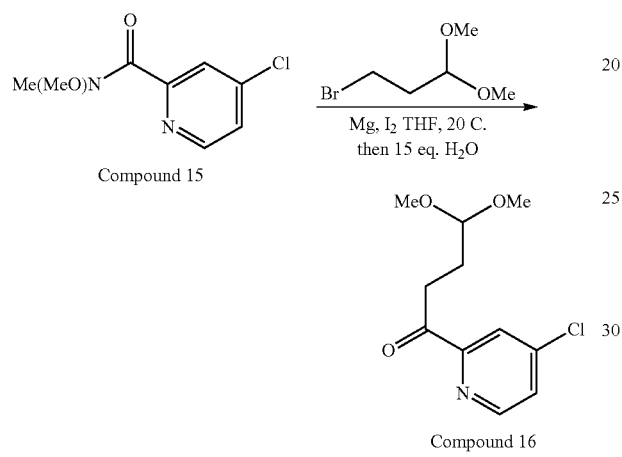

To the magnesium (8.73 g, 359 mmol, 1.35 equiv.) and a crystal of I$_2$ was added in a 1 L three-neck flask. Anhydrous THF (100 mL) was charged into the reaction flask under N$_2$. The reaction temperature was monitored by a J-chem thermometer. 3-bromo-1,1-dimethoxy-propane (65.8 g, 356 mmol, 1.35 equiv.) was diluted with THF (150 mL) and charged into the addition funnel. The 3-bromo-1,1-dimethoxy-propane solution (20 mL) was added into the flask at 20° C., the whole pale brown suspension was stirred vigorously to utilize the friction between the stir bar and the magnesium flakes to initiate the reaction. After 30 min, the pale brown color disappeared and the solution temperature raised to 45 to 50° C. The reaction was then kept the temperature between 55 to 62° C. with slow addition of 3-bromo-1,1-dimethoxy-propane solution from the addition funnel. After 1.5 hours, the addition was finished and the whole solution was kept at 60° C. for two extra hours. The solution was put into a water bath and cooled to 25° C. The 4-chloro-N-methoxy-N-methyl-pyridine-2-carboxamide, Compound 15, (53.3 g, 264 mmol, 1.0 equiv.) in THF (150 mL) was charged into the additional funnel. The solution of substrate was added into the Grignard solution within 20 min to give a reddish yellow solution, the internal temperature was kept below maximum of 35° C. After 15 min, HPLC and TLC both revealed the reaction was finished. Water (20 mL) was slowly added into the crude mixture to precipitate out all the brown gel-like solid. The whole crude was filtered through celite pad and washed with total amount of 100 mL THF twice. The crude solution was dried over Na$_2$SO$_4$. Concentration of the crude under vacuum at 30-35° C. afforded Compound 16 as a yellow oil.

Optional: The crude was good for the next reaction without purification. To obtain the spectrum: The crude was subsequently purified on ISCO purification system with hexanes/EA 1:0 to 10:1 to give desired product.

$^1$H NMR (500 MHz, CDCl$_3$) δ 8.60 (d, J=5.0 Hz, 1H), 8.04 (d, J=2.0 Hz, 1H), 7.49 (dd, J=5.2, 2.0 Hz, 1H), 4.51 (t, J=5.6 Hz, 1H), 3.35 (s, 6H), 2.10-2.05 (m, 2H), 1.66-1.60 (m, 2H).

LRMS: [C$_{10}$H$_{11}$ClNO$_2$]$^+$, 212.05, 212.10.

b). Synthesis of Compound 18-Et

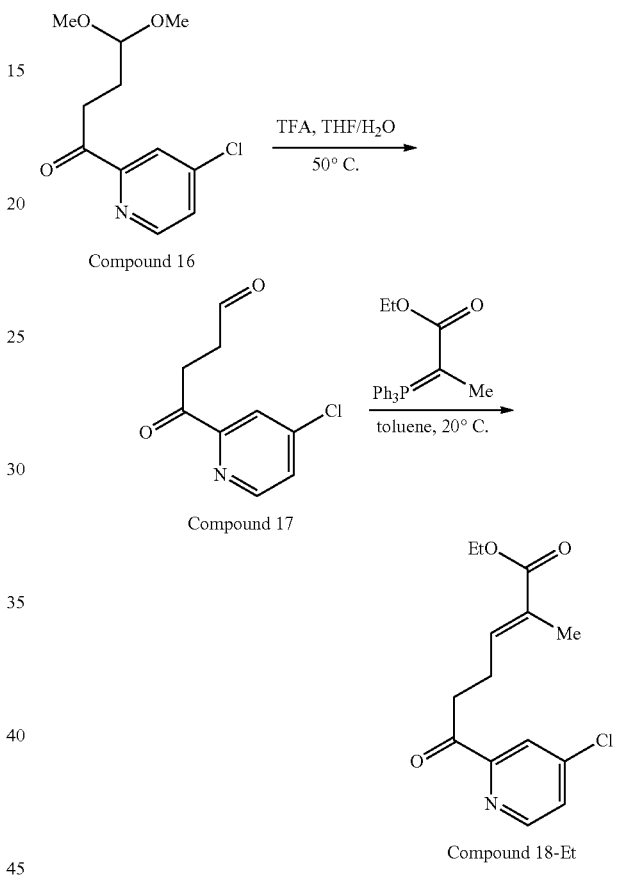

In a 250 mL round-bottom flask, Compound 16 (7.61 g, 38.5 mmol, 1 equiv.) was diluted with water (20 mL) and THF (80 mL) at 20° C. To the solution, trifluoroacetic acid (8.5 mL, 110 mmol, 2.7 equiv.) was added and the solution at room temperature. The solution was immediately warmed to 50° C. After 4 hours, the solution turned to dark brown, HPLC and TLC revealed the reaction was finished. Additional water (60 mL) was added into the flask. At 25° C., sodium bicarbonate (9.6 g, 114 mmol, 2.8 equiv.) was slowly added into the crude to neutralize the media to pH 7. The crude material was extracted with EtOAc (100 mL) three times and the combined organic crude was washed with brine (50 mL) once. The crude was dried with Na$_2$SO$_4$. The crude was filtered and concentrated to dark oil which was directly used in the next step. To the crude, CH$_2$Cl$_2$ (75 mL) was added at 20° C. To the solution containing Compound 17, ethyl-2-(triphenylphosphoranyldene)propionate (14.2 g, 38.2 mmol, 0.93 equiv.) was added in one portion. The reaction was kept at 20° C. for 8 hours. The crude was concentrated to dryness and diluted with 1:1 Hexanes:EtOAc, the solid precipitation was filtered off and washed with MTBE (20 mL) twice. The combined crude was concentrated to black oil and was purified on ISCO purification system (200 g silica gel) with hexanes/EA 1:0 to 5:1 to give desired Compound 18-Et (8.21 g, 70.3%) as yellow oil.

¹H NMR (500 MHz, CDCl3) δ 8.59 (s, 1H), 8.05 (s, 1H), 7.50 (s, 1H), 6.80 (s, 1H), 4.24-4.15 (m, 2H), 3.39-3.37 (m, 2H), 2.65-2.57 (m, 2H), 1.90 (s, 3H), 1.35-1.25 (m, 3H).

LRMS: $[C_{14}H_{17}ClNO_3]^+$, 282.09, 282.21.

c). Synthesis of Compound 19-Et

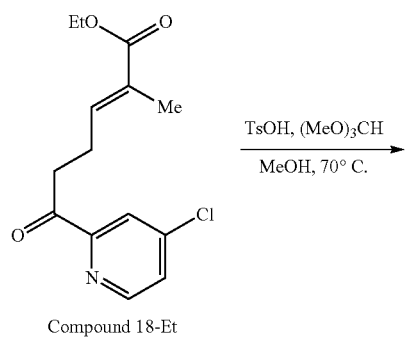

Compound 18-Et

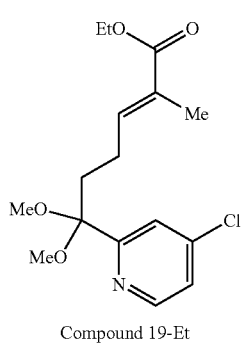

Compound 19-Et

To Compound 18-Et (9.55 g, 33.9 mmol, 1.0 equiv.) was added p-toluenesulfonic acid (2.35 g, 13.5 mmol, 0.40 equiv.), trimethyl orthoformate (24 mL, 220 mmol, 6.4 equiv.) and methanol (95 mL) at 20° C. The solution was refluxed for 60 hours. The crude was cooled to 0° C. and added sodium hydroxide (1.7 mL, 17 mmol, 0.5 equiv.) to neutralize the media to pH 7. The crude was evaporated to sticky oil and diluted with MTBE (200 mL). The crude was washed with water and brine once. The crude was dried on Na₂SO₄ and filtered. The crude was filtered and flashed on ISCO (80 g silica) with hexanes/EA 1:0 to 4:1 to give Compound 19-Et (8.1 g, 73% Yield) and ethyl (E)-6-(4-chloro-2-pyridyl)-2-methyl-6-oxo-hex-2-enoate (1.2 g, 13%).

¹H NMR (500 MHz, CDCl₃) δ 8.50 (d, J=4.0 Hz, 1H), 7.63 (d, J=0.8 Hz, 1H), 7.17 (dd, J=0.8 and 4.0 Hz 1H), 6.45 (dt, J=8.0 and 0.4 Hz, 1H), 4.06 (q, J=7.8 Hz, 2H), 3.12 (s, 6H), 2.22-2.11 (m, 2H), 1.85-1.73 (m, 2H), 1.61 (s, 3H), 1.19 (t, J=7.8 Hz, 3H).

LRMS: $[C_{16}H_{22}ClNO_4—OCH_3]^+$, 297.11, 297.10.

d). Synthesis of Compound 20

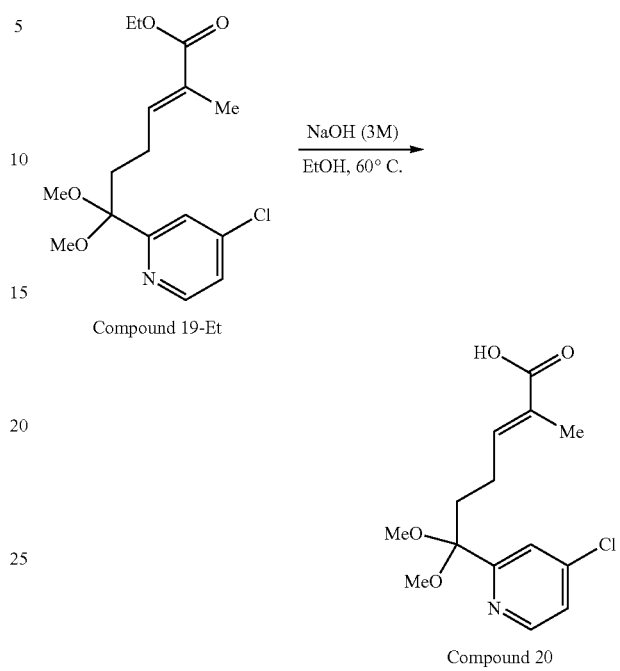

The pale yellow oil Compound 19-Et (1.14 g, 3.48 mmol, 1.0 equiv.) was diluted in ethanol (10 mL) at 20° C. To the above solution was added sodium hydroxide (2 mol/L) in water (2 mL, 4 mmol, 1.1 equiv.) at room temperature. The solution was heated to 60° C. for 12 hours. The crude was added HCl (1 mol/L) (4 mL) and evaporated the whole crude to generate white paste. Then the crude was added sat. aq. NH₄Cl (20 mL) and extracted with 2-methylTHF (10 mL) twice. The crude was dried on Na₂SO₄ and filtered, concentrated to give pink crude. The crude was filtered and flashed on ISCO (8 g silica) with hexanes/EA 1:0 to 2:1 to give Compound 20 as white crystal (1.05 g, 100%).

¹H NMR (500 MHz, CDCl₃) δ 8.61 (s, 1H), 7.73 (s, 1H), 7.28 (s, 1H), 6.80-6.65 (m, 1H), 3.21 (s, 6H), 2.29-2.20 (m, 2H), 1.95-1.85 (m, 2H), 1.70 (s, 3H).

LRMS: $[C_{14}H_{17}ClNO_4—OCH_3]^+$, 268.08, 268.18.

e). Synthesis of Compound 21

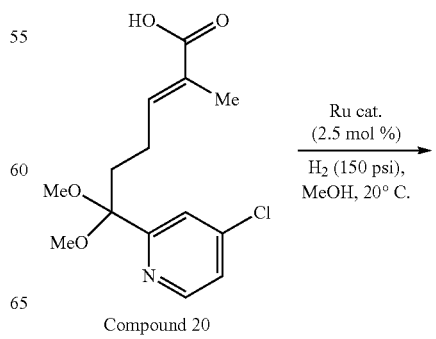

Compound 20

-continued

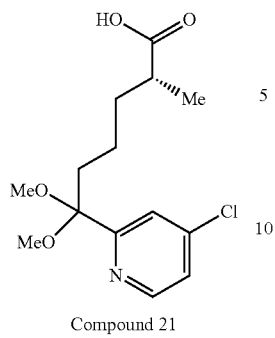

Compound 21

Compound 20 (632 mg, 2.11 mmol, 1.0 equiv.) and pressure reactor were both put into the glovebox. In the glovebox, the catalyst diacetato[(R)-(+)-2,2'-bis(diphenylphosphino)-1,1'-binaphtyl]ruthenium(II) (95 mg, 0.109 mmol, 5.2 mmol %) and methanol (5 mL) was added subsequently and the vial was put into the reactor and sealed. The reactor was put on the hydrogenation scaffold and flashed with hydrogen a couple times. The reaction was set up at 150 psi $H_2$ at room temperature. After 12 hours, the reaction was taken out from the reactor and the solution turned to be dark reddish. TLC and LCMS showed the reaction was finished. After the crude was concentrated, the crude was loaded on ISCO (silica, 8 g) with hexanes/EA 1:0 to 1:1 to give the desired product Compound 21 as a brown solid (0.63 g, 99%). The chiral HPLC confirmed 92 ee of the desired product.

$^1$H NMR (500 MHz, CDCl$_3$) δ 8.59 (d, J=5.2 Hz, 1H), 7.69 (d, J=1.8 Hz, 1H), 7.25 (dd, J=5.2 and 1.8 Hz, 1H), 3.17 (s, 6H), 2.39-2.31 (m, 1H), 2.14-2.03 (m, 2H), 1.65-1.57 (m, 1H), 1.35-1.20 (m, 1H), 1.07 (d, J=7.0 Hz, 3H), 0.98-0.90 (m, 1H).

LRMS: [C$_{14}$H$_{20}$ClNO$_4$—OCH$_3$]$^+$, 270.18, 270.19.

Example 14

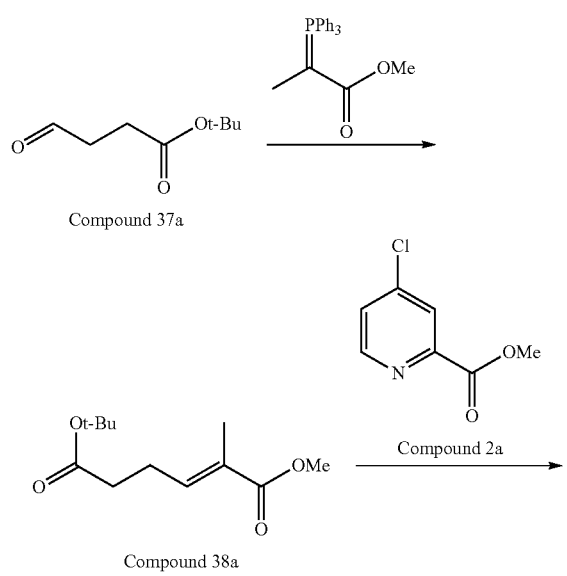

Compound 37a

Compound 38a

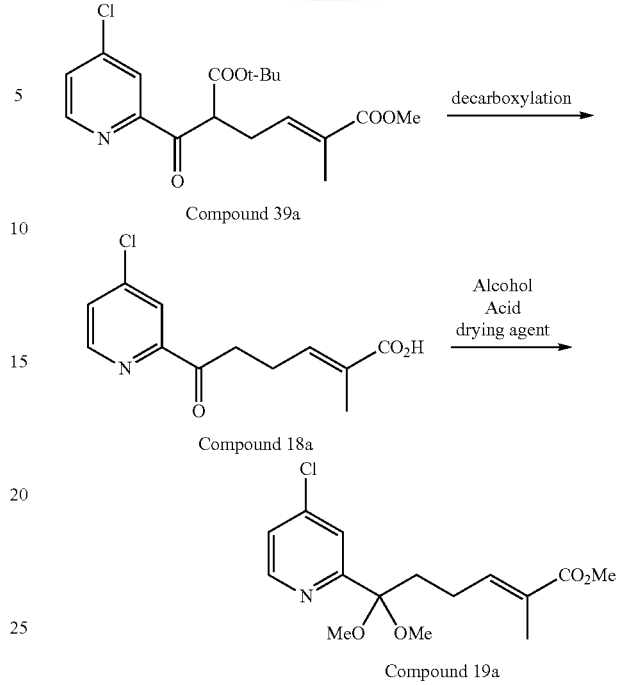

Compound 39a

Compound 18a

Compound 19a

Compound 37a (2.8 g) and methyl 2-(triphenyl-15-phosphaneylidene)propanoate (11 g) were dissolved in DCM (100 mL) and stirred for 4 hours at room temperature. After complete conversion, the solvent was removed under reduced pressure and the obtained residue was purified by silicagel chromatography to product 6.9 g of desired compound 38a.

$^1$H NMR (CDCl$_3$, 400 MHz): δ 6.69 ppm, (1H, m); 3.72 ppm (3H, s), 2.45-2.41 (2H, m), 2.36-2.32 (2H, m), 1.84 (3H, s), 1.43 (9H, s).

Compound 38a (3 g) and compound 2a (3.4 g) were dissolved in THF (30 mL) and the reaction mixture was cooled to −10° C. Then LiHMDS (29 mL, 2.207 eq) was added dropwise. After complete conversion, the reaction mixture is quenched with sat NH$_4$Cl (150 mL and further extracted with EtOAc (250 mL*2). The organic layer was dried over Na$_2$SO$_4$, filtered and concentrated. The obtained crude Compound 39a (11 g) was dissolved in ACN (220 mL), water (110 mL) and methane sulfonic acid (100.5 g, 34.967 eq). The reaction was warmed to 65° C. until complete conversion. After cooling to room temperature, pH was adjusted to 5-7 with concentrated solution of NaOH. The organic layer was extracted with EtOAc (500 mL×2), dried over Na$_2$SO$_4$ and filtered to afford compound 18a (10.8 g).

The obtained compound 18a was dissolved in TMSCl (24.4 g, 4.928 eq), trimethyl orthoformate (3 39 g, 8.064 eq) and MeOH (200 mL). The reaction mixture was warmed to 45-50° C. and stirred overnight. After cooling to room temperature, the reaction mixture was neutralized with sat. NaHCO$_3$ solution (200 mL). The aqueous layer was extracted with DCM (3*400 mL) dried over Na$_2$SO$_4$, filtered and reduced under reduced pressure. The obtained residue was purified by column chromatography on silica gel with petroleum ether/EtOAc (from 50:1 to 3:1) to afford compound 19a (10.4 g). $^1$H NMR (CDCl$_3$, 400 MHz): δ 8.56 ppm (1H, d, J=8 Hz), 7.70 ppm (1H, s), 7.24 ppm (1H, dd, J=4 Hz, 8 Hz), 6.52 ppm (1H, t, J=4 Hz), 3.68 ppm (3H, s), 3.18 ppm (6H, s), 3.24-3.20 (2H, m), 1.86-1.83 (2H, m).

Example 15

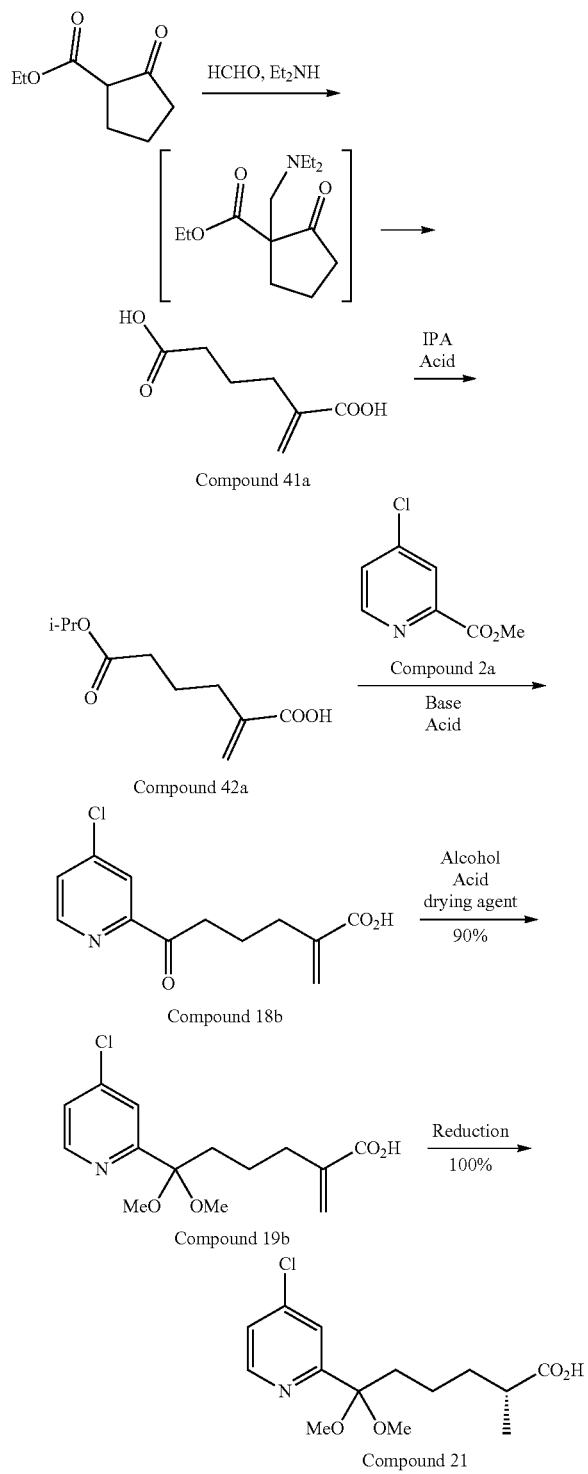

Paraformaldehyde (1.44 g, 1.5 eq) was charged to reactor under nitrogen followed by MeOH (25 ml, 5 vol) followed by ethyl 2-oxocyclopentane-1-carboxylate (5 g, 1 eq) and finally diethylamine (7.02 ml, 2.1 eq). Stir reaction mixture at 20-25° C. for at least 3.5 h. After complete conversion, sodium hydroxide (6M, 26.6 ml, 5 eq) was charged and stirred at 20-25° C. for at least 2 hours until complete conversion. MeOH was distilled off under vacuum. Then MTBE (25 ml, 5 vol) was charged to reaction mixture and stir for 10 mins. The layers could settle then upper organic layer was discharged to waste. 6M HCl aqueous solution was added to the lower aqueous layer till pH 2. EtOAc (25 ml, 5 vol) was charged and the reaction mixture was stirred for at least 10 mins. After phase separation and water washes. The organic layer was concentrated to dryness to give Compound 41a that was directly dissolved in iPrOH (50 mL, 10 vol.) and $H_2SO_4$ (1 eq.) at room temperature and stirred for 72 hours. The pH of the reaction mixture was adjusted to 7.3 with 20% aq. $K_2HPO_4$. After phase separation, the iPrOH layer was diluted with 20% aq. $K_2HPO_4$ (10 vol.) and washed with toluene. Finally, the pH of aqueous layer was adjusted to 4.7 with 2M $H_2SO_4$. The desired Compound 42a was extracted with toluene and isolated after solvent removal under reduced pressure.

$^1$H NMR (400 MHz, $CDCl_3$): δ 6.33 ppm (1H, s); 6.69 (1H, s); 5.05-4.98 (1H, m); 2.37-2.29 (4H, m), 1.87-1.80 (2H, m), 1.24 (6H, d=4 Hz).

Methyl 4-chloropicolinate (0.86 g, 1 eq) was charged to a nitrogen flushed 3 neck-flask at 20-25° C. followed by compound 42a (1 g, 1 eq) at 20-25° C. and THF (10 mL, 10 vol) at 20-25° C. After cooling to −30° C., LiHMDS was charged 1M in THF (12.49 mL, 2.5 eq) dropwise over 30 minutes keeping temperature ≤−25° C. and stirred for at least 1 hour at −20° C. After full conversion, acetic acid (0.9 mL, 3 eq) was added dropwise keeping T<−10° C. and the reaction mixture could warm to RT. EtOAc (50 mL, 50 vol) was added and the organic layer was washed with water and brine. After concentration under reduced pressure, a solution of water (15 mL, 15 vol) and sulfuric acid (6.7 mL, 25 eq) was slowly added. The reaction mixture was then heated to 65° C. for at least 17 hours at 65° C. Cool reaction mixture to 20-25° C. After complete conversion, reaction mixture was diluted with water (10 mL, 10 vol) and neutralized with 33% ammonium hydroxide until pH 4. Compound 18b was collected as solid and dried.

$^1$H NMR (500 MHz, DMSO): δ 8.7 ppm (1H), 7.9 ppm (1H), 7.8 ppm (1H), 6.0 ppm (1H), 5.6 ppm (1H), 3.1 ppm (2H), 2.3 ppm (2H), 1.8 ppm (2H).

Compound 18b (5 g) was dissolved in TMOF (4 eq), $H_2SO_4$ (1.1 eq), MeOH (4 vol) and stirred overnight at 50° C. After complete conversion, NaOH (6.4M, 8 eq) was added and stirred for 2 h. After MeOH distillation under reduced pressure, the reaction mixture was added with DCM and pH adjusted to 5 using 30% aq citric acid. After DCM extraction, water wash, the organic layer was concentrated to dryness. The obtained residue was dissolved in MeCN (2.5 vol) and heated to 45° C. The reaction was slowly cooled to 0° C. and stirred for 1 hours. Finally water (10 vol) was added in 2.5 vol portions. After filtration and cake wash, Compound 19b was obtained as solid in 88% yield.

$^1$H NMR (500 MHz, $CDCl_3$): δ 8.6 ppm (1H), 7.8 ppm (1H), 7.6 ppm (1H), 7.2 ppm (1H), 5.5 ppm (1H), 3.2 ppm (6H), 2.2 ppm (2H), 2.1 ppm (2H), 1.1 ppm (2H).

In a 5 mL vial equipped with a magnetic stirrer, the [RuCl(p-cymene)((R)-H8-binap)]Cl (0.0003 mmol) was added in DCM stock solutions (100 μL). Next, Compound 19b (0.075 mmol) was added as stock solution (1 mL) of MeOH/DCM 3/1 followed by the addition of TEA (0.375 mmol). The vial was capped and transferred to the B48 parallel reactor. The reactions were run at 25° C. overnight (ca. 16 h) under H$_2$ atmosphere (40 bar). The reactions were analyzed by HPLC providing the desired compound 21.

Example 16

Crystallization of Compound 21

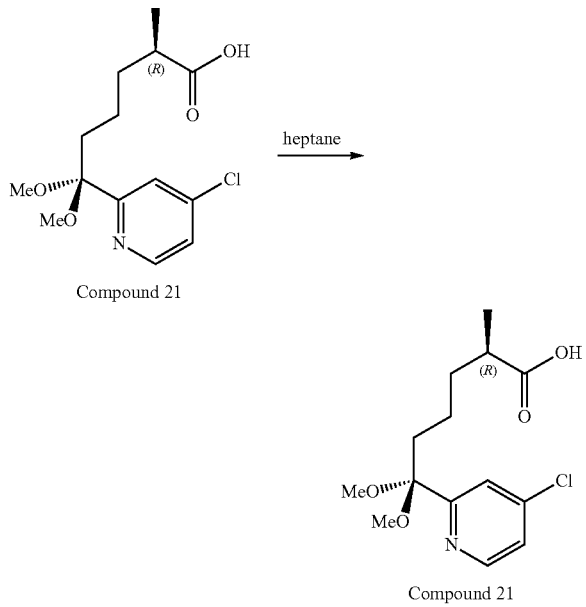

Crude Compound 21 (1.0 g) was suspended in 25-30 mL heptane and stirred to 40° C. till clear solution. After cooling to 35° C., the reaction mixture was seeded and the mixture was stirred for 2-4 hours and later cooled down to −5° C. over 8-10 h. After 6-10 h at −5° C., the cake was filtered, washed, dried in oven at 30° C. mp: 64° C.

Example 17

Enzymatic Approach to the Synthesis of Compound 27 a). Synthesis of Compounds 24a and 25a

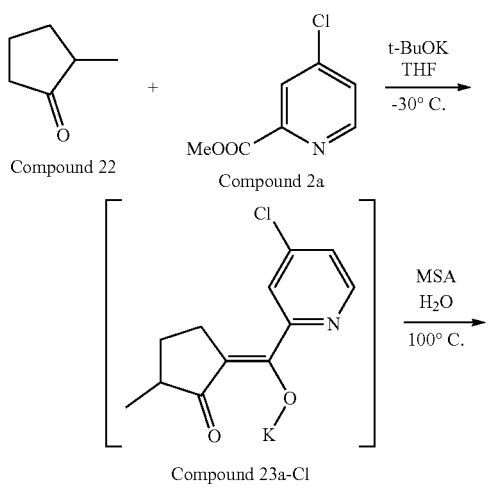

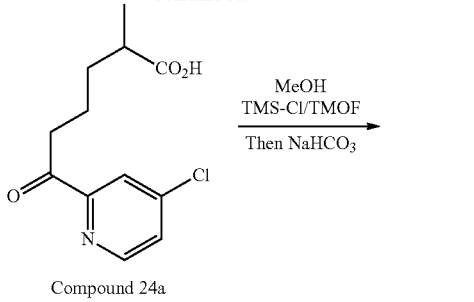

Compound 24a

Compound 25a

To a slurry of a mixture of 2-methylcyclopentanone, Compound 22 (93.30 g, 931.7 mmol, 98 mass %), Compound 2a (158.02 g, 902.55 mmol, 98 mass %) in THF (1500 mL, 18400 mmol, 100 mass %) was added potassium tert-butoxide (1 mol/L) in THF (1200 g, 1330 mmol, 1 mol/L) at −30° C. The resulting yellow slurry was stirred at between −24 to 30° C. for 1 h. In a separate 4 L rector was charged with sulfuric acid (13.14 mol/L) in water (92 g, 660.2 mmol, 13.14 mol/L) and water (800 g, 44407.9 mmol, 100 mass %) and was precooled to 0° C. The yellow slurry containing Compound 23a-Cl was poured into the cold acid solution and resulted in a slurry. THF was distilled off at 15° C. with jacket set at 45° C. under vacuum, 115 mbar. To the slurry (~1 Liter) was added 500 mL of water. The precipitated solids were collected and the aqueous was discarded. The collected solids were charged back to the reactor along with 320 mL of MSA and 1 Liter of water. The slurry was heated to 65° C. and all the solids were dissolved after 60 minutes. The dark solution was held for 3 h at 65° C. before it was cooled to rt then 0° C. A slurry was formed and was filtered. The Compound 24a was collected and dried at rt, a total amount of 139.8 g beige colored solids were obtained. The filtrate was charged back to the reactor and the pH was adjusted to 5.1 with 28 wt % NH$_4$OH. Solids were formed during the pH adjustment and was filtered at rt. Additional 41 g of off white solids of Compound 24a were obtained.

$^1$H NMR (400 MHz, DMSO-d$_6$): δ 12.07 (1H, s), 8.70 (d, J=5.31 Hz, 1H), 7.94 (dd, J=7.94, 1.77 Hz, 1H), 7.82 (dd, J=5.18, 2.15 Hz, 1H), 3.15 (m, 2H), 2.35 (m, 1H), 1.60 (m, 3H), 1.42 (m, 1H), 1.05 (d, J=6.82 Hz, 3H).

LRMS: [C$_{12}$H$_{14}$ClNO$_3$+H]$^+$, 258.24, 256.25.

178.27 g of Compound 24a were then charged into a 2 L-reactor, followed by 3.4 Liter MeOH, 380 mL TMOF, 210 mL of TMSCl. The mixture was heated to 49° C. with jacket set at 57° C. After additional 4 h at 50° C., the dark solution was cooled to 10° C. and was then charged into a solution of NaHCO$_3$ (2.6 liter saturated) in a 20 Liter reactor, total volume 6.5 Liter.

Most MeOH solvent was distilled off with jacket at 35° C. under vacuum down to 3.3 Liter volume. Then 2 Liter of MTBE was added. The organic layer was separated from the aqueous and was concentrated to provide 207 g of Compound 25a as a colored liquid.

$^1$H NMR (400 MHz, DMSO-$d_6$): δ 8.60 (d, J=5.05 Hz, 1H), 7.60 (d, J=1.77 Hz, 1H), 7.52 (dd, J=5.31, 2.02 Hz, 1H), 3.50 (s, 3H), 3.02 (br s, 6H), 2.30 (m, 1H), 2.00 (m, 2H), 1.40 (m, 1H), 1.22 (m, 1H), 0.93 (d, J=7.07 Hz, 3H), 0.79 (m, 2H).

LRMS: $[C_{18}H_{22}ClNO_4—OCH_3]^+$, 284.76.

Kilogram Scale Batch

To a mixture of 2-methylcyclopentanone, Compound 22 (235 kg, 0.66×, 1.16 eq.) and Compound 2a (354 kg, 1.0×) in 2-Me-THF (2103 L, 5.1×, 5.9 V), was added potassium tert-butoxide (258 kg, 0.73×, 1.1 eq.) by portions under N2 at 0° C. during 5 h. After 2 h, the reaction mixture was quench with water (2839 kg, 8×, 8 V; Pre-cool to 3-8° C.) at 0° C. during 4 h. The aqueous layer was separated and washes with toluene (3003 L, 2613 kg, 7.4×, 8.5 V) at 0° C. adjusting pH to 7.0-9.0 (8.68) at 0° C. during 5.5 h by dosing 5% H2SO4 aqueous solution (1970 kg, 5.6×, 0.49 eq.), then further adjust the pH to 4.0-6.0 (4.92) at 0° C. during 2 h by dose 0.5% H2SO4 solution (611 kg, 1.7×, 0.02 eq.). The mixture is stirred at 0° C. for 30 min, then filter by centrifuge and rinse with water (1495 kg, 4.2×, 4.2 V) to obtain 565 kg wet solid of compound 23 was obtained.

Compound 23 (7.60 kg, correct assay=7.50 g, 32.37 mmol) was added to the reaction mixture containing MSA (7.60 kg, 79.08 mol), H$_2$O (90.00 g, 90 ml) and ACN (29.25 kg, 37 L). Heat the reaction mixture to 68° C. and stir for 5 h. The reaction mixture was cooled to 20° C. then 25% Ammonia solution (5.50 kg) was dosed to the reaction mixture in portions and stirred for 1 h. 2.5% Ammonia solution (1.50 g) was dosed to the reaction mixture in portions within 30 mins to pH 4.8. Heat the reaction mixture to 43° C. for 8 h then filtered to obtain 40 kg of Compound 24a.

37.0 kg of Compound 24a was mixed in 370 L of MeOH with 3.0 eq CH(OMe)$_3$ and 2.0 eq TMSCL. After stirring the mixture for 24 h at 30-35° C. The reaction mixture was cooled to 20-25° C. and quenched by 2.2 eq of TEA at 20-30° C. Then, the reaction mixture was concentrated to 100 L under vacuum, below 40° C. 370 L of MTBE and 300 L of H$_2$O were added into the residue. After phase separation, organic layer was collected. And 200 L of H$_2$O was used to wash the organic phase. The organic phase was concentrated to 70 L under vacuum, below 40° C. Then 1 V of DMSO was added into the residue and the mixture was concentrated to 70 L under vacuum, below 40° C. to obtain 86.4 kg concentrated DMSO solution of Compound 25a.

b). Enzymatic Resolution of Dimethoxy Methyl Ester

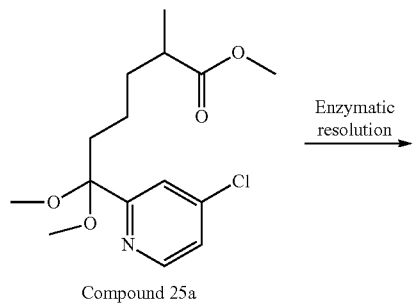

Compound 25a

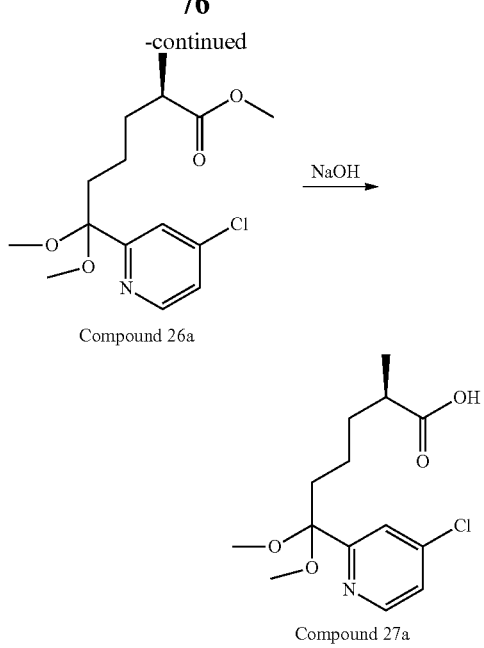

Compound 26a

Compound 27a

A jacketed 250 mL reactor with a water circulator to maintain the reaction temperature at 35° C. was used during the course of the reaction. A calibrated pH stat was used to maintain the pH at 7.0. To a 250 mL reactor charge 5.0 g of Compound 25a, 4.0 ml (2%) DMSO and 180 ml sodium phosphate buffer (0.1M, pH 7.0). A continuous supply of 5N sodium hydroxide was used to maintain reaction at pH 7.0. Lipase MH Amano 10 SD 1.0 g was dissolved in 10 mL of same buffer and added into the reactor. Another 6.0 mL buffer was used to rinse the enzyme container and that was charged into the same reactor. Samples (80 µL) were pipette out, diluted with 1.920 mL of methanol, vortexed, centrifuged for 2 min, filtered and analyzed by achiral and chiral HPLC. The reaction was stopped after 23 h and pH was increased to 8.2 by using 10 N sodium hydroxide. The reaction was extracted with 200 mL of ethyl acetate. All the dimethoxy methyl ester was extracted into organic layer. Organic layer was back extracted with sodium potassium buffer of pH 8.5 (2×50 mL) to remove the acid. Organic layer was washed with brine (50 mL), water (50 mL) and dried over anhydrous sodium sulfate. The solution was filtered, solvent was removed under vacuum and the residue was dried overnight in the vacuum oven. 1.88 g of Compound 26a was isolated as a brownish liquid yield 37.6%, ee 98.7%.

$^1$H NMR (400 MHz, DMSO-$d_6$) δ 8.61 (d, J=5.1 Hz, 1H), 7.60 (d, J=1.5 Hz, 1H), 7.52 (dd, J=5.2, 2.1 Hz, 1H), 3.50 (s, 3H), 3.03 (s, 3H), 3.03 (s, 3H), 2.31 (sxt, J=7.0 Hz, 1H), 2.05-1.95 (m, 2H), 1.47-1.35 (m, 1H), 1.28-1.17 (m, 1H), 0.94 (d, J=7.1 Hz, 3H), 0.85-0.74 (m, 2H).

LRMS: $[C_{15}H_{22}ClNO_4—OCH_3]^+$, 284.2/286.1.

c). Hydrolysis of Compound 26a to Give Compound 27a

To a reaction vial charge Compound 26a (1.0 g), methanol (20 mL), water (5.0 mL) and 500 µL (0.2 g) of 10 N sodium hydroxide. The reaction was stirrer at room temperature for 5 h. Samples (30 µL) were taken out, diluted with methanol (970 µL), vortexed, filtered and analyzed by HPLC. Most of the reaction (~98% conversion) was over in <2 h and no racemization was observed during the hydrolysis. The reaction mixture was concentrated to an oil, diluted with 20 mL water (pH 12.7). The reaction mixture was extracted with MTBE (2×50 mL) and MTBE was discarded. Aqueous layer was cooled and acidified to pH 3.8 with 850 μL of 6N HCl. Aqueous layer was extracted with MTBE (2×50 mL), MTBE solution was washed with brine (25 mL) and water (2×25 mL). MTBE solution was dried over anhydrous sodium sulfate, filtered, solvent was removed and the residue was dried overnight in the vacuum oven. Compound 27a was isolated as a viscous yellow liquid, 940 mg, yield 98.3%, AP 97 and Ee 98%.

$^1$H NMR (400 MHz, DMSO-$d_6$) δ 11.96 (s, 1H), 8.60 (d, J=5.3 Hz, 1H), 7.60 (d, J=2.0 Hz, 1H), 7.51 (dd, J=5.2, 2.1 Hz, 1H), 3.04 (s, 3H), 3.01 (s, 3H), 2.18 (sxt, J=6.9 Hz, 1H), 2.00 (dd, J=10.6, 5.8 Hz, 2H), 1.47-1.33 (m, 1H), 1.26-1.13 (m, 1H), 0.91 (d, J=6.8 Hz, 3H), 0.87-0.75 (m, 2H).

LRMS: $[C_{14}H_{20}ClNO_4]^-$, 300.1.

Alternate Enzymatic Resolution

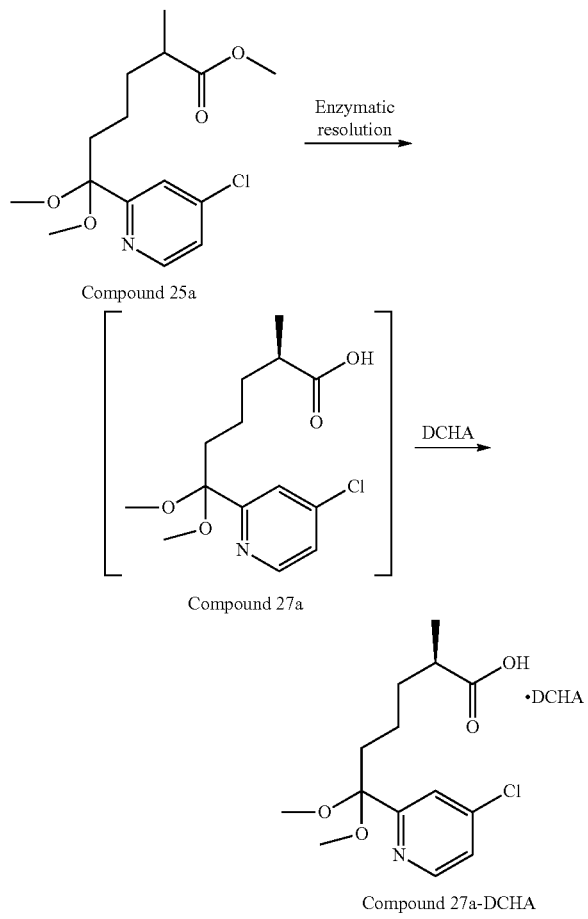

13.5 L of Tris buffer 0.1 M with 50 mM Ca(OAc)$_2$ was mixed with 2.5 w % enzyme (Almac Hydrolase L90 enzyme, also known as AL-L90, commercially available from ALMAC Group Ltd., Craigavon, Northern Ireland, UK) at 20-25° C. the pH of the mixture was corrected to 7.2-7.8. The mixture was heated to 38-42° C. and the pH was maintained at 7.2-7.8. A Solution of 1.5 kg of compound 25a in 1.5 L of DMSO was added into the mixture in one portion at 38-42° C. After 22 h, the conversion was 49%. the reaction mixture was cooled to 5° C., and the mixture was held at 0-10° C. for 16 h. Workup: 9 L of ACN was added into the reaction mixture at 0-10° C. Then the pH was adjusted to 10.0 by 20% of K$_2$CO$_3$, and 0.25× celite was added into the mixture. After stirring for 20-30 min, the reaction mixture was filtered and rinsed the cake with 3 L of MTBE and 3 L of water. The filtrate was collected and 15 L of MTBE was added into the mixture to do phase separation. 15 L of water was used to wash the organic layer twice. The aqueous phases were combined and adjusted pH=5.5 by 20% citric acid. 15 L of MTBE was added into the mixture to do phase separation. Then the aqueous layer was adjusted to pH=5.5 by 20% citric acid and 15 L of MTBE was used to do phase separation again. The organic phases were combined and washed with 15 L of process water. The organic phase was collected and filtered to remove aqueous layer. Then the organic phase was concentrated to 4.5 L. 15 L of MTBE was used to do azeotropic distillation to 4.5 L twice. 7.5 L of MTBE and 3 L of ACN was added into the residue for salt formation. Salt formation: The mixture was heated to 50-55° C., and DCHA (0.75 eq) was added into the mixture at 50-55° C. After stirring for 1 h at 50-55° C., the reaction mixture was cooled on 10° C./h. 1.8% of seed was added into the mixture at 38.2° C. White solid was slowly precipitated out. After holding at 38° C. for 3 h, the mixture was continued to cool on 10° C./h. After holding for 10 h at 0-5° C., the mixture was filtered. 1.5 L of pre-cooling ACN was used to rinse the cake. After drying for 38 h, 1.245 kg of Compound 27a-DCHA white solid was obtained with 99.3% purity, 99.4% ee and 43.61% isolated yield.

Example 18

Synthesis of Compound 10

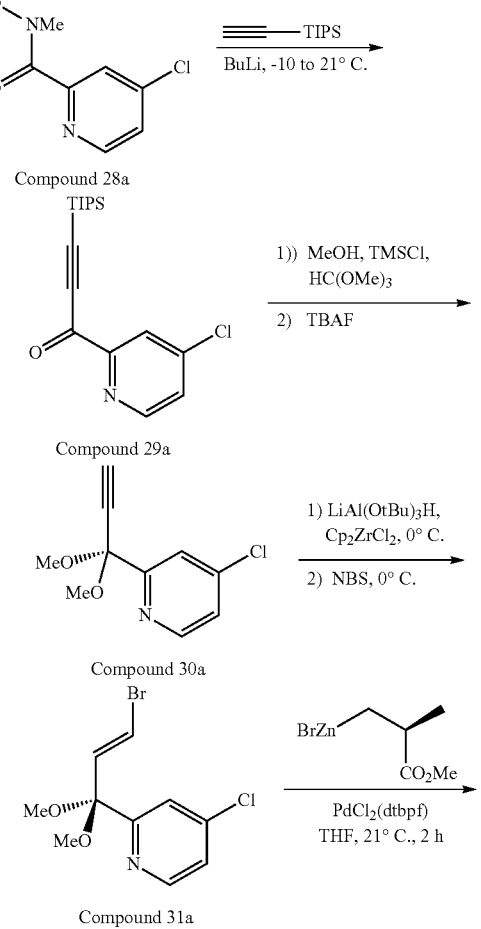

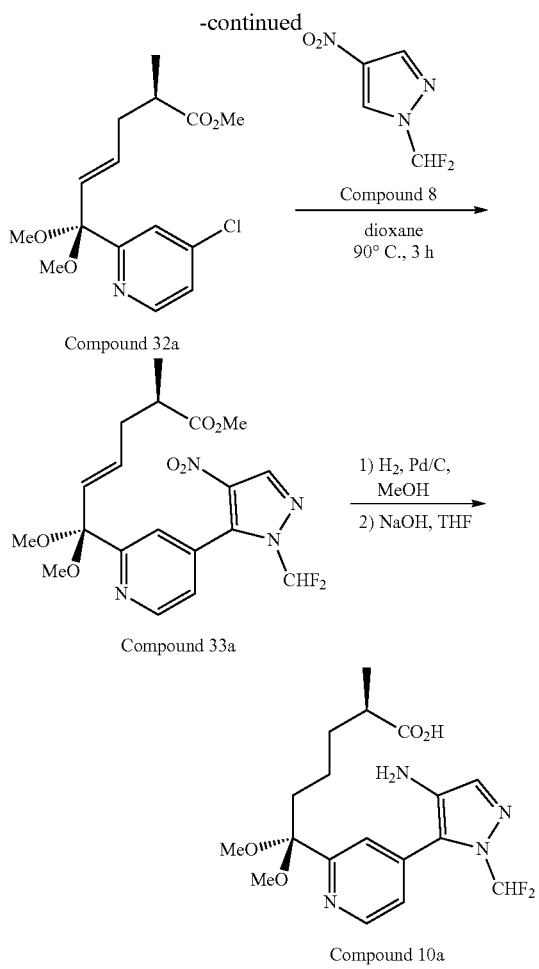

Compound 32a

Compound 33a

Compound 10a a). Synthesis of Compound 29a

To a solution of (triisopropylsilyl)acetylene (10.5 g, 57.6 mmol, 100 mass %) in THF (60 mL) was slowly added n-butyl lithium (2.5 mol/L) in hexanes (22 mL, 55.0 mmol, 2.50 mol/L) at −10° C. After the addition, the mixture was warmed to 21° C. A solution of Compound 28a (10.0 g, 49.8 mmol, 100 mass %) in THF (35 mL) was then added at 21° C. After 1 h, HPLC analysis indicated that 8% the amide starting material remained. lithium bis(trimethylsilyl)amide (1 M in THF, 8 mL) was then added. After 1 h, HPLC analysis indicated the reaction completion. The mixture was cooled to 0-5° C., and added into a mixture of 15% aqueous citric acid (500 g) and heptane (0.6 L) at 5-15° C. The organic layer was washed with 3% aqueous citric acid (200 mL) and water (0.2 L), dried over MgSO₄, and concentrated to give 15.8 g of the Compound 29a as an orange oil in 98.5% yield.

$^1$H NMR (500 MHz, CDCl₃): δ 8.68 (TH, d, J=4.5 Hz), 8.15 (TH, s), 7.50 (1H, d, J=4.5 Hz), 1.25-1.05 (21H, m).

LRMS: [C₁₇H₂₄ClNOSi+H]⁺, 322.23/324.11.

b). Synthesis of Compound 30a

To a solution of Compound 29a (3.00 g, 9.32 mmol-) in MeOH (20 mL) was added trimethyl orthoformate (2.0 mL, 18 mmol-), followed by chlorotrimethylsilane (3.0 mL, 24 mmol) at 21° C. The mixture was subsequently heated at 60° C. After 1 h, HPLC analysis indicated that the starting material consumed. The mixture was cooled to 21° C., and added into a mixture of hexanes (200 mL) and an aqueous solution of NaHCO₃ (15 g)/Na₂CO₃ (5 g) in water (200 mL). The separated organic phase was then dried over MgSO₄, and concentrated to give 3.45 g of [3-(4-chloro-2-pyridyl)-3,3-dimethoxy-prop-1-ynyl]-triisopropyl-silane (3.45 g, 9.38 mmol, 100% Yield) as an orange oil. The crude intermediate was used for subsequent deprotection of TIPS without further purification.

To a solution of [3-(4-chloro-2-pyridyl)-3,3-dimethoxy-prop-1-ynyl]-triisopropyl-silane (3.20 g, 8.70 mmol, 100 mass %) in 2-MeTHF (10 mL) and TBME (10 mL) was added tetrabutylammonium fluoride, 1 M in THF (12 mL, 12.0 mmol, 1.00 mol/L) at 21° C. After 10 min, HPLC analysis showed the starting material consumed. The dark mixture was added into a mixture of TBME (0.2 L) and an aqueous solution of K₂HPO₄/K₃PO₄ (20 g/5 g in 130 mL of water). The isolated organic phases were dried over MgSO₄, and concentrated. The resulting residue was purified by column chromatography (20 to 60% EtOAc/heptane; Rf 0.39 in 50% EtOAc/heptane) to give 1.65 g of Compound 30a as pale solids in 90% yield.

$^1$H NMR (500 MHz, CDCl₃): δ 8.61 (1H, d, J=5.0 Hz), 7.75 (1H, s), 7.32 (1H, d, J=5.0 Hz), 3.37 (6H, s), 2.74 (1H, s).

LRMS: [C₁₀H₁₀ClNO₂—OCH₃]⁺, 180.25/182.06.

c). Synthesis of Compound 31a

To a solution of bis(cyclopentadienyl)zirconium dichloride (20.7 g, 70.9 mmol, 99 mass %) in THF (200 mL) was added lithium tri-tert-butoxyaluminum hydride (1 mol/L) in THF (71 mL, 71 mmol, 1 mol/L) at 7 to 15° C., and stirred for 1 h at 0-5° C. Compound 30a (12.5 g, 59.1 mmol, 100 mass %) was then added at 0-5° C. After mixed for 10 min at 5-10° C., the mixture was warmed to 21° C., and stirred for 0.5 h at the temperature. The dark brown solution mixture was then cooled to 0-5° C., and NBS (11 g, 61.8 mmol, 100 mass %) was added as solids in two portions (first 6 g, then 5 g).

After stirring for 2 h at 5-10° C., the reaction mixture was added into a mixture of EtOAc/heptane (180 mL/60 mL) and 15% aqueous solution of NH₄Cl (250 mL). The resulting slurry was filtered over a celite bed, and the process line was rinsed with EtOAc (30 mL×2). The aqueous phase was removed from the combined filtrates. The resulting organic phase was washed with 5% aqueous solution of K₂HPO₄, dried over MgSO₄, and concentrated. The residue was purified by column chromatography (0-30% EtOAc/heptane; Rf of the product 0.4 in 30% EtOAc/heptane) to give 13.2 g of Compound 31a (13.2 g, 45.1 mmol, 76.4% Yield) as grey solids.

$^1$H NMR (500 MHz, CDCl₃): δ 8.57 (1H, d, J=5.2 Hz), 7.67 (1H, s), 7.26 (1H, d, J=5.2 Hz), 6.78 (1H, d, J=13.5 Hz), 6.11 (1H, d, J=13.5 Hz), 3.24 (6H, s).

LRMS: [C₁₀H₁₁BrClNO₂—OCH₃—Br]⁺, 182.09/184.22.

d). Synthesis of Compound 32a

To a solution of Compound 31a (12.0 g, 41.0 mmol, 100 mass %) in THF (50 mL) was charged (S)-(−)-3-methoxy-2-methyl-3-oxopropylzinc bromide (0.5 mol/L) in THF (94 mL, 47 mmol, 0.50 M) at 5-10° C. The mixture was degassed by bubbling N₂ for 3 min. 1,1′-bis(di tert-butylphosphino)ferrocene palladium dichloride (0.68 g, 1.03 mmol, 100 mass %) was then added at 5-10° C. The resulting mixture was degassed by bubbling N₂ for 5 min. After 15 min at 5 C, the dark solution was warmed to 21° C. After 16 h, TBME (150 mL) was added into the reaction mixture, followed by aqueous solution of NH₄Cl (25%, 200 g). The dark organic phase was dried over MgSO₄, and concentrated. The resulting residue was purified by column chromatography (5-60% EtOAc/heptane; Rf 0.28 in 1:1

EtOAc/heptane) to give Compound 32a (11.7 g, 37.3 mmol, 100 mass %, 90.9% yield) as an orange oil.

$^1$H NMR (500 MHz, CDCl$_3$): δ 8.54 (1H, d, J=5.2 Hz), 7.65 (1H, s), 7.22 (1H, d, J=5.2 Hz), 5.98 (1H, dt, J=15.6, 7.3 Hz), 5.45 (1H, d, J=15.6 Hz), 3.62 (3H, s), 3.21 (6H, s), 2.63-2.52 (1H, m), 2.32-2.45 (1H, m), 2.16-2.20 (1H, m), 1.13 (3H, d, J=7.0 Hz).

LRMS: [C$_{15}$H$_{20}$ClNO$_4$—OCH$_3$]$^+$, 282.19/284.23.

e). Synthesis of Compound 33a

Catalysis preparation: diacetoxypalladium (440 mg, 1.960 mmol) and bis(1-adamantyl)-butyl-phosphane (708 mg, 1.975 mmol) was added into 12 mL of dioxane. The mixture was degassed by bubbling N$_2$ for 0.5 h. Compound 32a (6.2 g, 20 mmol, 100 mass %), Compound 8 (4.0 g, 25 mmol), -pivalic acid (1.1 g, 11 mmol, 100 mass %), potassium carbonate (8.1 g, 59 mmol) were mixed in 60 mL of dioxane, and the resulting mixture was degassed by bubbling N$_2$ for 0.5 h. The above premixed and degassed catalyst was then transferred into the mixture including the substrate. The resulting mixture was degassed by bubbling N$_2$ for 0.5 h, then heated at 90° C. and held at the temperature for 3 h before cooling to 21° C. The resulting mixture was filtered, and the process line was rinsed with TBME (25 mL). The combined filtrates were concentrated. The resulting residue was purified by column chromatography (Rf 0.36 in 60% EtOAc/heptane; 10-80% EtOAc/hetpane) to give 7.6 g of Compound 33a (7.6 g, 16 mmol, 98 mass %, 86% yield) as a brown oil.

$^1$H NMR (500 MHz, CDCl$_3$): δ 8.86 (1H, d, J=4.7 Hz), 8.33 (1H, s), 7.73 (1H, s), 7.22 (1H, d, J=4.7 Hz), 7.13 (1H, t, J=57.6 Hz), 5.97 (1H, dt, J=15.7, 7.6 Hz), 5.53 (1H, d, J=15.7 Hz), 3.59 (3H, s), 3.23 (6H, s), 2.65-2.52 (1H, m), 2.35-2.48 (1H, m), 2.19-2.25 (1H, m), 1.12 (3H, d, J=7.0 Hz).

LRMS: [C$_{19}$H$_{22}$F$_2$N$_4$O$_6$—OCH$_3$]$^+$, 409.18.

f). Synthesis of Compound 10a

To a 100 mL pressure flask was charged a solution of Compound 33 (6.3 g, 14 mmol) in MeOH (50 mL) and a magnetic stirring bar. The bottle was degassed by vacuum/refill with N$_2$, 6 times. Then Pd/carbon, 10 wt %; 50% wet; (1.35 g, 0.634 mmol, 5 mass %) was added. The vessel was degassed with N$_2$, then H$_2$. The hydrogen gas pressure was set at 80 psi and reaction temperature as 55° C. After held at the pressure and temperature for 12 h, the mixture was filtered and the process line rinsed with MeOH (35 mL). The combined filtrates were concentrated. The resulting residue was dissolved in THF (60 mL), and aqueous NaOH (1 mol/L) was added. The mixture was heated at 40° C., and held for 6 h at the temperature. The mixture was then cooled to 21° C. 2-MeTHF (100 mL) was added. The pH of the mixture was adjusted by addition of 85% H$_3$PO$_4$ to pH ~6. The aqueous layer was removed, and the organic phase was dried over MgSO$_4$, and concentrated. The resulting residue was purified by column chromatography (0-10% MeOH/DCM; Rf 0.4 in 10% MeOH/DCM) to give 4.85 g of Compound 10a (4.85 g, 12.2 mmol, 89.7% yield) as foaming solids.

$^1$H NMR (500 MHz, CDCl$_3$): δ 8.77 (1H, s, br), 7.75 (1H, s. br), 7.39 (1H, s. br), 7.33 (1H, s. br), 7.11 (1H, t, J=59.1 Hz), 5.75 (3H, s, br), 3.17 (6H, s), 2.35-2.25 (1H, m), 2.20-1.98 (2H, m), 1.55-1.43 (1H, m), 1.30-1.13 (1H, m), 0.80-1.09 (5H, m).

LRMS: [C$_{18}$H$_{24}$F$_2$N$_4$O$_4$+H]$^+$: 399.18.

Example 19

Synthesis of Compound 14

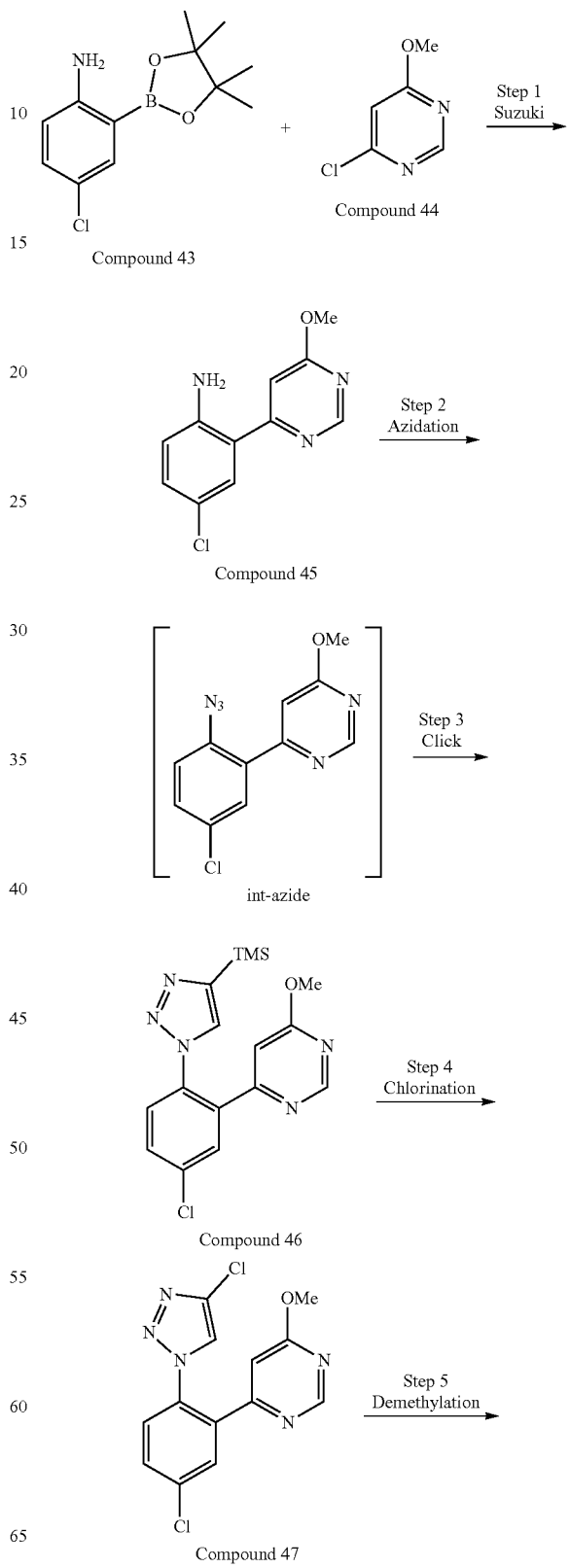

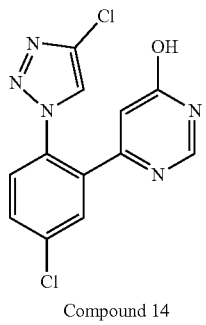 [SMILES: Oc1cc(-c2cc(Cl)ccc2-n2cc(Cl)nn2)ncn1]

Compound 14

Suzuki

A 2 L reactor was charged with acetonitrile (500 mL, 5 L/kg), Compound 43 (100 g, 1.0 equiv), Compound 44 (60 g, 1.05 equiv), 1,1,3,3-Tetramethylguanidine (93.2 g, 2.05 equiv) and water (70.8 g, 10 equiv). The reactor headspace was purged using a nitrogen flow. Pd(dppf)Cl$_2$·DCM (3.2 g, 1 mol %) was added to the reaction mixture and the reactor was heated to 65° C. in 1-7 hours and stirred at temperature for 1-17 hours. After reaction completion, 1,3,5-triazine-2,4,6(1H,3H,5H)-trithione sodium salt (TriNaTMT) (10 g, 10 w/w %) was dissolved in water (50 mL, 0.5 L/kg) and added to the reaction mixture. Warm water (280 mL, 2.8 L/kg) was then slowly dosed over 0.5-4 hours to the reaction mixture while keeping internal temperature at 60-65° C. After aging for 1-4 hours, warm water (350 mL, 3.5 L/kg) was then slowly dosed over 2-6 hours to the reaction mixture while keeping internal temperature at 60-65° C. The reaction mixture was then cooled down to 10-15° C. over 4-6 hours and further aged at 10-15° C. for 1-3 hours. The slurry was then filtered, and the cake washed with a cooled MeCN/water solution (2:1 v/v ratio, 5 L/kg). The Compound 45 cake was dried under vacuum at 45-50° C. overnight.

Typical results: 90-95% yield, 98 a % purity, >95% assay.

PD Removal

A 5 L reactor was charged with crude Compound 45 solid (100 g, 1.0 equiv), 2-methyltetrahydrofuran (MeTHF, 1.5 L, 15 L/kg) and an aqueous N-acetyl L-cysteine solution (32 g in 1.5 L water). The resulting mixture was stirred for 1-2 hours at 20-30° C. and filtered through Celite (30 g, 0.3 kg/kg). The biphasic mixture was left standing for 0.5-2 hours and the two layers were separated. The upper layer was kept in the reactor and an aqueous N-acetyl L-cysteine solution (32 g in 1.5 L water) was charged again. The resulting mixture was stirred for 1-2 hours at 20-30° C., the biphasic mixture was left standing for 0.5-2 hours and the two layers were separated. The upper layer was kept in the reactor and an aqueous sodium bicarbonate (70 g in 1 L water) was charged. The resulting mixture was stirred for 1-2 hours at 20-30° C., the biphasic mixture was left standing for 0.5-2 hours and the two layers were separated. The upper layer was kept in the reactor and an aqueous sodium sulfate (100 g in 1 L water) was charged. The resulting mixture was stirred for 1-2 hours at 20-30° C., the biphasic mixture was left standing for 0.5-2 hours and the two layers were separated. The upper layer was kept in the reactor and diluted with MeTHF (1 L, 10 L/kg) and the resulting solution was concentrated under vacuum to 500-600 mL (5-6 L/kg). The solution was then diluted with MeTHF (1 L, 10 L/kg) and the resulting solution was concentrated under vacuum to 500-600 mL (5-6 L/kg). The solution was then diluted with MeTHF (1 L, 10 L/kg) and the water content was measured (KF below 0.1%).

Typical results: 90-95% yield, 98 a % purity.

Azidation/Click

A reactor was charged with the Compound 45 MeTHF solution (100 g in 1.5 L MeTHF), MeTHF (1.5 L, 15 L/kg) and MeCN (1 L, 10 L/kg) and the resulting mixture was cooled to 5-10° C. TMSN3 (59.0 g, 1.2 equiv) was dosed slowly to the reactor. tBuONO (53.0 g, 1.2 equiv) was dosed slowly to the reactor and the mixture was stirred at 5-15° C. for 4-8 hours. An aqueous NaOH solution (100 g in 1 L water) was slowly added to the mixture which was then warmed up to 20-30° C., stirred for 20-30 min and left standing for 30-60 min at 20-30° C. After phase separation, the upper layer was left in the reactor and an aqueous NaOH solution (100 g in 1 L water) was slowly added to the mixture which was then stirred for 20-30 min and left standing for 30-60 min at 20-30° C. After phase separation, the upper layer was left in the reactor and an aqueous NaOH solution (100 g in 1 L water) was slowly added to the mixture which was then stirred for 20-30 min and left standing for 30-60 min at 20-30° C. After phase separation, the upper layer was left in the reactor and an aqueous NaOH solution (100 g in 1 L water) was slowly added to the mixture which was then stirred for 20-30 min and left standing for 30-60 min at 20-30° C. After phase separation, the upper layer was left in the reactor and the residual azide was measured (residual N$_3$<3 ppm). An aqueous sodium sulfate solution (100 g in 1 L water) was then added to the mixture which was then stirred for 20-30 min and left standing for 30-60 min at 20-30° C. After phase separation, an aqueous sodium sulfate solution (100 g in 1 L water) was added to the mixture which was then stirred for 20-30 min and left standing for 30-60 min at 20-30° C. After phase separation, an aqueous sodium sulfate solution (100 g in 1 L water) was added to the mixture which was then stirred for 20-30 min and left standing for 30-60 min at 20-30° C. After phase separation, an aqueous sodium sulfate solution (100 g in 1 L water) was added to the mixture which was then stirred for 20-30 min and left standing for 30-60 min at 20-30° C. After phase separation, the pH was measured (pH<9) and the organic azide solution was cooled to 5-15° C. After bubbling nitrogen for 20-40 min, triethylamine (95.0 g, 2.2 equiv) was charged slowly to the reaction mixture while keeping the temperature at 5-15° C. Trimethylsilylacetylene (50.0 g, 1.2 equiv) was charged slowly to the reaction mixture while keeping the temperature at 5-15° C. and the reactor was purged with nitrogen until the oxygen level was below 0.1%. Copper iodide (8.0 g, 10 mol %) was charged to the reactor which was then purged again with nitrogen until the oxygen level was below 0.1%. The reaction mixture was stirred at 5-15° C. for 8-16 hours. After reaction completion, the reaction mixture was warmed up to 20-30° C. and 1,3,5-triazine-2,4,6(1H,3H,5H)-trithione sodium salt (TriNaTMT) (10 g, 10 w/w %) was added. After 0.5-1.5 hours stirring at 20-30° C., the mixture was filtered through Celite (30 g, 0.3 kg/kg) and the cake was rinsed with MeTHF (250 mL, 2.5 L/kg). An aqueous ammonia solution (100 g in 1 L water) was charged in the reactor which was then stirred at 20-30° C. for 20-30 min and allowed to stand for 30-60 min at 20-30° C. After phase separation, an aqueous sodium sulfate solution (100 g in 1 L water) was charged in the reactor which was then stirred at 20-30° C. for 20-30 min and allowed to stand for 30-60 min at 20-30° C. After phase separation, the upper layer was filtered through Celite (30 g, 0.3 kg/kg). After washing the Celite cake with MeTHF (0.5 L, 5 L/kg), the mixture was concentrated at 45° C. under reduced pressure to 500-700 mL (5-7 L/kg). N-heptane (1 L, 10 L/kg) was added dropwise to the reactor and the resulting mixture was concentrated at 45° C. under reduced pressure to 500-700 mL (5-7 L/kg). N-heptane (1 L, 10 L/kg) was added dropwise to the reactor and the resulting mixture was concentrated at 45° C. under reduced pressure to 500-700 mL (5-7 L/kg). The reaction mixture was then warmed up to 55-60° C. and kept stirring at that temperature for 2-4 hours. After cooling the reactor to 5-15° C. over 3-8 hours, the slurry was aged at 5-15° C. and filtered. The Compound 46 cake was washed with n-heptane (1 L, 10 L/kg) and dried under reduced pressure at 40-45° C. for 6-12 hours.

Typical results: 85-90% yield, 98 a % purity, >95% assay.
Chlorination

A reactor was charged with Compound 46 (100 g, 1.0 equiv), DMF (500 mL, 5 L/kg), cooled to −15-(−5° C.) and purified water (5 g, 1.0 equiv). 1,3-dichloro-5,5-dimethylhydantoin (DCDMH, 13.7 g, 0.75 equiv) was charged in portions while keeping the internal temperature below 5° C. The internal temperature was then adjusted to 0-10° C. and the mixture was stirred at that temperature for 5-12 hours. After reaction completion, water (70 mL, 0.7 L/kg) was dosed to the reaction mixture over 0.5-1.5 hours while keeping the internal temperature below 15° C. Compound 47 seeds (0.1 g, 0.001 kg/kg) were added to the reaction mixture which was then aged for 1-2 hours at 0-10° C. Water (530 mL, L/kg) was dosed over 3-8 hours at 0-10° C. and the slurry was aged for 4-6 hours at 0-10° C. The mixture was filtered, and the cake was washed with cold water (0.5 L at 0-10° C.). The crude Compound 47 was dried under reduced pressure at 40-50° C. for 8-15 hours.

Typical results: 90-95% yield, 98 a % purity, >95% assay.
Compound 47 Recrystallization A reactor was charged with Compound 47 crude (100 g, 1.0 equiv), DCM (0.5 L, 5 L/kg) and the resulting solution was stirred for 0.5-2 hours at 20-30° C. The resulting mixture was filtered through a filter cartridge filled with charcoal and circulated for 3-8 hours and then concentrated under reduced pressure to 300-360 mL (3.0-3.6 L/kg). The mixture was then warmed up to 35-45° C. and refluxed for 20-40 min before being cooled down to 0-10° C. over 1-4 hours and further aged at 0-10° C. for 0.5-2 hours. N-heptane (1.6 L, 16 L/kg) was then charged to the reactor at 0-10° C. over 1-3 hours and the slurry was aged at 0-10° C. for 1-3 hours. After filtration of the slurry, the pure Compound 47 cake was washed with n-heptane (500 mL, 5 L/kg) and dried under reduced pressure at 40-50° C. for 6-12 hours.

Typical results: 90-95% yield, >99.5 a % purity, >95% assay.
Demethylation

A reactor was charged with pure Compound 47 (100 g, 1.0 equiv), aqueous HCl (35 w/w %, 320 g, 10 equiv) and the reactor was warmed up to 40-50° C. in 1-3 hours and stirred at that temperature for 10-18 hours. After reaction completion, an aqueous ammonia solution (50 g in 500 mL) was added dropwise to the reactor over 2-6 hours at 40-50° C. to reach pH=5-7. The reaction mixture was then cooled down to 0-10° C. in 1-3 hours and aged at that temperature for 1-3 hours. After filtration of the slurry, the crude Compound 14 cake was washed with cold water (1 L at 0-10° C., 10 L/kg) and dried under reduced pressure at 40-50° C. for 12-24 hours.

Typical results: 90-95% yield, >99.5 a % purity, >95% assay.
Compound 14 Recrystallization A reactor was charged with crude Compound 14 (100 g, 1.0 equiv), acetone (1.4 L, 14 L/kg) and the reactor was warmed up to 50-60° C. and stirred at that temperature for 1-3 hours. After seeding with Compound 14 (0.5 g, 0.005 kg/kg), n-heptane (1.7 L, 17 L/kg) was dosed at 50-60° C. over 4-8 hours and the mixture was stirred at that temperature for 1-2 hours before being cooled down to 5-15° C. over 2-4 hours. After filtration, the pure Compound 14 cake was washed with cold n-heptane (0.5 L, 5 L/kg) and dried under reduced pressure at 80-90° C. for 8-16 hours.

Typical results: 90-95% yield, >99.9 a % purity, >95% assay.

What is claimed is:

1. A process for the preparation of Compound (I):

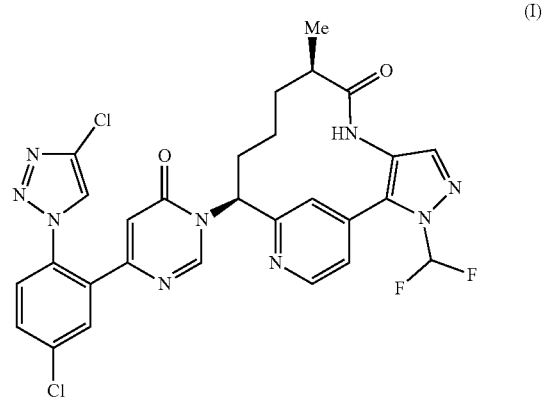 [SMILES: C[C@@H]1CCC[C@H](n2cnc(-c3cc(Cl)ccc3-n3cc(Cl)nn3)cc2=O)c2cc(ccn2)-c2c(cnn2C(F)F)NC1=O]

comprising the steps of:
1) reacting Compound 1

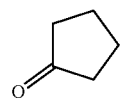

with Compound 2

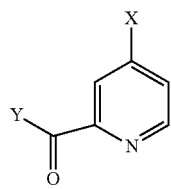

wherein
X is selected from Cl, Br, and I;
Y is selected from $OR^9$, $NHOC_{1-3}$ alkyl, Cl, Br, and I; and
$R^9$ is selected from $C_{1-3}$ alkyl, $C_{1-3}$ hydroxyalkyl, substituted phenyl and substituted benzyl; in a solvent to yield Compounds 3a or 3b

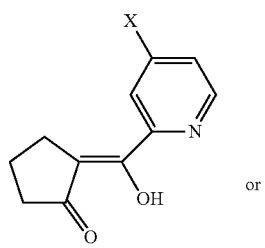

Compound 3a or

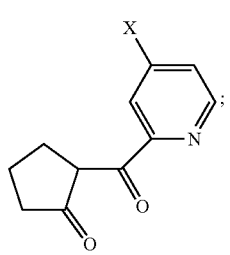

Compound 3b;

2) converting Compound 3a or 3b to yield Compound 4 of the formula in the presence of an acid

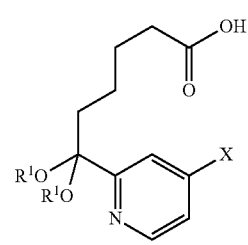

Compound 4

3) subsequently reacting Compound 4 in an alcoholic solvent with a tri-alkyl orthoformate to yield Compound 5

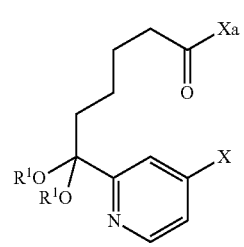

Compound 5 wherein $R^1$ is $C_{1-6}$ alkyl; and $R^{3'}$ is selected from $C_{1-6}$ alkyl, optionally substituted phenyl and benzyl;

4) hydrolyzing under basic condition or hydrogenolyzing when $R^{3'}$ is substituted benzyl to yield Compound 6

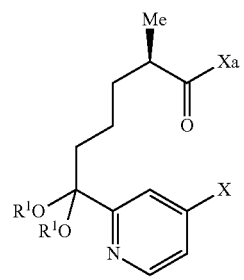

Compound 6 wherein $R^1$ and X are as defined above;

5) subsequently activating the carboxylic moiety of Compound 6 and reacting it with a chiral auxiliary to form Compound 6a

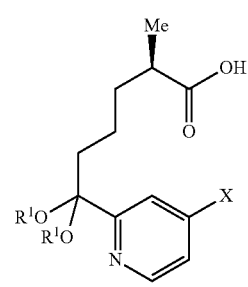

Compound 6a wherein Xa is a chiral auxiliary and $R^1$ and X are as defined above;

6) then reacting Compound 6a with a base in the presence of a methyl donor to yield Compound 6b

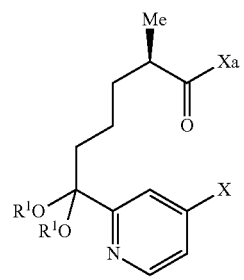

Compound 6b wherein $R^1$, X, and Xa are as defined above;

7) removing Xa to obtain Compound 7

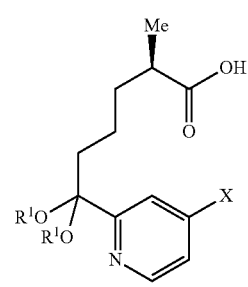

Compound 7 wherein $R^1$ and X are as defined above;

8) subsequently reacting Compound 7 in the presence of a metal catalyst with Compound 8 to yield Compound 9

9) reducing the nitro group in Compound 9 to yield Compound 10

10) cyclizing Compound 10 with a coupling agent to yield Compound 11

11) unmasking the ketone functionality in the presence of an acid to yield Compound 12 educing Compound 12 with 12a) an ammonia equivalent in the presence of a reducing agent or 12b) an transaminase enzyme in the presence of an amine source, a recycling system for the transaminase enzyme, and a co-factor to generate the amine stereogenic center present in Compound 13

13) which is then coupled with Compound 14 to yield Compound (I)

2. The process of claim 1 in Step 2), the acid is selected from sulfuric acid, methylsulfonic acid (MSA), benzenesulfonic acid, nitric acid, hydrochloric acid, trichloroacetic acid, and perchloric acid.

3. The process of claim 1 in Step 5), wherein the chiral auxiliary is selected from

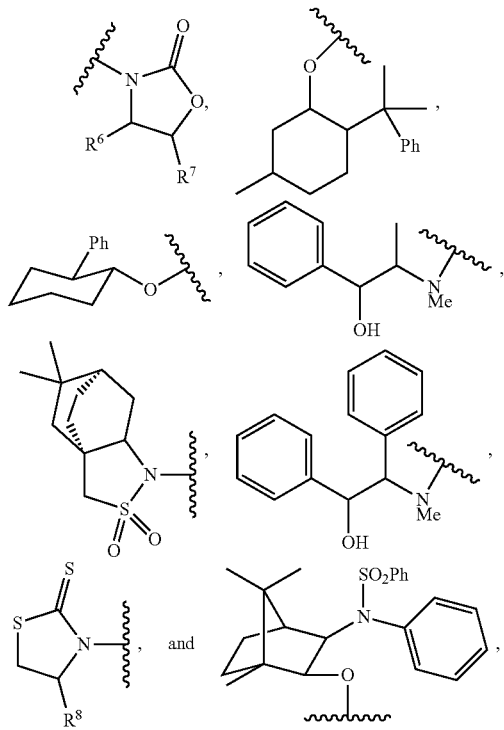

wherein
R$^6$ is selected from C$_{1-3}$ alkyl, phenyl, benzyl;
R$^7$ is selected from H and phenyl; and
R$^8$ is selected from C$_{1-3}$ alkyl, phenyl, and benzyl.

4. The process of claim 3 wherein the chiral auxiliary is selected from

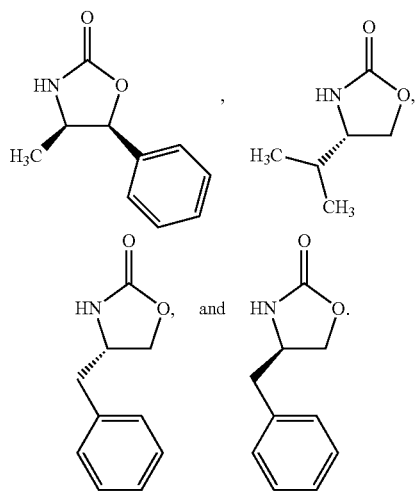

5. The process of claim 1 in Step 6), wherein the methyl donor is an alkyl halide.

6. The process of claim 1 in Step 8), wherein the metal catalyst comprises palladium and a phosphine ligand.

7. The process of claim 6, wherein the phosphine ligand is XPhos or SPhos.

8. The process of claim 1 in Step 10), wherein the coupling reagent is chloro-N,N,N',N'-tetramethylformamidinium hexafluorophosphate (TCFH).

9. The process of claim 1 in Step 12b), wherein the transaminase enzyme is selected from ATA-113, ATA-200, ATA-237, ATA-251, ATA-254, ATA-256, and ATA-260.

10. The process of claim 1 in Step 12b), wherein the co-factor is (4-formyl-5-hydroxy-6-methylpyridin-3-yl) methyl phosphate (PLP).

11. The process of claim 1 in Step 12b), wherein the amine source is selected from isopropylamine, alanine, 3-aminobutyric acid and methylbenzylamine.

12. The process of claim 11, wherein the amine source is isopropylamine.

13. The process of claim 1, further comprising preparing Compound 14:

Compound 14

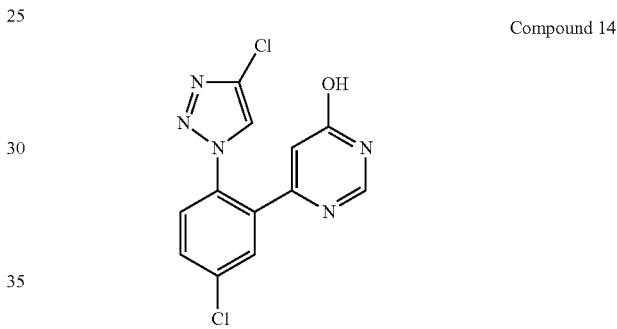

comprising the steps of:
1) Reacting Compound 43:

Compound 43

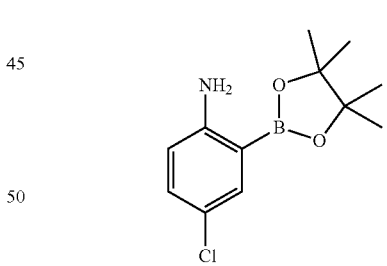

with Compound 44

Compound 44

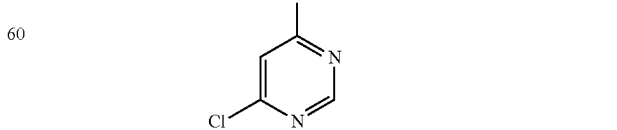

under Suzuki coupling conditions in a solvent to yield Compound 45:

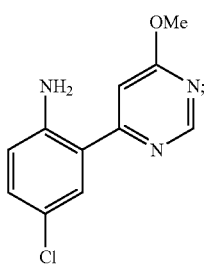
Compound 45
2) Converting Compound 45 to an azide, and reacting the azide with trimethylsilylacetylene and a metal catalyst in a solvent to yield Compound 46:
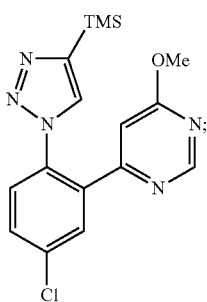
Compound 46
3) Reacting Compound 46 with 1,3-dichloro-5,5-dimethylhydantoin in a solvent to yield Compound 47:
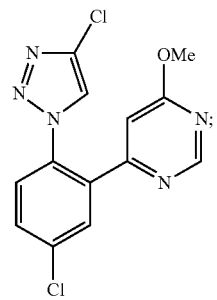
Compound 47
and
4) Demethylating Compound 47 in hydrochloric acid to yield the Compound 14.
* * * * *

UNITED STATES PATENT AND TRADEMARK OFFICE
CERTIFICATE OF CORRECTION

PATENT NO. : 12,378,246 B2  
APPLICATION NO. : 17/602059  
DATED : August 5, 2025  
INVENTOR(S) : Cuniere et al.

Page 1 of 1

It is certified that error appears in the above-identified patent and that said Letters Patent is hereby corrected as shown below:

On the Title Page

Column 1, item (54) (Title) Lines 4 and 5, delete "PYRIMIDINYL}- 1-" and insert
-- PYRIMIDINYL}-1- --.

Column 1, item (60) (Related U.S. Application Data), Lines 1 and 2, delete "Nov. 4," and insert
-- Apr. 11, --.

In the Specification

At Column 1, Lines 4 and 5, In the Title: delete "PYRIMIDINYL}- 1-" and insert
-- PYRIMIDINYL}-1- --.

In the Claims

At Column 87, Line 25 and 26, in Claim 1, delete "4 of the formula" and insert -- 4 --.

At Column 90, Line 14, in Claim 1, delete "educing" and insert -- reducing --.

At Column 92, Line 40, in Claim 13, delete "Reacting" and insert -- reacting --.

At Column 93, Line 14, in Claim 13, delete "Converting" and insert -- converting --.

At Column 94, Line 1, in Claim 13, delete "Reacting" and insert -- reacting --.

At Column 94, Line 29, in Claim 13, delete "Demethylating" and insert -- demethylating --.

Signed and Sealed this  
Eighteenth Day of November, 2025

John A. Squires  
*Director of the United States Patent and Trademark Office*